(12) United States Patent
Gravestock

(10) Patent No.: US 6,605,630 B1
(45) Date of Patent: Aug. 12, 2003

(54) ANTIBIOTIC OXAZOLIDINONE DERIVATIVES

(75) Inventor: Michael Barry Gravestock, Macclesfield (GB)

(73) Assignee: Syngenta Limited, London (GB)

(*) Notice: Subject to any disclaimer, the term of this patent is extended or adjusted under 35 U.S.C. 154(b) by 0 days.

(21) Appl. No.: 09/486,092

(22) PCT Filed: Aug. 18, 1998

(86) PCT No.: PCT/GB98/02476
§ 371 (c)(1),
(2), (4) Date: Feb. 18, 2000

(87) PCT Pub. No.: WO99/10342
PCT Pub. Date: Mar. 4, 1999

(30) Foreign Application Priority Data

Aug. 22, 1997 (GB) .............................. 9717807

(51) Int. Cl.$^7$ ..................... A61K 31/42; C07D 237/30; C07D 471/02; C07D 413/00

(52) U.S. Cl. ................. 514/376; 514/252; 514/255; 514/256; 514/311; 514/326; 514/331; 514/340; 514/362; 514/363; 514/364; 514/365; 514/372; 514/403; 514/444; 514/469; 544/237; 544/238; 544/253; 544/333; 544/353; 546/122; 546/134; 546/209; 546/241; 548/127; 548/128; 548/131; 548/134; 548/136; 548/143; 548/146; 548/229; 548/240; 548/250; 548/255; 548/262.2; 548/300.1; 548/364.1

(58) Field of Search ................. 514/252, 255, 514/256, 311, 326, 331, 333, 340, 365, 372, 376, 403, 444, 469; 544/237, 238, 253, 333, 353; 546/122, 134, 209, 241

(56) References Cited

U.S. PATENT DOCUMENTS

| | | | |
|---|---|---|---|
| 4,287,351 A | 9/1981 | Bourgery et al. | 548/232 |
| 4,346,102 A | 8/1982 | Langlois et al. | 424/279 |
| 4,476,136 A | 10/1984 | Dostert et al. | 424/272 |
| 4,705,799 A | 11/1987 | Gregory | 514/376 |
| 4,942,183 A | 7/1990 | Gregory et al. | 514/376 |

(List continued on next page.)

FOREIGN PATENT DOCUMENTS

| | | | |
|---|---|---|---|
| AU | 24985/95 | 2/1996 | C07J/1/00 |
| AU | 50735/96 | 10/1996 | C07D/413/10 |
| CA | 2154024 | 1/1996 | C07D/413/04 |
| EP | 0127902 | 12/1984 | |
| EP | 0184170 | 6/1986 | |

(List continued on next page.)

OTHER PUBLICATIONS

Abstracts: The 1996 ICAAC (Interscience Congress of Antimicrobial Agents and Chemotherapy), New Orleans, 41, 52, 140 (Sep. 1996).

(List continued on next page.)

Primary Examiner—Bruck Kifle
Assistant Examiner—Tamthom N. Truong
(74) Attorney, Agent, or Firm—Ropes & Gray

(57) ABSTRACT

The invention concerns a compound of the formula (I):

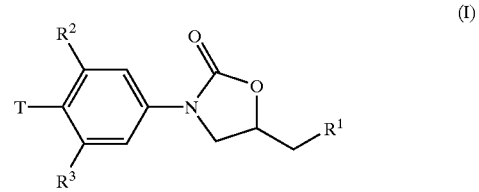

wherein, for example:

T is of the formula (IA), (IB), or (IC);

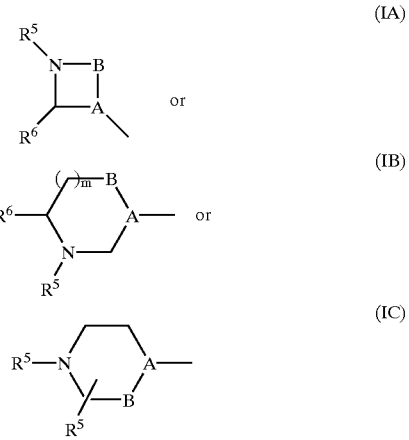

$R^1$ is of the formula —NHC(=O)$R^b$ wherein $R^b$ is (1–4C)alkyl;

$R^2$ and $R^3$ are hydrogen or fluoro;

>A—B— is >C=CH— (but not when T is (IA)) or >CH—CH$_2$—;

wherein when T is of the formula (IA) or (IB);

$R^6$ is, for example, (1–4C)alkyl; $R^5$ is hydrogen, $R^{10}$CO—, $R^{10}$SO$_2$— or $R^{10}$CS— wherein $R^{10}$ is, for example, optionally substituted phenyl, or (1–10C)alkyl, or when T is of the formula (IA), (IB); or (IC):

$R^5$ and $R^6$ are linked to give a 5- or 6-membered ring which is fused to the ring shown in (IA), (IB), or (IC) so as to give an optionally substituted bicyclic ring;

and pharmaceutically acceptable salts thereof, processes for their preparation, pharmaceutical compositions containing them, and their use as antibacterial agents.

13 Claims, No Drawings

U.S. PATENT DOCUMENTS

| | | | |
|---|---|---|---|
| 4,948,801 A | 8/1990 | Carlson et al. | 514/307 |
| 4,977,173 A | 12/1990 | Brittelli et al. | 514/376 |
| 5,043,443 A | 8/1991 | Carlson et al. | 544/112 |
| 5,164,510 A | 11/1992 | Brickner | 548/231 |
| 5,182,403 A | 1/1993 | Brickner | 548/231 |
| 5,231,188 A | 7/1993 | Brickner | 548/221 |
| 5,523,403 A | 6/1996 | Barbachyn | 544/137 |
| 5,529,998 A | 6/1996 | Habich et al. | 514/233.8 |
| 5,547,950 A | 8/1996 | Hutchinson et al. | 514/252 |
| 5,565,571 A | 10/1996 | Barbachyn et al. | 546/144 |
| 5,574,055 A | 11/1996 | Borgulya et al. | 514/376 |
| 5,627,181 A | 5/1997 | Riedl et al. | 514/236.8 |
| 5,652,238 A | 7/1997 | Brickner et al. | 514/235.8 |
| 5,654,528 A | 8/1997 | Tanaka | 544/235 |
| 5,668,286 A | 9/1997 | Yamada et al. | 546/209 |
| 5,684,023 A | 11/1997 | Riedl et al. | 514/337 |
| 5,688,792 A | 11/1997 | Barbachyn et al. | 514/235.5 |
| 5,698,574 A | 12/1997 | Riedl et al. | 514/376 |
| 5,708,169 A | 1/1998 | Hester, Jr. et al. | 549/152 |
| 5,719,154 A | 2/1998 | Tucker et al. | 514/252 |
| 5,736,545 A | 4/1998 | Gadwood et al. | 514/252 |
| 5,880,118 A | 3/1999 | Barbachyn et al. | 514/211 |
| 5,922,708 A | 7/1999 | Riedl et al. | 514/236.8 |
| 5,981,528 A | 11/1999 | Gravestock | 514/252 |
| 6,069,160 A | 5/2000 | Stolle et al. | 514/367 |

FOREIGN PATENT DOCUMENTS

| | | | |
|---|---|---|---|
| EP | 0312000 | 4/1989 | |
| EP | 0316594 | 5/1989 | |
| EP | 0352781 | 1/1990 | |
| EP | 0359418 | 3/1990 | |
| EP | 0609905 | 8/1994 | |
| EP | 0657440 | 6/1995 | C07D/263/24 |
| EP | 0693491 | 1/1996 | C07D/413/04 |
| EP | 0694543 | 1/1996 | C07D/413/04 |
| EP | 0694544 | 1/1996 | C07D/413/04 |
| EP | 0738726 | 10/1996 | C07D/417/04 |
| EP | 0789026 | 8/1997 | C07D/413/14 |
| FR | 2588547 | 1/1981 | C07D/263/16 |
| FR | 2500450 | 8/1982 | C07D/263/20 |
| GB | 2028306 | 3/1980 | |
| GB | 2053196 | 2/1981 | |
| GB | 2054575 B | 2/1981 | |
| GB | 2094299 | 9/1982 | |
| GB | 2141716 B | 1/1985 | |
| WO | WO 93/09103 | 5/1993 | |
| WO | WO 93/23384 | 11/1993 | |
| WO | WO 94/01110 | 1/1994 | |
| WO | WO 94/13649 | 6/1994 | |
| WO | WO 95/07271 | 3/1995 | |
| WO | WO 95/14684 | 6/1995 | |
| WO | WO 95/25106 | 9/1995 | |
| WO | WO 96/13502 | 5/1996 | |
| WO | WO 96/15130 | 5/1996 | |
| WO | WO 96/23788 | 8/1996 | |
| WO | WO 96/35691 | 11/1996 | |
| WO | WO 97/09328 | 3/1997 | |
| WO | WO 97/10223 | 3/1997 | |
| WO | WO 97/10235 | 3/1997 | |
| WO | WO 97/14690 | 4/1997 | |
| WO | WO 97/19089 | 5/1997 | |
| WO | WO 97/21708 | 6/1997 | |
| WO | WO 97/27188 | 7/1997 | |
| WO | WO 97/30981 | 8/1997 | |
| WO | WO 97/30995 | 8/1997 | |
| WO | WO 97/31917 A | 9/1997 | |
| WO | WO 97/37980 | 10/1997 | |
| WO | WO 97/43280 | 11/1997 | |
| WO | WO 98/01446 | 1/1998 | |
| WO | WO 98/01447 | 1/1998 | |
| WO | WO 98/07708 | 2/1998 | |

OTHER PUBLICATIONS

Ashtekar, D. et al. Oxazolidinones, a New Class of Synthetic Antituberculosis Agent: Invitro and in vivo Activities of Dup–721 Against Mycobacterium tuberculosis. *Diagn. Microbiol. Infect. Dis.* 14, 465–471 (1991).

Barbachyn, M. et al. Identification of a Novel Oxazolidinone (U–100480) with Potent Antimycobacterial Activity. *J. Med. Chem.* 39, 680–685 (1996).

Barbachyn, M. et al. Synthesis and Antibacterial Activity of New Tropone–Substituted Phenyloxazolidinone Antibacterial Agents. 1. Identification of Leads and Importance of the Tropone Substitution Pattern. *Bioorganic and Medicinal Chem. Letters* 6, 1003–1008 (1996).

Barbachyn, M. et al. Synthesis and Antibacterial Activity of New Tropone–Substituted Phenyloxazolidinone Antibacterial Agents. 2. Modification of the Pheny Ring—the Potentiating Effect of Fluorine Substitution on In Vivo Activity. *Bioorganic and Medicinal Chem. Letters* 6, 1009–1014 (1996).

Barry, A. et al. In Vitro Evaluation on Dup 105 and Dup 721, Two New Oxazolidinone Antimicrobial Agents. *Antimicrobial Agents and Chemotherapy* 32, 150–152 (1988).

Borthwick, A. et al. 5–(AcetamidomethyL)–3–Aryldihydrofuran–2–ones, and 5–(Acetamidomethyl)–3–Aryltetrahydrofuran–2–ones, Two New Classes of Antibacterial Agents. *Med. Chem. Res.* 6, 22–27 (1996).

Brickner, S. et al. Oxazolidinone Antibacterial Agents. *Current Pharmaceutical Design* 2, 175–194 (1996).

brickner, et al. Synthesis and Antibacterial Activity of U–100592 and U–100766, Two Oxazolidinone Antibacterial Agents for the Potential Treatment of Multidrug–Resistant Gram–Positive Bacterial Infections. *J. Med. Chem.* 39, 673–679 (1996).

Brumfitt, W. et al. Antibacterial Oxazolidinones: In Vitro Activity of a New Analogue, E33709. *diagn. Microbiol. Infect. Dis.* 15, 621–625 (1992).

Brumfitt, W. et al. In–vitro Microbiological Activities of Dup 105 and Dup 721, Novel Synthetic Oxazolidinones. *J. Antimicrobial Chemotherapy* 21, 711–720 (1988).

Brumfitt, W. et al. Variation in Response of Gram–Positive cocci to the Combination Dup 721 and ciprofloxacin. *J. Antimicrob. chemotherapy* 24, 465–466 (1989).

Daly, J. et al. Activity and Mechanism of Action of Dup 105 and Dup 721, New Oxazolidinone Compounds. *J. Antimicrobial Chemotherapy* 21, 721–730 (1988).

Denis, A. et al. 5–Aryl–beta, gamma Butenolide, A New Class of Antibacterial Derived from the N–Aryl Oxazolidinone Dup 721. *Bioorganic and Med. Chem Letters* 4, 1925–1930 (1994).

Dostert, P. et al. Structural Modifications in Oxazolidinone Series Leading to Type A or B Selective Monoamine Oxidase Inhibitors. *Int. Congress Series, Excerpta Medica* 564, 197–208 (1982).

Eliopoulos, G. et al. In Vitro Activities of New Oxazolidinone Antimicrobial Agents against Enterococci. *Antimicrobial Agents and Chemotherapy* 3240. 1745–1747 (1996).

Eustice, D. et al. An Automated Pulse labeling Method for Structure–Activity Relationship Studies with Antibacterial Oxazolidinones. *Drugs Exp. Clin. Res.* 16, 149–155 (1990).

Eustice, D. et al. Mechanism of Action of Dup 721: Inhibition of an Early Event during Initiation of Protein Synthesis. *Antimicrobial Agents and Chemotherapy* 32, 1218–1222 (1988).

Eustice, D. et al. The Mechanism of Action of Dup 721, a New Antibacterial Agent: Effects on Macromolecular Synthesis. *Biochem. And Biophys. Res. Comm.* 150, 965–971 (1988).

Ford, C. et al. In Vivo Activities of U–100592 and U–100766, Novel Oxazolidinone Antimicrobial Agents, against Experimental Bacterial Infections. *Antimicrobial Agents and Chemotherapy* 40, 1508–1513 (1996).

Grega, K. et al. Regioselective Metalation of Fluoroanilines. An Application to the Synthesis of Fluorinated Oxazolidinone Antibacterial Agents. *J. Org. Chem.* 60, 5255–5261 (1995).

Gregory, W. et al. Antibacterials. Synthesis and Structure–Activity Studies of 3–Aryl–2– Oxazolidinones. 1. The "B" Group. *J. Med. Chem.* 32, 1673–1681 (1989).

Gregory, W. et al. Antibacterials. Synthesis and Structure–Activity Studies of 3–Aryl–2–oxooxazolidines. 2. The "A" Group. *J. Med. Chem.* 33, 2569–2578 (1990).

Hutchinson, D. et al. Piperazinyl Oxazolidinones: Structure Activity Relationship of a New Class of Oxazolidinone Antibacterial Agents. *Interscience Congress of Antimicrobial Agents and Chemotherapy* Abstract 8–14 (Sep. 1995).

Jones, R. et al. In Vitro Antimicrobial Activities and Spectra of U–100592 and U–100766, Two Novel Fluorinated Oxazolidinones. *Antimicrobial Agents and Chemotherapy* 40, 720–726 (1996).

Jorgensen, J. et al. In Vitro Activities of the Oxazolidinone Antibodies U–100592 and U–100766 against *Staphylococcus aureus* and Coagulse Negative Staphylococcus Species. *Antimicrobial Agents and Chemotheraphy* 41, 465–467 (Feb. 1997).

Kaatz, G. et al. In Vitro Activities of Oxazolidinone Compounds U100592 and U100766 against *Staphylococcus aureus* and *Staphylococcus epidermis. Antimicrobial Agents and Chemotherapy* 40, 799–801 (1996).

Lin, A. et al. The Oxazolidinone Eperezolid Binds to the 50S Ribosomal Subunit and Competes with Binding of Chloramphenical and Lincomycin. *Antimicrobial Agents and Chemotherapy* 41, 2127–2131 (1997).

Linzondo, J. et al. Linezolid U–100766. *Drugs of the Future* 21, 1116–1123 (1996).

Lund, J. et al. Hypersegmented Megakaryocytes and Megakaryocytes with Multiple Separate Nuclei in Dogs Treated with PNU–100592, and Oxazolidinone Antibiotic. *Toxicologic Pathology* 25, 339–343 (1997).

Maple, P. et al. Comparative in–vitro activity of vancomycin, teicoplanin, ramoplanin (formerly A16686), paldimycin, Dup 721 and Dup 105 against methicillin and gentamicin resistant *Staphylococcus Aureus. J. Antimicrobial Chemotherapy* 23, 517–525 (1989).

Mason, E. et al. In Vitro Activities of Oxazolidinones U–100592 and U–100766 against Penicillin–Resistant and Cephalosporin–Resistant *Strains of Streptococcus pneumoniae. Antimicrobial Agents and Chemotherapy* 40, 1039–1040 (1996).

Mini, E. et al. Comparative in Vitro Activity of the New Oxazolidinones Dup 721 and Dup 105 against Staphylococci and Streptococci. *Eur. J. Clin. Microbiol. Infect. Dis.* 8, 256–260 (1989).

Mulazimoglu, L. et al. In Vitro Activities of Two Novel Oxazolidinones (U100592 and U100766), a New Fluoroquinolone (Trovafloxacin), and Dalfopristin–Quinupristin against *Staphylococcus aureus* and *Staphylococcus epidermis. Antimicrobial Agents and Chemotherapy* 40, 2428–2430 (1996).

Neu, H. et al., In Vitro Activities of Two Oxazolindinone Antimicrobial Agents, Dup 721 and Dup 105. *Antimicrobial Agents and Chemotherapy* 32, 580–583 (1988).

Park, C. et al. Antibacterials. Synthesis and Structure–Activity Studies of 3–Aryl–2– Oxazolidinones. 4. Multiply–Substituted Aryl Derivatives. *J. Med. Chem.* 35, 1156–1165 (1992).

Ranaldi, G. et al. Transport of the Antibacterial Agent Oxazolidin–2–One and Derivatives across Intestinal (Caco–2) and Renal (MDCK) Epithelial Cell Lines. *Antimicrobial Agents and Chemotherapy* 40, 652–658 (1996).

Schaadt, R. et al. Serum Inhibitory Titers and Serum Bactericidal Titers for Human Subjects Receiving Multiple Doses of the Antibacterial Oxazolidinones Eperzolid and Linezolid. *Microbiol. Infect. Dis.* 28, 201–204 (1997).

Schaus, S. et al. Dynamic Kinetic Resolution of Epichlorohydrin via Enantioselective Catalytic Ring Operation with TMSN3. Practical Synthesis of Aryl Oxazolidinone Antibacterial Agents. *Tetrahedron Letters* 37, 7937–7940 (1996).

Scholl, J. et al. Micellar Electrokinetic Chromatography as a Generalized Alternative to High–Performance Liquid Chromatography for Purity Determination of a Class of Investigational Antibacterial Drugs. *J. Chromatography* 695, 147–156 (1997).

Seneci, P. et al. Synthesis and Antimicrobial Activity of Oxazolidin–2–ones and Related Heterocycles. *J. Chem. Soc. Perkin Trans.* 1, 16, 2345–2351 (1994).

Shinabarger, D. et al. Mechanism of Action of Oxazolidinones: Effects of Linezolid and Eperezolid on Translation Reactions. *Antimicrobial Agents and Chemotherapy* 41, 2132–2136 (1997).

Silverman, R. et al. The Oxazolidinone Antibacterial Agent DuP 105 Does Not Act on Cell Wall Biosynthesis or on a Beta–Lactamase. *Biochemical and Biophys. Res. Comm.* 195, 1077–1080 (1993).

Slee, A. et al. Oxazolidinones, a New Class of Synthetic Antibacterial Agents: In Vitro and In Vivo Activities of DuP 105 and DuP 721. *Antimicrobial Agents and Chemotherapy* 31, 1791–1797 (1987).

Spangler, S. et al. Activities of RPR 106972 (a New Oral Streptogramin), Cefditoren (a New Oral Cephalosporin), Two New Oxazolidinones (U–100592 and U–100766), and Other Oral and Parenteral Agents against 203 Penicillin–Susceptible and—Resistant Pneumococci. *Antimicrobial Agents and Chemotherapy* 40, 481–484 (1996).

Takagi, H. et al. Safety Pharmacology Evaluation of the Oxazolidinone, U–100766. *Society of Toxicologists Annual Meeting*—Abstract 110, (1996).

Trucker, J. A. et al. Piperazinyl Oxazolidinone Antibacterial Agents Containing a Pyridine, Diazene, or Triazene Heteroaromatic Ring. *J. Med. Chem.* 41, 3727–2735 (1998).

Wang, C. et al. Chiral Synthesis fo DuP 721, a New Antibacterial Agent. *Tetrahedron* 45, 1323–1326 (1989).

Worth, S. et al. Quality Control Guidelines for Amoxicillin, Amoxicillin–Clavulanate, Azithromycin, Piperacillin–Tazobactam, Roxithromycin, Ticarcillin–Clavulanate, Trovafloxacin (CP 99,219), U–100592, and &–100766 for Various National Committee . . . *Diagn. Microbiol. Infect. Dis.* 24, 87–91 (1996).

Zurenko, G. et al. In Vitro Activities of U–100592 and U–100766, Novel Oxazolidinone Antibacterial Agents. *Antimicrobial Agents and Chemotherapy* 40, 839–845 (1996).

Zurenko, G et al. Oxazolidinone antibacterial agents: Development of the Clinical Candidates Eperezolid and Linezolid. *Exp. Opin. Invest. Drugs* 6, 151–158 (1997).

ANTIBIOTIC OXAZOLIDINONE DERIVATIVES

The present invention relates to antibiotic compounds and in particular to antibiotic compounds containing an oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci. Streptococci and mycobacteria, are particularly important because of the development of resistant strains which are both difficult to treat and difficult to eradicate from the hospital environment once established. Examples of such strains are methicillin resistant staphylococcus (MRSA). methicillin resistant coagulase negative staphylococci (MRCNS), penicillin resistant streptococcus pneumoniae and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

The present inventor has discovered a class of antibiotic compounds containing an oxazolidinone ring which has useful activity against Gram-positive pathogens including MRSA and MRCNS and, in particular, against various strains exhibiting resistance to vancomycin and against *E. faecium* strains resistant to both aminoglycosides and clinically used β-lactams.

We have now discovered a narrow range of compounds that is not suggested by the art and which has good activity against a broad range of Gram-positive pathogens including organisms known to be resistant to most commonly used antibiotics. In comparison with compounds described in the art (Walter A. Gregory et al in J.Med.Chem. 1990, 33, 2569–2578 and Chung-Ho Park et al in J.Med.Chem. 1992, 35, 1156–1165) the compounds also possess a favourable toxicological profile.

Accordingly the present invention provides a compound of the formula (I):

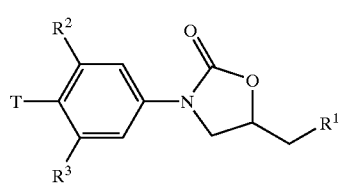

wherein:

T is of the formula (IA), (IB) or (IC);

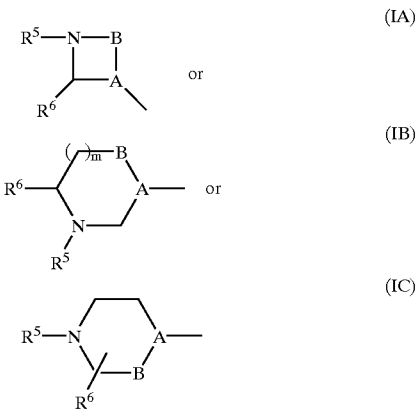

(wherein the $R^6$ group in (IC) may be in the 2- or 6-position relative to the ring nitrogen atom);

$R^1$ is chloro, fluoro, (1–4C)alkanesulfonyloxy, azido, (1–4C)alkoxy, (1–4C)alkylthio, (1–4C)alkylaminocarbonyloxy;

or of the formula —NHC(=O)$R^b$ wherein $R^b$ is hydrogen, (1–4C)alkoxy, amino, chloromethyl, dichloromethyl, cyanomethyl, methoxymethyl, acetylmethyl, methylamino, dimethylamino or (1–4C)alkyl; or of the formula —NHS(O)$_n$(1–4C)alkyl wherein n is 0, 1 or 2;

$R^2$ and $R^3$ are independently hydrogen or fluoro;

>A—B— is >C=CH—, >C($R^4$)—CH$_2$—, >CH—CH$_2$—, >C=C($R^{4a}$)—, >C($R^4$)—, CH($R^{4a}$)— or >CH—CH($R^{4a}$)—(wherein, herein and hereinafter, >represents two single bonds), provided that >A—B— is not >C=CH—, >C=C($R^{4a}$)—, >C($R^4$)— or >CH—CH($R^{4a}$)— when T is of the formula (IA); wherein $R^4$ is hydrogen, hydroxy, halo, (1–4C)alkyl or (1–4C)alkanoyloxy;

$R^{4a}$ is (1–4C)alkyl; m is 0 or 1;

wherein when T is of the formula (IA) or (IB);

$R^6$ is (1–4C)alkyl, (1–4C)alkanoylamino-(1–4C)alkyl, hydroxy-(1–4C)alkyl, carboxy, (1–4C)alkoxycarbonyl, AR-oxymethyl, AR-thiomethyl (wherein AR is as defined hereinbelow) or independently as defined for $R^5$ hereinbelow (excluding $R^5$ as hydrogen);

$R^5$ is hydrogen, cyano, 2-((1–4C)alkoxycarbonyl)ethenyl, 2-cyanoethenyl, 2-cyano-2-((1–4C)alkyl)ethenyl, 2-((1–4C)alkylaminocarbonyl)ethenyl, trityl or AR (as defined hereinbelow);

or $R^5$ is of the formula $R^{10}$CO—, $R^{10}$SO$_2$— or $R^{10}$CS— wherein $R^{10}$ is AR (as defined hereinbelow), cyclopentyl or cyclohexyl (wherein the last two-mentioned cycloalkyl rings are optionally mono- or disubstituted by substituents independently selected from (1–4C)alkyl (including geminal disubstitution), hydroxy, (1–4C)alkoxy, (1–4C)alkylthio, acetamido, (1–4C)alkanoyl, cyano and trifluoromethyl), benzyloxy, (1–4C)alkoxycarbonyl, hydrogen, amino, trifluoromethyl, (1–4C)alkylamino, di((1–4C)alkyl)amino, 2-(2-furyl)ethenyl, 2-(2-thienyl)ethenyl, 2-phenylethenyl (wherein the phenyl substituent is optionally substituted by up to three substituents independently selected from (1–4C)alkoxy halo and cyano), benzopyranone or (1–10C)alkyl [wherein (1–10C)alkyl is optionally substituted by hydroxy, benzyloxy, cyano, halo, (1–10C)alkoxy, trifluoromethyl, (1–4C)alkoxy-(1–4C)alkoxy, (1–4C)alkoxy-(1–4C)alkoxy-(1–4C)alkoxy, (1–4C)alkanoyl, (1–4C)alkoxycarbonyl, amino, (1–4C)alkylamino, di((1–4C)alkyl)amino, (1–6C)alkanoylamino, (1–4C)alkoxycarbonylamino, N-(1–4C)alkyl-N-(2–6C)alkanoylamino, (1–4C)alkylS(O)$_p$NH—, (1–4C)alkylS(O)$_p$((1–4C)alkyl)N—, fluoro(1–4C)alkylS(O)$_p$NH—, fluoro(1–4C)alkylS(O)$_p$((1–4C)alkyl)N—, phosphono, (1–4C)alkoxy(hydroxy)phosphoryl, di-(1–4C)alkoxyphosphoryl, (1–4C)alkylS(O)$_q$—, phenylS(O)$_q$—(wherein the phenyl group is optionally substituted by up to three substituents independently selected from (1–4C)alkoxy, halo and cyano), or CY (as defined hereinbelow), wherein p is 1 or 2 and q is 0, 1 or 2];

or $R^{10}$ of the formula $R^{11}C(O)O(1-6C)$alkyl wherein $R^{11}$ is an optionally substituted 5- or 6-membered heteroaryl, optionally substituted phenyl, (1–4C)alkylamino, benzyloxy-(1–4C)alkyl or optionally substituted (1–10C)alkyl, or $R^{10}$ is of the formula $R^{12}O$— wherein $R^{12}$ is optionally substituted (1–6C)alkyl;

or $R^5$ is of the formula $R^d$ OC($R^c$)=CH(C=O)—, $R^fC(=O)C(=O)$—, $R^gN=C(R^h)C(=O)$— or $R^iNHC(R^j)=CHC(=O)$— wherein $R^d$ is (1–6C)alkyl, $R^e$ is hydrogen or (1–6C)alkyl, or $R^d$ and $R^e$ together form a (3–4C)alkylene chain, $R_f$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C)alkoxy, (1–6C)alkoxy(1–6C)alkoxy, hydroxy(2–6C)alkoxy, (1–4C)alkylamino(2–6C)alkoxy), di-(1–4C)alkylamino(2–6C)alkoxy, $R^g$ is (1–6C)alkyl, hydroxy or (1–6C)alkoxy, $R^h$ is hydrogen or (1–6C)alkyl, $R^i$ is hydrogen, (1–6C)alkyl, optionally substituted phenyl or an optionally substituted 5- or 6-membered heteroaryl and $R^j$ is hydrogen or (1–6C)alkyl;

or $R^5$ is of the formula $R^{14}CH(R^{13})(CH_2)_m$— wherein m is 0 or 1, $R_{13}$ is fluoro, cyano, (1–4C)alkoxy, (1–4C)alkylsulfonyl, (1–4C)alkoxycarbonyl or hydroxy, (provided that when m is 0, $R^{13}$ is not fluoro or hydroxy) and $R^{14}$ is hydrogen or (1–4C)alkyl;

or when T is of the formula (IA), (IB) or (IC) $R^5$ is ethenyl, 2-(AR)ethenyl, 2-(1–4C)alkylethenyl or of the formula (ID)

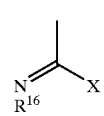

(ID)

wherein X is —OR$^{15}$, —SR$^{15}$, —NHR$_{15}$ and —N(R$^{15}$)$_2$ wherein R$^{15}$ is hydrogen (when X is —NHR$^{15}$ and —N(R$^{15}$)$_2$), (1–4C)alkyl or AR (as defined hereinbelow, when X is —OR$^{15}$, —SR$^{15}$ and —NHR$^{15}$); and R$^{16}$ is cyano, nitro, (1–4C)alkylsulfonyl, (4–10C)cycloalkylsulfonyl, phenylsulfonyl, (1–4C)alkanoyl and (1–4C)alkoxycarbonyl;

or when T is of the formula (IA), (IB) or (IC);

$R^5$ and $R^6$ are linked to give a group of the formula (IE) to (IT) [in which the N-atom shown is linked to $R^5$ in (IA) to (IC), and the adjacent carbon atom shown in (IE) to (IT) is linked to $R^6$ in (IA) to (IC)] so that a 5- or 6-membered ring is formed which is fused to the ring shown in (IA), (IB) or (IC) so as to give a bicyclic ring structure:

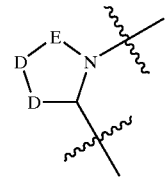

(IE)

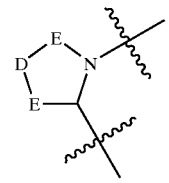

(IF)

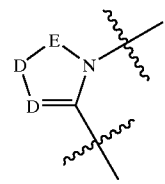

(IG)

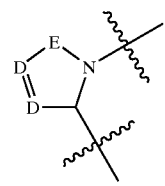

(IH)

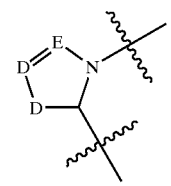

(IJ)

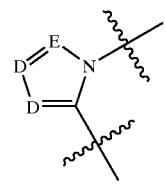

(IK)

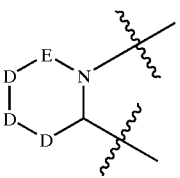

(IL)

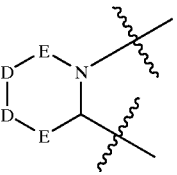

(IM)

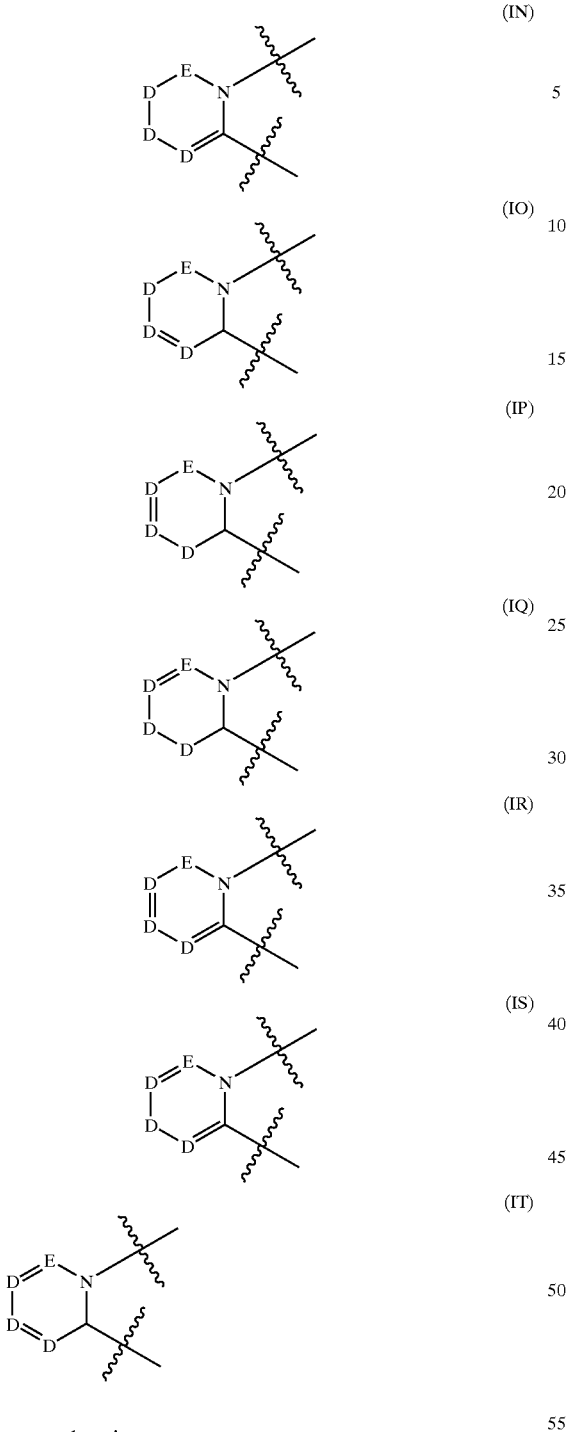

wherein
D is independently selected from >C(R⁷)(R⁸) [or =C(R⁸)— when D is connected to a carbon-carbon double bond, wherein = represents a carbon-carbon double bond], S(O)$_p$ [wherein p is 0, 1 or 2] and —O— [when D is not connected to a carbon-carbon double bond] and —NR⁹ [or N when D is connected to a carbon-carbon double bond);

E is independently selected from >C(R⁷)(R⁸) [or =C(R⁸)— when E is connected to a carbon-carbon double bond], S(O)$_p$ [wherein p is 0, 1 or 2] and >C=O [when E is not connected to a carbon-carbon double bond];

wherein R⁷ and R⁸ are independently selected from hydrogen, (1–4C)alkyl, (optionally substituted by hydroxy, trifluoromethyl, (1–4C) alkyl S(O)$_q$— (wherein q is 0, 1 or 2), (1–4C) alkoxy, carboxy, (1–4C)alkoxycarbonyl, carbamoyl, N-(1–4C)alkylcarbamoyl, di(N-(1–4C)alkyl)carbamoyl, cyano, nitro, amino, N-(1–4C)alkylamino, di(N-(1–4C)alkyl)amino or (1–4C) alkanoylamino), hydroxy [when D and E are not connected to a carbon-carbon double bond], (1–4C)alkoxy, halo, trifluoromethyl, thiol, (1–4C)alkylS(O)$_q$ (wherein q is 0, 1 or 2), carboxy, (1–4C)alkoxycarbonyl, (1–4C) alkanoyl, carbamoyl, N-(1–4C) alkylcarbamoyl, di(N-(1–4C)alkyl)carbamoyl, (2–4C)alkenyl (optionally substituted by carboxy or (1–4C)alkoxycarbonyl), cyano, (1–4C)alkanoylamino, amino, N-(1–4C) alkylamino, di(N-(1–4C)alkyl)amino or nitro;

wherein R⁹ is hydrogen, AR, trifluoromethyl, hydroxy, cyano, ethenyl), 2-(AR)ethenyl, 2-(1–4C)alkylethenyl, 2-((1–4C) alkoxycarbonyl)ethenyl, 2-cyanoethenyl, 2-cyano-2-((1–4C)alkyl)ethenyl, 2-((1–4C) alkylaminocarbonyl)ethenyl, benzopyranone or (1–10C)alkyl [wherein (1–10C)alkyl is optionally substituted by hydroxy, halo (provided that (1–10C)alkyl is not methyl when substituted by hydroxy or halo), cyano, (1–10C)alkoxy, trifluoromethyl, (1–4C) alkoxy-(1–4C)alkoxy, (1–4C)alkoxy-(1–4C) alkoxy-(1–4C)alkoxy, (1–4C)alkanoyl, (1–4C) alkoxycarbonyl, amino, (1–4C)alkylamino, di((1–4C)alkyl)amino, (1–6C)alkanoylamino, (1–4C)alkoxycarbonylamino, N-(1–4C)alkyl-N-(2–6C)alkanoylamino, (1–4C)alkylS(O)$_p$NH—, (1–4C)alkylS(O)$_p$((1–4C)alkyl)N—, fluoro(1–4C)alkylS(O)$_p$NH—, fluoro(1–4C) alkylS(O)$_p$((1–4C)alkyl)N—, phosphono, (1–4C)alkoxy(hydroxy)phosphoryl, di-(1–4C) alkoxyphosphoryl, (1–4C)alkylS(O)$_q$—, phenylS(O)$_q$—(wherein the phenyl group is optionally substituted by up to three substituents independently selected from (1–4C) alkoxy, halo and cyano), AR or CY (as defined hereinbelow), wherein p is 1 or 2 and q is 0, 1 or 2];

or R⁹ is of the formula R₁₁C(O)O(1–6C)alkyl wherein R¹¹ is an optionally substituted 5- or 6-membered heteroaryl, optionally substituted phenyl, (1–4C)alkylamino. benzyloxy-(1–4C) alkyl or optionally substituted (1–10C)alkyl;

or R⁹ is of the formula R¹²O— wherein R¹² is optionally substituted (1–6C)alkyl;

wherein AR is optionally substituted phenyl, phenylcarbonyl (when in AR-oxymethyl), optionally substituted phenyl(1–4C)alkyl, optionally substituted 5- or 6-membered heteroaryl, optionally substituted naphthyl or an optionally substituted 5/6 or 6/6 bicyclic heteroaryl ring system, in which the bicyclic heteroaryl ring systems may be linked via an atom in either of the rings comprising the bicyclic system, and wherein the mono- and bicyclic heteroaryl ring systems are linked via a ring carbon atom;
wherein CY is a 4-, 5- or 6-membered cycloalkyl ring, or a 5- or 6-membered cycloalkenyl ring; wherein any of the afore-mentioned ring systems in CY may be optionally substituted by up to three substituents independently selected from halo, (1–4C)alkyl (including geminal disubstitution when CY is a cycloalkyl or cycloalkenyl ring), acyl, oxo and nitro-(1–4C)alkyl;

or a pharmaceutically-acceptable salt thereof

In this specification a '5- or 6-membered heteroaryl' and 'heteroaryl (monocyclic) ring' means a 5- or 6-membered aryl ring wherein 1, 2 or 3 of the ring atoms are selected from nitrogen, oxygen and sulfur. Particular examples of 5- or 6-membered heteroaryl ring systems are furan (preferably 2-furyl when AR in 2-(AR)ethenyl), pyrrole, pyrazole, imidazole, triazole, pyrimidine (preferably pyrimidin-2-yl), pyridaziie, pyridine (preferably pyrid-2-yl), isoxazole, oxazole, isothiazole, thiazole and thiophene (preferably 2-thienyl when AR in 2-(AR)ethenyl).

In this specification a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Particular examples of 5/6 and 6/6 bicyclic ring systems are indole, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

In this specification a '4-, 5- or 6-membered cycloalkyl ring' means a cyclobutyl, cyclopentyl or cyclohexyl ring; and a '5- or 6-membered cycloalkenyl ring' a means cyclpentenyl or cyclohexenyl ring.

In this specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C)alkyl includes 1-bromoethyl and 2-bromoethyl.

Particular optional substituents for alkyl, phenyl (and phenyl containing moieties) and naphthyl groups and ring carbon atoms in heteroaryl (mono or bicyclic) rings in $R^{11}$, $R^{12}$, $R^1$ and AR include halo, (1–4C)alkyl, hydroxy, nitro, carbamoyl, (1–4C)alkylcarbarnoyl, di-((1–4C)alkyl)carbamoyl, cyano, trifluoromethyl, trifluoromethoxy, amino, (1–4C)alkylamino, di((1–4C)alkyl)amino, (1–4C)alkylS(O)$_q$—, (wherein q is 0, 1 or 2), carboxy, (1–4C)alkoxycarbonyl, (2–4C)alkenyl, (2–4C)alkynyl (1–4C)alkanoyl, (1–4C)alkoxy, (1–4C)alkanoylamino, benzoylamino, benzoyl, phenyl (optionally substituted by up to three substituents selected from halo, (1 –4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, hydroxy-(1–4C)alkyl, halo-(1–4C)alkyl, nitro(1–4C)alkyl, amino(1–4C)alkyl, cyano(1–4C)alkyl, (1–4C)alkanesulfonamido, aminosulfonyl, (1–4C)alkylaminosulfonyl and di-((1–4C)alkyl)aminosulfonyl. The phenyl and naphthyl groups and heteroaryl (mono- or bicyclic) rings in $R^{11}$, $R^i$ and AR may be mono- or disubstituted on ring carbon atoms with substituents independently selected from the above list of particular optional substituents.

Particular optional substituents for ring nitrogen atoms in heteroaryl groups in $R^{11}$, $R^{12}$, $R^i$ and AR and in the nitrogen-containing rings in CY, which can be substituted without becoming quaternised include (1–4C)alkyl, (2–4C)alkenyl, (2–4C)alkynyl and (1–4C)alkanoyl.

Examples of halo groups include fluoro, chloro and bromo; examples of (1–4C)alkyl, include methyl, ethyl, and propyl and isopropyl; examples of (1–6C)alkyl include methyl, ethyl, propyl, isopropyl, pentyl and hexyl; examples of (1–10C)alkyl include methyl, ethyl, propyl, isopropyl, pentyl, hexyl, heptyl, octyl and nonyl; examples of (1–4C)alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of (1–4C)alkylS(O)$_q$— wherein q is 0, 1 or 2 include methylthio, ethylthio, methylsulfinyl, ethylsulfinyl, methylsulifonyl and ethylsulfonyl; examples of (1–4C)alkanesulfonyloxy include methylsulfonyloxy, ethylsulfonyloxy and propylsulfonyloxy; examples of (1–4C)alkylthio include methylthio and ethylthio; examples of (1–4C)alkylsulfonyl include methylsulfonyl and ethylsulfonyl; examples of (1–4C)alkylaminocarbonyloxy include methylaminocarbonyloxy and ethylaminocarbonyloxy; examples of (1–4C)alkanoylamino-(1–4C)alkyl include formamidomethyl, acetamidomethyl and acetamidoethyl; examples of (1–6C)alkoxy-(1–6C)alkyl include methoxymethyl, ethoxymethyl and 2-methoxyethyl; examples of (1–4C)alkoxycarbonyl include methoxycarbonyl, ethoxycarbonyl and propoxycarbonyl; examples of (1–4C)alkanoyloxy include acetyloxy and propionyloxy; examples of (1–4C)alkoxy include methoxy, ethoxy, propoxy and tert-butoxy; examples of (1–6C)alkoxy and (1–10C)alkoxy include methoxy, ethoxy, propoxy, tert-butoxy and pentoxy, examples of hydroxy-(2–6C)alkoxy include 2-hydroxyethoxy and 3-hydroxypropoxy: examples of (1–4C)alkylamino-(2–6C)alkoxy include 2-methylaminoethoxy and 2-ethylaminoethoxy; examples of di-(1–4C)alkylamino-(2–6C)alkoxy include 2-dimethylaminoethoxy and 2-diethylaminoethoxy; examples of (1–4C)alkoxy-(1–4C)alkoxy and (1–6C)alkoxy-(1–6C)alkoxy include methoxymethoxy, 2-methoxyethoxy, 2-ethoxyethoxy and 3-methoxypropoxy; examples of (1–4C)alkoxy-(1–4C)alkoxy-(1–4C)alkoxy include 2-(methoxymethoxy)ethoxy, 2-(2-methoxyethoxy)ethoxy; 3-(2-methoxyethoxy)propoxy and 2-(2-ethoxyethoxy)ethoxy; examples of (1–4C)alkanoylamino and (1–6C)alkanoylamino include formamido, acetamido and propionylamino: examples of (1–4C)alkoxycarbonylamino include methoxycarbonylamino and ethoxycarbonylamino; examples of N-(1–4C)alkyl-N-(2–6C)alkanoylamino include N-methylacetamido, N-ethylacetamido and N-methylpropionamido; examples of (1–4C)alkylS(O)$_p$NH— wherein p is 1 or 2 include methylsulfinylamino, methylsulfonylamino, ethylsulfinylamino and ethylsulfonylamino; examples of (1–4C)alkylS(O)$_p$((1–4C)alkyl)NH— wherein p is 1 or 2 include methylsulfinylmethylamino, methylsulfonylmethylamino, 2-(ethylsulfinyl)ethylamino and 2-(ethylsulfonyl)ethylamino; examples of fluoro(1–4C)alkylS(O)$_p$NH— wherein p is 1 or 2 include trifluoromethylsulfinylamino and trifluoromethylsulfonylamino; examples of fluoro(1–4C)alkylS(O)$_p$((1–4C)alkyl)NH— wherein p is 1 or 2 include trifluoromethylsulfinylmethylamino and trifluoromethylsulfonylmethylamino examples of (1–4C)alkoxy(hydroxy) phosphoryl include methoxy(hydroxy)phosphoryl and ethoxy(hydroxy)phosphoryl; examples of di-(1–4C) alkoxyphosphoryl include di-methoxyphosphoryl, di-ethoxyphosphoryl and ethoxy(methoxy)phosphoryl; examples of 2-(1–4C)alkylethenyl include 2-methylethenyl and 2-ethylethenyl; examples of 2-((1–4C)alkoxycarbonyl) ethenyl include 2-(methoxycarbonyl)ethenyl and 2-(ethoxycarbonyl)ethenyl; examples of 2-cyano-2-((1–4C) alkyl)ethenyl include 2-cyano-2-methylethenyl and 2-cyano-2-ethylethenyl; examples of 2-((1–4C) alkylaminocarbonyl)ethenyl include 2-(methylaminocarbonyl)ethenyl and 2-(ethylaminocarbonyl)ethenyl; examples of benzyloxy(1–4C)alkyl include benzyloxymethyl and benzyloxyethyl; examples of phenyl(1–4C)alkyl include benzyl and phenethyl; examples of phenylS(O)$_q$ wherein q is 0, 1 or 2 are phenylthio, phenylsulfinyl and phenylsulfonyl respectively; examples of (1–4C) alkylcarbamoyl include methylcarbamoyl and ethylcarbamoyl; examples of di((1–4C)alkyl)carbamoyl include di(methyl)carbamoyl and di(ethyl)carbamoyl; examples of a (3–4C)alkylene chain are trimethylene or tetramethylene; examples of (2–4C)alkenyl include allyl and vinyl, examples of (2–4C)alkynyl include ethynyl and 2-propynyl; examples of (1–4C)alkanoyl include formyl, acetyl and propionyl; examples of hydroxyimino(1–4C)alkyl include hydroxyiminomethyl, 2-(hydroxyimino)ethyl and 1-(hydroxyimino)ethyl; examples of (1–4C)alkoxyimino-(1–4C)alkyl include methoxyiminomethyl, ethoxyiminomethyl, 1-(methoxyimino)ethyl and 2-(methoxyimino)ethyl; examples of hydroxy(1–4C)alkyl and hydroxy(1–6C)alkyl include hydroxymethyl, 1-hydroxyethyl, 2-hydroxyethyl and 3-hydroxypropyl; examples of halo(1–4C)alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C) alkyl include aminomethyl, 1-aminoethyl, 2-aminoethyl and 3-aminopropyl; examples of cyano(1–4C)alkyl include cyanomethyl, 1-cyanoethyl, 2-cyanoethyl and 3-cyanopropyl; examples of (1–4C)alkanesulfonamido include methanesulfonamido and ethanesulfonamido; examples of (1–4C)alkylaminosulfonyl include methylaminosulfonyl and ethylaminosulfonyl; examples of di-(1–4C) alkylaminosulfonyl include dimethylaminosulfonyl, diethylaminosulfonyl and N-methyl-N-ethylaminosulfonyl; and examples of (4–10C)cycloalkylsulfonyl include cyclopentylsulfonyl and cyclohexylsulfonyl.

Suitable pharmaceutically-acceptable salts include acid addition salts such as methanesulfonate, fumarate, hydrochloride, hydrobromide, citrate, maleate and salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). Examples of pro-drugs include in-vivo hydrolysable esters of a compound of the formula (I).

An in-vivo hydrolysable ester of a compound of the formula (I) containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C) cycloalkoxycarbonyloxy(1–6C)alkyl esters for example 1-cyclohexylcarbonyloxyethyl; 1,3-dioxolen-2-onylmethyl esters for example 5-methyl-1,3-dioxolen-2-onylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the formula (I) containing a hydroxy group includes inorganic esters such as phosphate esters and α-acyloxyalkyl ethers and related compounds which as a result of the in-vivo hydrolysis of the ester breakdown to give the parent hydroxy group. Examples of (x-acyloxyalkyl ethers include acetoxymethoxy and 2,2-dimethylpropionyloxymethoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4- position of the benzoyl ring.

The compounds of the present invention have a chiral centre at the C-5 position of the oxazolidinone ring. The pharmaceutically active enantiomer is of the formula:

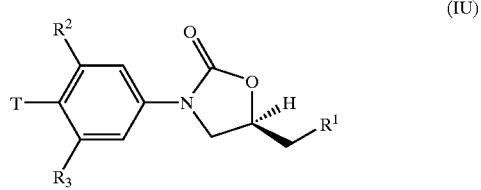

(IU)

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. For the avoidance of doubt the enantiomer depicted above could be either 5R or 5S depending upon the value of $R^1$. For example, when $R^1$ is acetamido, the enantiomer depicted above is the 5S enantiomer.

Furthermore, some compounds of the formula (I) may have other chiral centres, and some compounds of the formula (I) may exist as one or more regioisomers. It is to be understood that the invention encompasses all such optical, diastereo- and regio-isomers that possess antibacterial activity.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

Particularly preferred compounds of the invention comprise a compound of the formula (I), or a pharmaceutically-acceptable salt thereof, wherein the substituents T, >A—B—, $R^1$ to $R^{16}$ and other optional substituents mentioned above have the values disclosed hereinbefore, or any of the following values:

(a) Preferably $R^1$ is of the formula —NHC(=O)$R^a$ wherein $R_a$ is hydrogen, methoxy, chloromethyl, dichloromethyl, cyanomethyl, methoxymethyl, acetyimethyl, methylamino, dimethylamino or (1–4C)alkyl.

(b) Yet more preferably $R^1$ is of the formula —NHC(=O)(1–4C)alkyl.

(c) Most preferably $R^1$ is acetamido.

(d) Preferably, $R^2$ and $R^3$ are hydrogen.

(e) More preferably one of $R^2$ and $R^3$ is hydrogen and the other is fluoro.

(f) In another aspect both $R^2$ and $R^3$ are fluoro.

(g) Preferably T is of the formula (IB) or (IC).

(h) More preferably T is of the formula (IB) wherein m is 0.

(i) Preferably $R^6$ is (1–4C)alkyl, hydroxy-(1–4C)alkyl, AR-oxymethyl and Ar-thiomethyl.

Especially preferred is AR when it is optionally substituted phenyl, phenyl(1–4C)alkyl, naphthyl, furan, pyrrole, pyrazole, imidazole, triazole, pyrimidine, pyridazine, pyridine, isoxazole, oxazole, isothiazole, thiazole or thiophene.

(j) When T is of the formula (IA), (IB) or (IC) and $R^5$ and $R^6$ are linked to give a group of the formula (IE) to (IT) so that a 5- or 6-membered ring is formed which is fused to the ring shown in (IA), (IB) or (IC) to give a bicyclic ring structure, T is preferably of the formula (IA) and (IB) wherein m is 0, >A—B— is preferably of the formula >CH—CH$_2$ or >C($R^4$)CH$_2$— (wherein $R^4$ is preferably methyl) (when T is of the formula (IA)) and >C=CH— (when T is of the formula (IB)), and $R^5$ and $R^6$ are preferably linked to give a group of the formula (IE) to (IK). Thus, when $R^5$ and $R^6$ are linked, 5/4- and 5/5- membered bicyclic rings are preferably formed.

(k) When T is of the formula (IA), (IB) or (IC) and $R^5$ and $R^6$ are linked to give a group of the formula (IL) to (IT) so that a 6-membered ring is formed which is fused to the ring shown in (IA), (IB) or (IC) to give a bicyclic ring structure, T is preferably of the formula (IA) and (IB) wherein m is 0, >A—B— is preferably of the formula >CH—CH$_2$ or >C($R^4$)CH$_2$— (wherein $R^4$ is preferably methyl) (when T is of the formula (IA)) and >C=CH— (when T is of the formula (IB)), and $R^5$ and $R^6$ are preferably linked to give a group of the formula (IR) or (IS).

(l) When T is of the formula (IA), (IB) or (IC) and $R^5$ and $R^6$ are linked to give a group of the formula (IE) to (IT, D is preferably >C($R^7$)($R^8$) (wherein $R^7$ and $R^8$ are preferably hydrogen), —O— or —N$R^9$ (wherein $R^9$ is preferably (1–10C)alkyl or phenyl) and E is preferably >C=O.

(m) Preferably >A—B— is of the formula >C=CH— when T is of the formula (IB) and (IC).

(n) Preferably >A—B— is of the formula >C($R^4$)CH$_2$— when T is of the formula (IA), and $R^4$ is preferably methyl.

(o) When T is of the formula (IA), (IB) and (IC) $R^5$ is preferably hydrogen, cyano, AR, $R^{10}$CO— or $R^{10}$SO$_2$— wherein $R_{10}$ is preferably hydrogen or (1–10C)alkyl (optionally substituted by hydroxy, (1–10C)alkoxy, (1–4C)alkanoyl and (1–4C)alkoxycarbonyl).

(p) When T is of the formula (IA), (IB) and (IC) $R^5$ is preferably hydrogen, cyano, benzyl, pyrimidyl, imidazolyl, triazolyl, methoxycarbonyl, tert-butoxycarbonyl, hydoxyacetyl, acetyloxymethylcarbonyl, methoxyacetyl, methoxalyl, or methanesulfonyl.

(q) Preferred substituents for phenyl and carbon atoms in heteroaryl (mono- and bicyclic) ring systems include halo, (1–4C)alkyl, hydroxy, nitro, amino, cyano, (1–4C)alkylS(O)$_p$— and (1–4C)alkoxy.

(r) Preferred optional substituents for (1–10C)alkyl in $R^{11}$ are hydroxy, cyano, amino, (1–4C)alkylamino, di((1–4C)alkyl)amino, (1–4C)alkylS(O)$_p$ (wherein p is 1 or 2), carboxy, (1–4C)alkoxycarbonyl, (1–4C)alkoxy, piperazino or morpholino.

(s) Preferred optional substituents for (1–6C)alkyl in $R^{12}$ are hydroxy, (1–4C)alkoxy, cyano, amino, (1–4C)alkylamino, di(1–2C)alkylamino, (1–4C)alkylS(O)$_p$— (wherein p is 1 or 2), (t) Preferably the ring systems in AR are unsubstituted.

(u) Preferably the 5/6 and 6/6 bicyclic ring systems in AR are unsubstituted.

(v) Preferably the 5- or 6-membered heteroaryl rings in AR, $R^1$ and $R^{11}$ are unsubstituted.

(w) Preferably the 5- or 6-membered heteroaryl in $R^{11}$ is pyridyl or imidazol-1-yl.

(x) Preferably $R^{12}$ is (1–6C)alkyl. Most preferably $R^{12}$ is tert-butyl or methyl.

(y) Preferably $R^{13}$ is cyano or fluoro.

(z) Preferably $R^{14}$ is hydrogen.

(a1) Preferably CY is naphthoxy, especially naphth-1-oxy or naphth-2-oxy.

(b1) Especially preferred is AR when it is optionally substituted phenyl, phenyl(1–4C)alkyl, naphthyl, furan, pyrrole, pyrazole, imidazole, triazole, pyrimidine, pyridazine, pyridine, isoxazole, oxazole, isothiazole, thiazole or thiophene.

Therefore, an especially preferred compound of the present invention is of the formula (IU) wherein $R^1$ is acetamido, one of $R^2$ and $R^3$ is hydrogen and the other is fluoro, T is of the formula (IB) (wherein m is 0), >A—B— is of the formula >C=CH—, $R^6$ is (1–4C)alkyl, hydroxy-(1–4C)alkyl, AR-oxymethyl and Ar-thiomethyl, $R^5$ is hydrogen, cyano, AR, $R^{10}$CO— or $R^{10}$SO$_2$— wherein $R^{10}$ is preferably hydrogen or (1–10C)alkyl (optionally substituted by hydroxy, (1–10C)alkoxy, (1–4C)alkanoyl and (1–4C)alkoxycarbonyl), or a pharmaceutically-acceptable salt thereof.

A further especially preferred compound of the present invention is of the formula (IU) wherein $R^1$ is acetamido, one of $R^2$ and $R^3$ is hydrogen and the other is fluoro, T is of the formula (IB) (wherein m is 0), >A—B— is of the formula >C=CH—, $R^6$ is benzyloxycarbonyl, (1–4C)alkoxycarbonyl, hydroxy-(1–4C)alkyl, AR-oxymethyl (especially benzoyloxymethyl) and Ar-thiomethyl (especially pyrimidin-2-ylthiomethyl), $R^5$ is hydrogen, trityl, cyano, acetoxyacetyl, (1–6C)alkoxycarbonyl, AR (especially pyrimidin-2-yl), $R^{10}$OCO— or $R^{10}$SO$_2$— wherein $R^{10}$ is preferably hydrogen or (1–10C)alkyl (optionally substituted by benzyloxy or hydroxy), or a pharmaceutically-acceptable salt thereof.

A further especially preferred compound of the present invention is of the formula (IU) wherein $R^1$ is acetamido, one of $R^2$ and $R^3$ is hydrogen and the other is fluoro, T is of the formula (IA) and (IB) (wherein mn is 0), >A—B— is of the formula >C=CH$_2$ or >C($R^4$)CH$_2$— (wherein $R^4$ is preferably methyl) (when T is of the formula (IA)) and >C=CH— (when T is of the formula (IB)), and $R^5$ and $R^6$ are linked to give a group of the formula (IE) to (IK) so that a 5-membered ring is formed which is fused to the ring shown in (IA) or (IB) to give a 5/4- and 5/5-bicyclic ring structure, or a pharmaceutically-acceptable salt thereof.

A further especially preferred compound of the present invention is of the formula (IU) wherein $R_1$ is acetamido, one of $R^2$ and $R^3$ is hydrogen and the other is fluoro, T is of the formula (IB) (wherein m is 0), >A—B— is of the formula >C=CH—, and $R^5$ and $R^6$ are linked to give a group of the formula (IE) to (IK) so that a 5-membered ring is formed which is fused to the ring shown in (IB) to give a 5/5- bicyclic ring structure, or a pharmaceutically-acceptable salt thereof. Particularly preferred 5/5- bicyclic ring structures are dihydropyrrolo[1,2c]oxazole and 1,2,3,7a-tetrahydropyrrolo[1,2c]imidazole, especially with an oxo substituent on the carbon atom between the two heteroatoms.

In further aspects there are provided any of the above especially preferred compounds, or a pharmaceutically-acceptable salt thereof, wherein both $R^2$ and $R^3$ are hydrogen, or both are fluoro, or $R^2$ and $R^3$ are independently hydrogen or fluoro.

Particular compounds of the present invention are:

N-((5S)-3-(4-(2S-benzyloxycarbonyl-1-trityl-2,5-dihydropyrrol-4-yl)phenyl)-2-oxooxazolidin-5-ylmethyl)acetamide;

N-((5S)-3-(4-(2S-benzyloxycarbonyl-2,5-dihydropyrrol-4-yl)phenyl)-2-oxooxazolidin-5-ylmethyl)acetamide;

N-((5S)-3-(4-(1-benzyloxymethylcarbonyl-2S-benzyloxycarbonyl-2,5-dihydropyrrol-4-yl)phenyl)-2-oxooxazolidin-5-ylmethyl)acetamide;

N-((5S)-3-(4-(1-acetoxyacetyl-S-benzyloxycarbonyl-2,5-dihydropyrrol-4-yl)phenyl)-2-oxooxazolidin-5-ylmethyl)acetamide;

N-((5S)-3-(4-(1-methylsulphonyl-2S-benzyloxycarbonyl-2,5-dihydropyrrol-4-yl)phenyl)-2-oxooxazolidin-5-ylmethyl)acetamide;

N-((5S )-3-(4-(1-cyano-2S-benzyloxycarbonyl-2,5-dihydropyrrol-4-yl)phenyl)-2-oxooxazolidin-5-ylmethyl)acetamide;

N-((5S)-3-(4-(1-formyl-2S-benzyloxycarbonyl-2,5-dihydropyrrol-4-yl)phenyl)-2-oxooxazolidin-5-ylmethyl)acetamide;

N-((5S)-3-(4-(1-hydroxyacetyl-2S-benzyloxycarbonyl-2,5-dihydropyrrol-4-yl)phenyl)-2oxooxazolidin-5-ylmethyl)acetamide;

N-((5S)-3-(4-(1-(pyrimidin-2-yl)-2S-ethoxycarbonyl-2,5-dihydropyrrol-4-yl)phenyl)-2-oxooxazolidin-5-ylmethyl)acetamide;

N-((5S)-3-(4-(2S-ethoxycarbonyl-2,5-dihydropyrrol-4-yl)phenyl)-2-oxooxazolidin-5-ylmethyl)acetamide;

N-((5S)-3-(4-(2S-hydroxymethyl-1-trityl-2,5-dihydropyrrol-4-yl)phenyl)-2-oxooxazolidin-5-ylmethyl)acetamide;

N-((5S)-3-(4-(2S-(pyrimidin-2-yl)thiomethyl-1-trityl-2,5-dihydropyrrol-4-yl)phenyl)-2-oxooxazolidin-5-ylmethyl)acetamide;

N-((5S)-3-(4-(1-formyl-2S-(pyrimidin-2-yl)thiomethyl-2,5-dihydropyrrol-4-yl)phenyl)-2-oxooxazolidin-5-ylmethyl)acetamide;

N-((5S)-3-(4-(1-cyano-2S-(pyrimidin-2-yl)thiomethyl-2,5-dihydropyrrol-4-yl)phenyl)-2-oxooxazolidin-5-ylmethyl)acetamide;

N-((5S)-3-(4-(1-acetoxyacetyl-2S-(pyrimidin-2-yl) thiomethyl-2,5-dihydropyrrol-4-yl)phenyl)-2-oxooxazolidin-5-ylmethyl)acetamide;

N-((5S)-3-(4-(1-tert-Butoxycarbonyl-2S-tert-butyldimethylsilyloxymethyl-2,5-dihydropyrrol-4-yl) phenyl)-2-oxooxazolidin-5-ylmethyl)acetamide;

N-((5S)-3-(3-fluoro-4-(1-tert-Butoxycarbonyl-2S-tert-butyldimethylsilyloxymethyl-2,5-dihydropyrrol-4-yl) phenyl)-2-oxooxazolidin-5-ylmethyl)acetamide;

N-((5S)-3-(4-(1-tert-Butoxycarbonyl-2S-hydroxymethyl-2,5-dihydropyrrol-4-yl)phenyl)-2-oxooxazolidin-5-ylmethyl)acetamide;

N-((5S)-3-(4-(1-tert-Butoxycarbonyl-2S-tert-butyldiphenylsilyloxymethyl-2,5-dihydropyrrol-4-yl) phenyl)-2-oxooxazolidin-5-ylmethyl)acetamide;

N-((5S)-3-(4-(1-tert-Butoxycarbonyl-2S-benzoyloxymethyl-2,5-dihydropyrrol-4-yl)phenyl)-2-oxooxazolidin-5-ylmethyl)acetamide;

N-((5S)-3-(4-(2S-benzoyloxymethyl-2,5-dihydropyrrol-4-yl)phenyl)-2-oxooxazolidin-5-ylmethyl)acetamide, N-((5S)-3-(4-(2S-benzoyloxymethyl-1-cyano-2,5-dihydropyrrol-4-yl )phenyl)-2-oxooxazolidin-5-ylmethyl)acetamide, N-((5S)-3-(4-(2S-benzoyloxymethy-1-1-formyl-2,5-dihydropyrrol-4-yl)phenyl)-2-oxooxazolidin-5-ylmethyl)acetamide;

N-((5S)-3-(4-(2S-hydroxymethyl-2,5-dihydropyrrol-4-yl)phenyl)-2-oxooxazolidin-5-ylmethyl)acetamide;

N-((5S)-3-(4-(1-formyl-2S-hydroxymethyl-2,5-dihydropyrrol-4-yl)phenyl)-2-oxooxazolidin-5-ylmethyl)acetamide;

N-((5S)-3-(4-(1-Benzyl-2RS-benzyloxymethyl-azetidin-3-y l)phenyl-2-oxooxazolidin-5-ylmethyl)acetamide; or a pharmaceutically-acceptable salt thereof.

Of the above particular compounds, the compounds of Examples 23, 24, 25, 32, 40 and 41 described hereinafter, or a pharmaceutically-acceptable salt thereof, are especially preferred.

Where a mixture of isomers is described the invention includes the mixture and the particular individual isomers.

For assistance in naming compounds containing a bicyclic ring the following parent ring structures are provided by way of example:

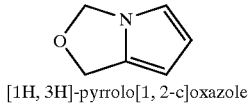 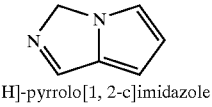

[1H, 3H]-pyrrolo[1, 2-c]oxazole     [3H]-pyrrolo[1, 2-c]imidazole

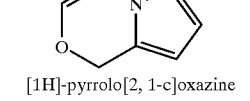 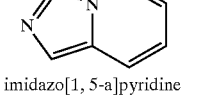

[1H]-pyrrolo[2, 1-c]oxazine     imidazo[1, 5-a]pyridine

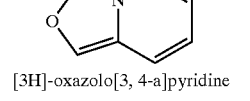 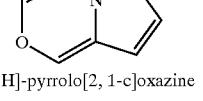

[3H]-oxazolo[3, 4-a]pyridine     [6H]-pyrrolo[2, 1-c]oxazine

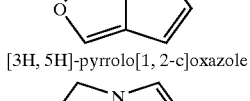 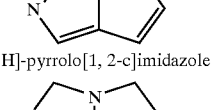

[3H, 5H]-pyrrolo[1, 2-c]oxazole     [5H]-pyrrolo[1, 2-c]imidazole

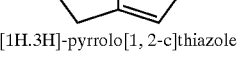 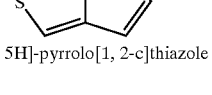

[1H.3H]-pyrrolo[1, 2-c]thiazole     [3H, 5H]-pyrrolo[1, 2-c]thiazole

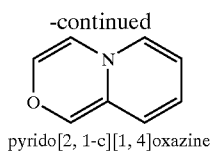

pyrido[2,1-c][1,4]oxazine

Further particular compounds of the present invention containing a bicyclic ring are:

N-((5S)-3-(4-(1,4-dioxo-1,3,4,6,9,9a-hexahydro-pyrido[2.1c][1,4]oxazin-8-yl)phenyl)-2-oxooxazolidin-5-ylmethyl)acetamide;

N-((5S)-3-(4-(1,3-dioxo-2-phenyl-1,2.3,5,8,8a-hexahydroimidazo[1,5a]pyridin-7-yl)phenyl)-2-oxooxazolidin-5-ylmethyl)acetamide;

N-((5S)-3-(4-(1,3-dioxo-2-ethyl-1,2,3,5,8,8a-hexahydroimidazo[1,5a]pyridin-7-yl)phenyl)-2-oxooxazolidin-5-ylmethyl)acetamide;

N-((5S)-3-(4-(3-oxo-1,5,8,8a-tetrahydrooxazolo[3,4a]pyridin-7-yl)phenyl)-2-oxooxazolidin-5-ylmethyl)acetamide;

N-((5S)-3-(4-(3-oxo-1,5,6,7,8,8a-hexahydrooxazolo[3,4a]pyridin-7-yl)phenyl)-2-oxooxazolidin-5-ylmethyl)acetamide;

N-((5S)-3-(4-((7aS)[3H,5H]-3-oxo-1,7a-dihydropyrrolo[1,2c]oxazol-6-yl)phenyl)-2-oxooxazolidin-5-ylmethyl)acetamide;

N-((5S)-3-(3-fluoro-4-((7aS)[3H,5H]-3-oxo-1,7a-dihydropyrrolo[1,2c]oxazol-6-yl)phenyl)-2-oxooxazolidin-5-ylmethyl)acetamide;

N-((5S)-3-(3,5-difluoro-4-((7aS)[3H,5H]-3-oxo-1,7a-dihydropyrrolo[1,2c]oxazol-6-yl)phenyl)-2-oxooxazolidin-5-ylmethyl)acetamide;

N-((5S)-3-(4-((7aS)[5H]-3-oxo-1,2,3,7a-tetrahydropyrrolo[1,2c]imidazol-6-yl)phenyl)-2-oxooxazolidin-5-ylmethyl)acetamide;

N-((5S)-3-(4-((7aR)[3H,5H]-3-oxo-1,7a-dihydropyrrolo[1,2c]oxazol-6-yl)phenyl)-2-oxooxazolidin-5-ylmethyl)acetamide;

N-((5S)-3-(4-([3H,5H]-3-oxo-pyrrolo[1,2-c]oxazol-6-yl)phenyl)-2-oxooxazolidin-5-ylmethyl)acetamide;

N-((5S)-3-(3-fluoro-4-([3H,5H]-3-oxo-pyrrolo[1,2-c]oxazol-6-yl)phenyl)-2-oxooxazolidin-5-ylmethyl)acetamide;

N-((5S)-3-(3,5-difluoro-4-([3H,5H]-3-oxo-pyrrolo[1,2-c]oxazol-6-yl)phenyl)-2-oxooxazolidin-5-ylmethyl)acetamide;

N-((5S)-3-(3-fluoro-4-([5H]-3-oxo-1,2,3,7a-tetrahydropyrrolo[1,2-c]imidazol-6-yl)phenyl)-2-oxooxazolidin-5-ylmethyl)acetamide;

N-((5S)-3-(3,5-difluoro-4-([5H]-3-oxo-1,2,3,7a-tetrahydropyrrolo[1,2-c3]imidazol-6-yl)phenyl)-2-oxooxazolidin-5-ylmethyl)acetamide;

N-((5S)-3-(4-([5H]-2-methyl-3-oxo-1,2,3,7a-tetrahydropyrrolo[1,2-c]imidazol-6-yl)phenyl)-2-oxooxazolidin-5-ylmethyl)acetamide;

N-((5S)-3-(3-fluoro-4-([5H]-2-methyl-3-oxo-1,2,3,7a-tetrahydropyrrolo[1,2-c]imidazol-6-yl)phenyl)-2-oxooxazolidin-5-ylmethyl)acetamide;

N-((5S)-3-(3,5-difluoro-4-([5H]-2-methyl-3-oxo-1,2,3,7a-tetrahydropyrrolo[1,2-c]imidazol-6-yl)phenyl)-2-oxooxazolidin-5-ylmethyl)acetamide;

N-((5S)-3-(4-([5H]-2-ethyl-3-oxo-1,2,3,7a-tetrahydropyrrolo[1,2-c]imidazol-6-yl)phenyl)-2-oxooxazolidin-5-ylmethyl)acetamide;

N-((5S)-3-(3-fluoro-4-([5H]-2-ethyl-3-oxo-1,2,3,7a-tetrahydropyrrolo[1,2-c]imidazol-6-yl)phenyl)-2-oxooxazolidin-5-ylmethyl)acetamide;

N-((5S)-3-(3,5-difluoro-4-([5H]-2-ethyl-3-oxo-1,2,3,7a-tetrahydropyrrolo[1,2-c]imidazol-6-yl)phenyl)-2-oxooxazolidin-5-ylmethyl)acetamide;

N-((5S)-3-(4-([5H]-3-oxo-2,3-dihydropyrrolo[1,2-c]imidazol-6-yl)phenyl)-2-oxooxazolidin-5-ylmethyl)acetamide;

N-((5S)-3-(3-fluoro-4-([5H]-3-oxo-2,3-dihydropyrrolo[1,2-c]imidazol-6-yl)phenyl)-2-oxooxazolidin-5-ylmethyl)acetamide;

N-((5S)-3-(3,5-difluoro-4-([5H]-3-oxo-2,3-dihydropyrrolo[1,2-c]imidazol-6-yl)phenyl)-2-oxooxazolidin-5-ylmethyl)acetamide;

N-((5S)-3-(4-([5H]-2-methyl-3-oxo-2,3-dihydropyrrolo[1,2-c]imidazol-6-yl)phenyl)-2-oxooxazolidin-5-ylmethyl)acetamide;

N-((5S)-3-(3-fluoro-4-([5H]-2-methyl-3-oxo-2,3-dihydropyrrolo[1,2-c]imidazol-6-yl)phenyl)-2-oxooxazolidin-5-ylmethyl)acetamide;

N-((5S)-3-(3,5-difluoro-4-([5H]-2-methyl-3-oxo-2,3-dihydropyrrolo[1,2-c]imidazol-6-yl)phenyl)-2-oxooxazolidin-5-ylmethyl)acetamide;

N-((5S)-3-(4-([5H]-2-ethyl-3-oxo-2,3-dihydropyrrolo[1,2-c]imidazol-6-yl)phenyl)-2-oxooxazolidin-5-ylmethyl)acetamide;

N-((5S)-3-(3-fluoro-4-([5H]-2-ethyl-3-oxo-2,3-dihydropyrrolo[1,2-c]imidazol-6-yl)phenyl)-2-oxooxazolidin-5-ylmethyl)acetamide;

N-((5S)-3-(3,5-difluoro-4-([5H]-2-ethyl-3-oxo-2,3-dihydropyrrolo[1,2-c]imidazol-6-yl)phenyl)-2-oxooxazolidin-5-ylmethyl)acetamide;

N-((5S)-3-(4-([5H]-2-hydroxy-3-oxo-1,2,3,7a-tetrahydropyrrolo[1,2-c]imidazol-6-yl)phenyl)-2-oxooxazolidin-5-ylmethyl)acetamide;

N-((5S)-3-(3-fluoro-4-([5H]-2-hydroxy-3-oxo-1,2,3,7a-tetrahydropyrrolo[1,2-c]imidazol-6-yl)phenyl)-2-oxooxazolidin-5-ylmethyl)acetamide;

N-((5S)-3-(3,5-difluoro-4-([5H]-2-hydroxy-3-oxo-1,2,3,7a-tetrahydropyrrolo[1,2-c]imidazol-6-yl)phenyl)-2-oxooxazolidin-5-ylmethyl)acetamide;

N-((5S)-3-(4-([5H]-2-hydroxy-3-oxo-2,3-dihydropyrrolo[1,2-c]imidazol-6-yl)phenyl)-2-oxooxazolidin-5-ylmethyl)acetamide;

N-((5S)-3-(3-fluoro-4-([5H]-2-hydroxy-3-oxo-2,3-dihydropyrrolo[1,2-c]imidazol-6-yl)phenyl)-2-oxooxazolidin-5-ylmethyl)acetamide;

N-((5S)-3-(3,5-difluoro-4-([5H]-2-hydroxy-3-oxo-2,3-dihydropyrrolo[1,2-c]imidazol-6-yl)phenyl)-2-oxooxazolidin-5-ylmethyl)acetamide;

N-((5S)-3-(4-([3H,5H]-3-oxo-pyrrolo[1,2-c]thiazol-6-yl)phenyl)-2-oxooxazolidin-5-ylmethyl)acetamide;

N-((5S)-3-(3-fluoro-4-([3H,5H]-3-oxo-pyrrolo[1,2c]thiazol-6-yl)phenyl)-2-oxooxazolidin-5-ylmethyl)acetamide;

N-((5S)-3-(3,5-difluoro-4-([3H,5H]-3-oxo-pyrrolo[1,2c]thiazol-6-yl)phenyl)-2-oxooxazolidin-5-ylmethyl)acetamide;

N-((5S)-3-(4-([3H,5H]-3-oxo-1,7a-dihydropyrrolo[1,2-c]thiazol-6-yl)phenyl)-2-oxooxazolidin-5-ylmethyl)acetamide;

N-((5S)-3-(3-fluoro-4-([3H,5H]-3-oxo-1,7a-dihydropyrrolo[1,2c]thiazol-6-yl)phenyl)-2-oxooxazolidin-5-ylmethyl)acetamide;

N-((5S)-3-(3,5-difluoro-4-([3H,5H]-3-oxo-1,7a-dihydropyrrolo[1,2c]thiazol-6-yl)phenyl)-2-oxooxazolidin-5-ylmethyl)acetamide;

N-((5S)-3-(4-([5H]-pyrrolo[1,2-c]imidazol-6-yl)phenyl)-2-oxooxazolidin-5-ylmethyl)acetamide;

N-((5S)-3-(3-fluoro-4-([5H]-pyrrolo[1,2-c]imidazol-6-yl)phenyl)-2-oxooxazolidin-5-ylmethyl)acetamide;

N-((5S)-3-(3,5-difluoro-4-([5H]-pyrrolo[1,2-c]imidazol-6-yl)phenyl)-2-oxooxazolidin-5-ylmethyl)acetamide;

N-((5S)-3-(4-(3-hydroxymethyl-[5H]-pyrrolo[1,2-c]imidazol-6-yl)phenyl)-2-oxooxazolidin-5-ylmethyl)acetamide;

N-((5S)-3-(3-fluoro-4-(3-hydroxymethyl-[5H]-pyrrolo[1,2-c]imidazol-6-yl)phenyl)-2-oxooxazolidin-5-ylmethyl)acetamide;

N-((5S)-3-(3,5-difluoro-4-(3-hydroxymethyl-[5H]-pyrrolo[1,2-c]imidazol-6-yl)phenyl)-2-oxooxazolidin-5-ylmethyl)acetamide;

N-((5S)-3-(4-(3-methyl-[5H]-pyrrolo[1,2-c]imidazol-6-yl)phenyl)-2-oxooxazolidin-5-ylmethyl)acetamide;

N-((5S)-3-(3-fluoro-4-(3-methyl-[5H]-pyrrolo[1,2-c]imidazol-6-yl)phenyl)-2-oxooxazolidin-5-ylmethyl)acetamide;

N-((5S)-3-(3,5-difluoro-4-(3-methyl-[5H]-pyrrolo[1,2-c]imidazol-6-yl)phenyl)-2-oxooxazolidin-5-ylmethyl)acetamide;

N-((5S)-3-(4-(1-hydroxymethyl-[5H]-pyrrolo[1,2-c]imidazol-6-yl)phenyl)-2-oxooxazolidin-5-ylmethyl)acetamide;

N-((5S)-3-(3-fluoro-4-(1-hydroxymethyl-[5H]-pyrrolo[1,2-c]imidazol-6-yl)phenyl)-2-oxooxazolidin-5-ylmethyl)acetamide;

N-((5S)-3-(3,5-difluoro-4-(1-hydroxymethyl-[5H]-pyrrolo[1,2-c]imidazol-6-yl)phenyl)-2-oxooxazolidin-5-ylmethyl)acetamide;

N-((5S)-3-(4-(1-methyl-[5H]-pyrrolo[1,2-c]imidazol-6-yl)phenyl)-2-oxooxazolidin-5-ylmethyl)acetamide;

N-((5S)-3-(3-fluoro-4-(1-methyl-[5H]-pyrrolo[1,2-c]imidazol-6-yl)phenyl)-2-oxooxazolidin-5-ylmethyl)acetamide;

N-((5S)-3-(3,5-difluoro-4-(1-methyl-[5H]-pyrrolo[1,2-c]imidazol-6-yl)phenyl)-2-oxooxazolidin-5-ylmethyl)acetamide;

N-((5S)-3-(4-(1-bromo-[5H]-pyrrolo[1,2-c]imidazol-6-yl)phenyl)-2-oxooxazolidin-5-ylmethyl)acetamide;

N-((5S)-3-(3-fluoro-4-(1-bromo-[5H]-pyrrolo[1,2-c]imidazol-6-yl)phenyl)-2-oxooxazolidin-5-ylmethyl)acetamide;

N-((5S)-3-(3,5-difluoro-4-(1-bromo-[5H]-pyrrolo[1,2-c]imidazol-6-yl)phenyl)-2-oxooxazolidin-5-ylmethyl)acetamide;

N-((5S)-3-(4-(1H)-3-oxo-3,4,8,8a-tetrahydropyrrolo[2,1-c]oxazin-7-yl)phenyl)-2-oxooxazolidin-5-ylmethyl)acetamide;

N-((5S)-3-(3-fluoro-4-([1H]-3-oxo-3,4,8,8a-tetrahydropyrrolo[2,1-c]oxazin-7-yl)phenyl)-2-oxooxazolidin-5-ylmethyl)acetamide;

N-((5S)-3-(3,5-difluoro-4-([1H]-3-oxo-3,4,8,8a-tetrahydropyrrolo[2,1-c]oxazin-7-yl)phenyl)-2-oxooxazolidin-5-ylmethyl)acetamide;

N-((5S)-3-(4-([3H]-3-oxo-1,5,8,8a-tetrahydrooxazolo[3,4-a]pyrid-7-yl)phenyl)-2-oxooxazolidin-5-ylmethyl)acetamide;

N-((5S)-3-(4-(3-fluoro-[3H]-3-oxo-1,5,8,8a-tetrahydrooxazolo[3,4-a]pyrid-7-yl)phenyl)-2-oxooxazolidin-5-ylmethyl)acetamide;

N-((5S)-3-(4-(3,5-difluoro-[3H]-3-oxo-1,5,8,8a-tetrahydrooxazolo[3,4-a]pyrid-7-yl)phenyl)-2-oxooxazolidin-5-ylmethyl)acetamide;

N-((5S)-3-(4-(1-hydroxymethyl-[3H]-3-oxo-1,5,8,8a-tetrahydrooxazolo[3,4-a]pyrid-7-yl)phenyl)-2-oxooxazolidin-5-ylmethyl)acetamide;

N-((5S)-3-(3-fluoro-4-(1-hydroxymethyl-[3H]-3-oxo-1,5,8,8a-tetrahydrooxazolo[3,4-a]pyrid-7-yl)phenyl)-2-oxooxazolidin-5-ylmethyl)acetamide;

N-((5S)-3-(3,5-difluoro-4-(1-hydroxymethyl-[3H]-3-oxo-1,5,8,8a-tetrahydrooxazolo-3,4-a]pyrid-7-yl)phenyl)-2-oxooxazolidin-5-ylmethyl)acetamide;

N-((5S)-3-(4-([3H]-3-oxo-5,8-dihydroxazolo[3,4-a]pyrid-7-yl)phenyl)-2-oxooxazolidin-5-ylmethyl)acetamide;

N-((5S)-3-(4-(3-fluoro-[3H]-3-oxo-5,8-dihydrooxazolo[3,4-a]pyrid-7-yl)phenyl)-2-oxooxazolidin-5-ylmethyl)acetamide;

N-((5S)-3-(4-(3,5-difluoro-[3H]-3-oxo-5,8-dihydrooxazolo[3,4-a]pyrid-7-yl)phenyl)-2-oxooxazolidin-5-ylmethyl)acetamide;

N-((5S)-3-(4-(1-hydroxymethyl-[3H]-3-oxo-5,8-dihydrooxazolo[3,4-a]pyrid-7-yl)phenyl)-2-oxooxazolidin-5-ylmethyl)acetamide;

N-((5S)-3-(3-fluoro-4-(1-hydroxymethyl-[3H]-3-oxo-5,8-dihydrooxazolo[3,4-a]pyrid-7-yl)phenyl)-2-oxooxazolidin-5-ylmethyl)acetamide;

N-((5S)-3-(3,5-difluoro-4-(1-hydroxymethyl-[3H]-3-oxo-5,8-dihydrooxazolo[3,4-a]pyrid-7-yl)phenyl)-2-oxooxazolidin-5-ylmethyl)acetamide;

N-((5S)-3-(4-(5,8-dihydroimidazo[1,5-a]pyrid-7-yl)phenyl)-2-oxooxazolidin-5-ylmethyl)acetamide;

N-((5S)-3-(3-fluoro-4-(5,8-dihydroimidazo[1,5-a]pyrid-7-yl)phenyl)-2-oxooxazolidin-5-ylmethyl)acetamide;

N-((5S)-3-(3,5-difluoro-4-(5,8-dihydroimidazo[1,5-a]pyrid-7-yl)phenyl)-2-oxooxazolidin-5-ylmethyl)acetamide;

N-((5S)-3-(4-(5,6-dihydroimidazo[1,5-a]pyrid-7-yl)phenyl)-2-oxooxazolidin-5-ylmethyl)acetamide;

N-((5S)-3-(3-fluoro-4-(5,6-dihydroimidazo[1,5-a]pyrid-7-yl)phenyl)-2-oxooxazolidin-5-ylmethyl)acetamide;

N-((5S)-3-(3,5-difluoro-4-(5,6-dihydroimidazo[1,5-a]pyrid-7-yl)phenyl)-2-oxooxazolidin-5-ylmethyl)acetamide;

N-((5S)-3-(4-(1-bromo-5,8-dihydroimidazo[1,5-a]pyrid-7-yl)phenyl)-2-oxooxazolidin-5-ylmethyl)acetamide;

N-((5S)-3-(3-fluoro-4-(1-bromo-5,8-dihydroimidazo[1,5-a]pyrid-7-yl)phenyl)-2-oxooxazolidin-5-ylmethyl)acetamide;

N-((5S)-3-(3,5-difluoro-4-(1-bromo-5,8-dihydroimidazo[1,5-a]pyrid-7-yl)phenyl)-2-oxooxazolidin-5-ylmethyl)acetamide;

N-((5S)-3-(4-(1-bromo-5,6-dihydroimidazo[1,5-a]pyrid-7-yl)phenyl)-2-oxooxazolidin-5-ylmethyl)acetamide;

N-((5S)-3-(3-fluoro-4-(1-bromo-5,6-dihydroimidazo[1,5-a]pyrid-7-yl)phenyl)-2-oxooxazolidin-5-ylmethyl)acetamide;

N-((5S)-3-(3,5-difluoro-4-(1-bromo-5,6-dihydroimidazo[1,5-a]pyrid-7-yl)phenyl)-2-oxooxazolidin-5-ylmethyl)acetamide;

N-((5S)-3-(4-(1-hydroxymethyl-5,8-dihydroimidazo[1,5-a]pyrid-7-yl)phenyl)-2-oxooxazolidin-5-ylmethyl)acetamide;

N-((5S)-3-(3-fluoro-4-(1-hydroxymethyl-5,8-dihydroimidazo[1,5-a]pyrid-7-yl)phenyl)-2-oxooxazolidin-5-ylmethyl)acetamide;

N-((5S)-3-(3,5-difluoro-4-(1-hydroxymethyl-5,8-dihydroimidazo[1,5-a]pyrid-7-yl)phenyl)-2-oxooxazolidin-5-ylmethyl)acetamide;

N-((5S)-3-(4-(3-hydroxymethyl-5,6-dihydroimidazo[1,5-a]pyrid-7-yl)phenyl)-2-oxooxazolidin-5-ylmethyl)acetamide;

N-((5S)-3-(3-fluoro-4-(3-hydroxymethyl-5,6-dihydroimidazo[1,5-a]pyrid-7-yl)phenyl)-2-oxooxazolidin-5-ylmethyl)acetamide;

N-((5S)-3-(3,5-difluoro-4-(3-hydroxymethyl-5,6-dihydroimidazo[1,5-a]pyrid-7-yl)phenyl)-2-oxooxazolidin-5-ylmethyl)acetamide;

N-((5S)-3-(4-(1-cyano-5,8-dihydroimidazo[1,5-a]pyrid-7-yl)phenyl)-2-oxooxazolidin-5-ylmethyl)acetamide;

N-((5S)-3-(3-fluoro-4-(1-cyano-5,8-dihydroimidazo[1,5-a]pyrid-7-yl)phenyl)-2-oxooxazolidin-5-ylmethyl)acetamide;

N-((5S)-3-(3,5-difluoro-4-(1-cyano-5,8-dihydroimidazo[1,5-a]pyrid-7-yl)phenyl)-2-oxooxazolidin-5-ylmethyl)acetamide;

N-((5S)-3-(4-(3-cyano-5,6-dihydroimidazo[1,5-a]pyrid-7-yl)phenyl)-2-oxooxazolidin-5-ylmethyl)acetamide;

N-((5S)-3-(3-fluoro-4-(3-cyano-5,6-dihydroimidazo[1,5-a]pyrid-7-yl)phenyl)-2-oxooxazolidin-5-ylmethyl)acetamide;

N-((5S)-3-(3,5-difluoro-4-(3-cyano-5,6-dihydroimidazo[1,5-a]pyrid-7-yl)phenyl)-2-oxooxazolidin-5-ylmethyl)acetamide;

N-((5S)-3-(4-(3-cyano-5,8-dihydroimidazo[1,5-a]pyrid-7-yl)phenyl)-2-oxooxazolidin-5-ylmethyl)acetamide;

N-((5S)-3-(3-fluoro-4-(3-cyano-5,8-dihydroimidazo[1,5-a]pyrid-7-yl)phenyl)-2-oxooxazolidin-5-ylmethyl)acetamide;

N-((5S)-3-(3,5-difluoro-4-(3-cyano-5,8-dihydroimidazo[1,5-a]pyrid-7-yl)phenyl)-2-oxooxazolidin-5-ylmethyl)acetamide;

N-((5S)-3-(4-(1-cyano-5,6-dihydroimidazo[1,5-a]pyrid-7-yl)phenyl)-2-oxooxazolidin-5-ylmethyl)acetamide;

N-((5S)-3-(3-fluoro-4-(1-cyano-5,6-dihydroimidazo[1,5-a]pyrid-7-yl)phenyl)-2-oxooxazolidin-5-ylmethyl)acetamide;

N-((5S)-3-(3,5-difluoro-4-(1-cyano-5,6-dihydroimidazo[1,5-a]pyrid-7-yl)phenyl)-2-oxooxazolidin-5-ylmethyl)acetamide; or a pharmaceutically-acceptable salts thereof.

Of the above particular compounds, the compounds of Examples 44, 45, 47, 48 and 49 described hereinafter are especially preferred.

Where a mixture of isomers is described, the invention includes the mixture and the particular individual isomers.

In a further aspect the present invention provides a process for preparing a compound of formula (I) or a pharmaceutically-acceptable salt thereof. The compounds of formula (I) may be prepared by deprotecting a compound of formula (II):

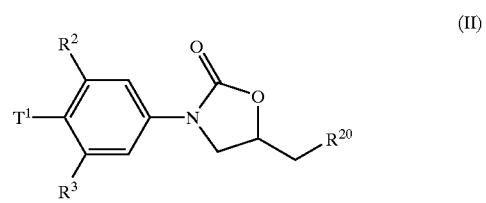

(II)

wherein $R^2$ and $R^3$ are as hereinabove defined, $R^{20}$ is $R^1$ or protected $R^1$ and $T^1$ is T in which functional groups are optionally protected; and thereafter, if necessary, forming a pharmaceutically-acceptable salt or in-vivo-hydrolysable ester.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience and are included as a further feature of the invention. "Lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl; lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl) silyl groups (eg trimethylsilyl and t-butyldimethylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkyl/arylsilyl groups (eg trimethylsilyl, t-butyldimethylsilyl, t-butyldiphenylsilyl); aryl lower alkyl groups (eg benzyl) groups; and triaryl lower alkyl groups (eg triphenylmethyl).

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl; trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, metal- or enzymically-catalysed hydrolysis, for groups such as o-nitrobenzyloxycarbonyl, photolytically and for groups such as silyl groups, fluoride. Benzyl protecting groups may be removed by use of a $BCl_3$—$Me_2S$ complex.

Examples of protecting groups for amide groups include aralkoxymethyl (eg. benzyloxymethyl and substituted benzyloxymethyl); alkoxymethyl (eg. methoxymethyl and trimethylsilylethoxymethyl); tri alkyl/arylsilyl (eg. trimethylsilyl, t-butyldimethylsily, t-butyldiphenylsilyl); tri alkyl/arylsilyloxymethyl (eg. t-butyldimethylsilyloxymethyl, t-butyldiphenylsilyloxymethyl); 4-alkoxyphenyl (eg. 4-methoxyphenyl); 2,4-di(alkoxy)phenyl (eg. 2,4-dimethoxyphenyl); 4-alkoxybenzyl (eg. 4-methoxybenzyl); 2,4-di(alkoxy)benzyl (eg. 2,4-di(methoxy)benzyl); and alk-1-enyl (eg. allyl, but-1-enyl and substituted vinyl eg. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyl groups may be introduced by reacting the amide with the appropriate chloride and removing with acid, or in the case of the silyl containing groups fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

For further examples of protecting groups see one of the many general texts on the subject, for example, 'Protective Groups in Organic Synthesis' by Theodora Green (publisher: John Wiley & Sons).

In another aspect of the present invention the compounds of the formulae (I) and (II); pharmaceutically acceptable salts thereof and in-vivo-hydrolysable esters thereof can be prepared by the following processes (a) to (o). Certain novel intermediates, for example compounds of the formula (I) or (II) wherein $R^1$ or $R^{10}$ is hydroxy and amino, and processes for their preparation, are provided as a further feature of the invention.

(a) by modifying a substituent in or introducing a substituent into another compound of formula (I) or (II);

(b) when $R^1$ or $R^{20}$ is of the formula —$NHS(O)_n$(1–4C)alkyl, wherein n is 1 or 2, by oxidising a compound of the formula (I) or (II) wherein n is 0 or, when n is 2 by oxidising a compound of the formula (I) or (II) wherein n is 1;

(c) when $R^1$ or $R^{20}$ is of the formula —$NHC(=O)R^b$ or —$NHS(O)_n$(1–4C)alkyl, introducing the group —$C(=O)R^b$ or —$S(O)_n$(1–4C)alkyl into a compound of the formula (III):

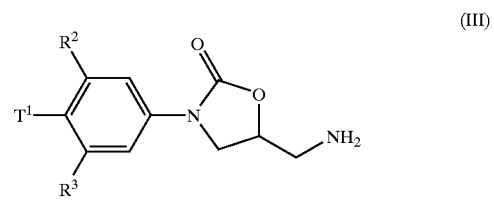

wherein a compound of the formula (III) (i.e. a compound of the formula (I) or (II) wherein $R^1$ or $R^{20}$ is amino) may be obtained by reducing a compound of the formula (I) or (II) wherein $R^1$ or $R^{20}$ is azido;

(d) when $R^1$ or $R^{20}$ is chloro, fluoro, (1–4C)alkanesulfonyloxy, or (1–4C)alkylaminocarbonyloxy, or $R^{20}$ is of the formula —$N(CO_2R^{26})CO(1$–$4C)alkyl$, wherein $R^{26}$ is (1–4C)alkyl or benzyl; from a compound of the formula (I) and (II) wherein $R^1$ or $R^{20}$ is hydroxy; wherein a compound of the formula (I) and (II) wherein $R^1$ or $R^{20}$ is hydroxy may be obtained by reacting a compound of the formula (V) with a compound of formula (VI):

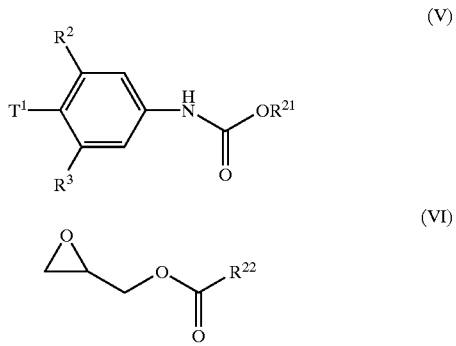

wherein $R^{21}$ is (1–6C)alkyl or benzyl; $R^{22}$ is of the formula (1–4C)alkyl or —$S(O)_n$(1–4C)alkyl;

(e) when T or $T^1$ is of the formula (IB) and (IC) and contains >A—B— of the formula >C=CH— or >C=C($R^{4a}$)—, by reacting (using Pd coupling chemistry) a compound of the formula (VII) with a compound of the formula (VIIA) or (VIIB) wherein >A—B— is of the formula >C=CH— or >C=C($R^{4a}$)—:

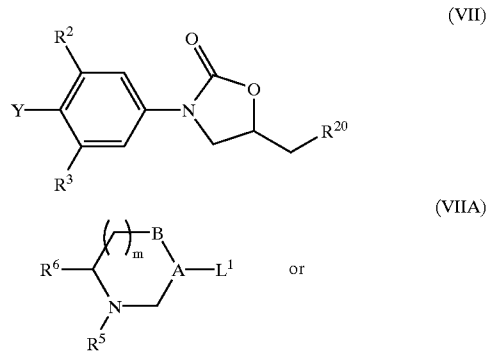

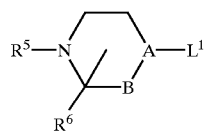

(VIIB)

wherein L¹ is an iodo or triflate leaving group (when Y is a trialkyltin residue or a boronate acid or ester residue) and L¹ is a trialkyltin residue or a boronate acid or ester residue (when Y is an iodo or triflate leaving group); Y is an iodo or triflate leaving group (when L¹ is a trialkyltin residue or a boronate acid or ester residue) and Y is a trialkyltin residue or a boronate acid or ester residue (when L¹ is an iodo or triflate leaving group);

(f) when T or T¹ contains >A—B— of the formula >CH—CH₂— or >CH—CH(R⁴ᵃ)—, by catalytic hydrogenation of a compound of the formula (I) or (II) wherein >A—B— is >C=CH— or >C=C(R⁴ᵃ)—;

(g) when T or T¹ contains >A—B— of the formula >C=CH— or >C=C(R⁴ᵃ), by elimination of the elements of water, or HOCOR²³, or HOSO₂R²⁴ from a compound in which >A—B— is of the formula >C(OH)—CH₂—, >C(OCOR²³)—CH₂—, >C(OSO₂R²⁴)—CH₂—, >C(OH)—CH(R⁴ᵃ)—, >C(OCOR²³)—CH(R⁴ᵃ)— or >C(OSO₂R²⁴)—CH(R⁴ᵃ)—; wherein R²³ is (1–4C)alkyl and R²⁴ is an optionally substituted phenyl group;

(h) when T or T¹ is of the formula (IA) or (IB) and contains >NR⁵ where R⁵ is R¹⁰CO—, R¹⁰SO₂— or R¹⁰CS— and R⁵ is not linked to R₆, by reaction, of a compound of formula (II) in which T or T¹ is of the formula (IA) or (IB) and contains >NR⁵ wherein R⁵ is hydrogen, with a compound of the formula R¹⁰COL², R¹⁰SO₂L² or R¹⁰CSL²; wherein L² is a leaving group (such as, for example, hydroxy or chloro); and when R⁵ is R¹⁰CO— and R¹⁰ is amino, (1–4C)alkylamino or di-(1–4C)alkylamino, by reaction with an appropriate isocyanate in an inert solvent (at, or near, ambient temperature);

(i) when R¹ or R²⁰ is azido, by reacting a compound of the formula (VIII), wherein R²⁵ is mesyloxy or tosyloxy, with a source of azide;

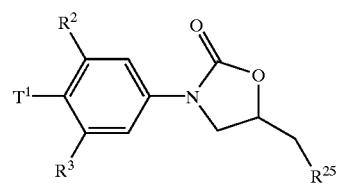

(VIII)

(j) when R¹ or R²⁰ is chioro, (1–4C)alkylthio or (1–4C) alkoxy, from a compound of the formula (VIII);

(k) when T or T¹ is of the formula (IA) wherein R⁵ is benzyl and >A—B— is >CH—CH₂—, by reaction of a compound of the formula (IX)

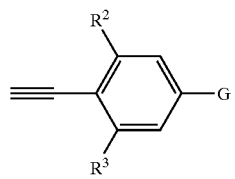

(IX)

with a nitrone of the formula benzyl-N(O)=CH—R⁶ in the presence of a Cu(I) salt, to give a compound of the formula (X)

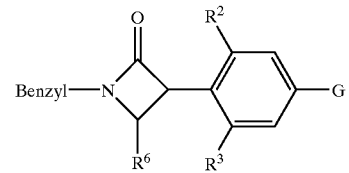

(X)

and subsequent reduction of the compound of the formula (X), (and when G in formula (IX) is nitro or amino, by subsequent formation of the desired oxazolidinone ring using a process such as process (c)); wherein G is (optionally protected) of the formula (XI), nitro or amino;

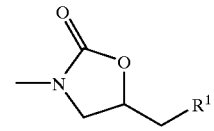

(XI)

(l) when T or T¹ is of the formula (IA) wherein R⁵ is benzyl, and >A—B— is >C(R⁴)—CH₂— (wherein R⁴ is (1–4C)alkyl) by reaction of a compound of the formula (X) with a compound of the formula R⁴—L¹ (wherein L¹ is a leaving group such as chloro, bronco or iodo) in the presence of a base (such as LDA, BuLi or NaH) and subsequent reduction of the compound of the formula (X) (and when G in formula (IX) is nitro or amino, by subsequent formation of the desired oxazolidinone ring using a process such as process (d));

(m) when T or T¹ is of the formula (IA) wherein R⁵ is benzyl, and >A—B— is >C(R⁴)—CH₂— (wherein R⁴ is hydroxy) by oxidation of a compound of the formula (X) (i.e. with R⁴ as hydrogen) using a suitable oxidizing agent, such Davis reagent, e.g. an oxaziridine (for example (1S)(+)(10-camphorsulfonyl)oxaziridine) in the presence of a suitable base such as potassium bis(trimethylsilyl)amide (and when G in formula (IX) is nitro or amino, by subsequent formation of the desired oxazolidinone ring using a process such as process (c));

(n) when T or T¹ is of the formula (IA) wherein R⁵ is benzyl, and >A—B— is >C(R⁴)—CH₂— (wherein R⁴ is halo), from the corresponding compound in which R⁴ is hydroxy (and when G in formula (IX) is nitro or amino, by subsequent formation of the desired oxazolidinone ring using a process such as process (c));

(o) when T or T¹ is of the formula (IB) or (IC) containing >A—B— of the formula >C=CH— or >C=C (R⁴ᵃ)—, and R⁵ and R⁶ are linked to give a group of the formula (IE) to (IT), by a process as described in process (e), in which the $R^5$ and $R^6$ groups are linked either before, or after, the coupling reaction between compounds of the formula (VII) and (VIIA) or (VIIB). The skilled chemist will be aware if it is desirable to perform the linking of the $R^5$ and $R^6$ groups before, or after, the coupling reaction between compounds of the formula (VII) and (VIIA) or (VIIB). The skilled chemist will be further aware when suitable protecting groups are desirable to protect specific functionalities in the compounds of the formula (VII) and (VIIA) or (VIIB) during the coupling reaction. Thus, if the $R^5$ and $R^6$ groups are linked before the coupling reaction, suitable protecting groups may, for example, be desirable to protect the $R^7$, $R^8$ and $R^9$ groups during the coupling reaction. Similarly, if the $R^5$ and $R^6$ groups are linked after the coupling reaction, suitable protecting groups (such as tert-butoxycarbonyl (BOC), trimethylsilyl (TMS) or trityl) may be desirable to protect the $R^5$ and $R^6$ groups during the coupling reaction.

Compounds in which T or $T^1$ is of the formula (IB) or (IC) containing >A—B— of the formula >CH—$CH_2$— or >CH—CH($R^{4a}$)—, and in which $R^5$ and $R^6$ are linked to give a group of the formula (IE) to (IT), may be obtained by catalytic hydrogenation of the corresponding compound wherein >A—B— is >C=CH— or >C=C($R^{4a}$)—.

Compounds in which T or $T^1$ is of the formula (IA), and in which $R^5$ and $R^6$ are linked to give a group of the formula (IE) to (IT) may be obtained by formation of the 4-membered ring according to process (k), removal of the $R^5$ benzyl group, functionalisation of the nitrogen with a suitable $R^5$ group and cyclisation by linking the $R^5$ and $R^6$ groups to form a group of the formula (IE) to (IT).
wherein $R^1$, $R^2$, $R^3$, $R^{4a}$, $R^5$, $R^6$, $R^{20}$, $R^b$ and m are as hereinabove defined; n is 0, 1 or 2 unless otherwise stated above; and thereafter if necessary:

i) removing any protecting groups;
ii) forming a pharmaceutically-acceptable salt;
iii) forming an in-vivo hydrolysable ester.

Further details concerning the above processes are given below:

(a) Methods for converting substituents into other substituents are known in the art. For example an alkylthio group may be oxidised to an alkylsulfinyl or alkysulfonyl group, a cyano group reduced to an amino group, a nitro group reduced to an amino group, a hydroxy group alkylated to a methoxy group, a hydroxy group converted to a phenylsulfonyloxy group, a hydroxy group thiomethylated to an arylthiomethyl or a heteroarylthiomethyl group (see, for example, Tet.Lett., 585, 1972), a carbonyl group converted to a thiocarbonyl group (eg. using Lawesson's reagent), a bromo group converted to an alkylthio group. When $R^5$ is benzyl, the benzyl group may be removed (using 2-chloroethyl chloroformate under von Braun conditions if the compound contains a double bond in >A—B— which is to be retained) and the >NH group functionalised to give other values for $R^5$. When $R^4$ is hydroxy, the hydroxy group may be converted to an alkanoyloxy group using Schotten-Baumann conditions. When $R^4$ is (1–4C)alkyl, the (1–4C)alkyl group may be introduced by alkylation of the saturated parent compound. When $R^4$ is halo, the halo group may be introduced by substitution starting from a compound with $R^4$ as hydroxy. In bicyclic ring systems, a double bond in allylic orientation may be prepared by dehydrobromination using a hindered non-nucleophilic base in an inert solvent at a temperature in the range ambient to 100° C. It is also possible to convert one $R^5$ group into another $R^5$ group as a final step in the preparation of a compound of the formula (I) or (II) (see the specific Examples).

(b) Compounds of the formula (I) or (II) wherein $R^1$ or $R^{20}$ is —NHS(O)$_n$(1–4C)alkyl can be prepared by oxidising a compound of the formula (I) or (II) with standard reagents known in the art for the oxidation of a thio group to a sulfinyl or sulfonyl group. For example, a thio group may be oxidised to a sulfinyl group with a peracid such as m-chloroperoxybenzoic acid and oxidising agents such as potassium permanganate can be used to convert a thio group to a sulfonyl group. Compounds of the formula (I) or (II) wherein $R^1$ or $R^{20}$ is —NHS(1–4C)alkyl can be prepared by reacting compounds of the formula (III) with a reagent such as (1–4C)alkylSCl.

c) When $R^b$ is (1–4C)alkyl, the group —C(=O)(1–4C)alkyl may be introduced into a compound of the formula (III) by standard acetylation procedures. For example, the amino group may be acetylated to give an acetamido group using the Schotten-Baumann procedure i.e. reacting the compound of the formula (I) or (II) wherein $R^1$ or $R^{20}$ is amino with acetic anhydride in aqueous sodium hydroxide and THF in a temperature range of 0° C. to ambient temperature. Preferably the acylation is carried out in situ following the catalytic hydrogenation of a compound of the formula (I) or (II) wherein $R^1$ or $R^{20}$ is azido, by performing the hydrogenation in the presence of acetic anhydride.

When $R^b$ is hydrogen, the —CHO group may be introduced into the compound of the formula (III) by reacting the latter compound with formic acetic anhydride, in an inert organic solvent such as THF, in a temperature range of 0° C. to ambient temperature, or by reacting it with ethyl formate in an inert organic solvent in the temperature range of 50–100° C.

When $R^b$ is (1–4C)alkoxy, the —COO(1–4C)alkyl group may be introduced into the compound of the formula (III) by reacting the latter compound with (1–4C)alkyl chloroformate, in the presence of an organic base such as triethylamine, in an organic solvent such as dichloromethane and in a temperature range of 0° C. to ambient temperature.

When $R^b$ is amino, the —$CONH_2$ group may be introduced into the compound of the formula (III) by reacting the latter compound either with potassium cyanate in aqueous acid (eg. hydrochloric acid) in a temperature range of ambient temperature to 40° C. or with phenyl carbamate in glyme at reflux.

When $R^b$ is chloromethyl, dichloromethyl, cyanomethyl or methoxymethyl, the —C(=O)$R^b$ group may be introduced into the compound of the formula (III) by reacting the latter compound with the appropriate acid chloride under standard conditions. The acid chloride may be prepared from the appropriate acid. When $R^b$ is acetylmethyl, the —C(=O)$R^b$ group may be introduced into the amino compound by reacting the latter compound with diketene, in an inert organic solvent such as THF, in a temperature range of 0° C. to ambient temperature.

Alternatively, the compound of the formula (III) may be reacted with the appropriate acid anhydride, in dichloromethane or THF, in the presence of an organic base such as triethylamine and in a temperature range of 0° C. to ambient temperature, or the amino compound may be reacted with the appropriate acid in the presence of 1-(3-dimethylaminopropyl)-3-ethylcarbodiimide hydrochloride and an organic base such as triethylamine, in an organic solvent such as dichloromethane, in a temperature range of 0° C. to ambient temperature.

When $R^b$ is methylamino, the —CONHMe group may be introduced into the compound of the formula (III) by reacting the latter compound with methyl isocyanate in an organic solvent such as THF or acetonitrile, in a temperature range of 0° C. to ambient temperature.

When $R_b$ is dimethylamino, the —CONMe$_2$ group may be introduced into the compound by of the formula (III) by reacting the latter compound with dimethylcarbamoyl chloride and triethylamine in an organic solvent such as THF or acetonitrile, in a temperature range of 0° C. to ambient temperature.

Standard reaction conditions for the conversion of a compound of the formula (III) to a compound of the formula (I) or (II) wherein $R^1$ or $R^{20}$ is sulfonamido are known in the art. For example, a compound of the formula (III) could be converted to a compound of the formula (I) or (II) wherein $R^1$ or $R^{20}$ is (1–4C)alkyl SO$_2$NH— by reacting the former compound with a sulfonyl chloride, for example, mesyl chloride, in a mild base such as pyridine or triethylamine.

Alternatively compounds of the formula (I) or (II) wherein $R^1$ or $R^{20}$ is (1–4C)alkyl SO$_2$NH— or (1–4C)alkylSONH— may be prepared by reacting a compound of the formula (III) with a compound of the formula (IV):

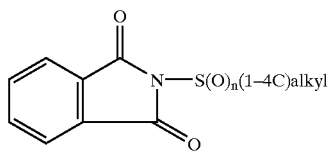

(IV)

The compound of the formula (IV) may be prepared by oxidising a compound of the formula (IVA):

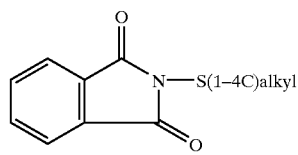

(IVA)

with standard oxidising agents known for the conversion of a thio group to a sulfinyl or sulfonyl group.

Compounds of the formula (IVA) can be prepared by reacting phthalimide with an alkylthiochloride ((1–4C)alkylSCl).

A compound of the formula (III) (i.e. a compound of the formula (I) or (II) wherein $R^1$ or $R^{20}$ is amino) may be obtained by reducing a compound of the formula (I) or (II) wherein $R^1$ or $R^{20}$ is azido (see later under process (i) for preparation of such compounds). Suitable reducing agents for reducing azido to amino in a compound of the formula (I) or (II) include triethylamine/hydrogen sulfide, triphenylphosphine or phosphite ester, or hydrogen in the presence of a catalyst. More specifically the reduction of the azido group may be carried out by heating it in an aprotic solvent, such as 1,2-dimethoxyethane, in the presence of P(OMe)$_3$ and subsequently heating in 6N aqueous hydrochloric acid, or reacting it with hydrogen in the presence of palladium on carbon in a solvent such as DMF or ethyl acetate. For further details on the reduction of azides to amines see U.S. Pat. No. 4,705,799. The azido compound may be reduced and converted to a compound of the formula (I) or (II), wherein $R^1$ or $R^{10}$ is acetamido, in situ using acetic anhydride in DMF.

(d) A compound of the formula (I) or (II) wherein $R^1$ or $R^{20}$ is fluoro may be prepared by reacting a compound of the formula (I) or (II) wherein $R^1$ or $R^{20}$ is hydroxy (hydroxy compound) with a fluorinating agent such as diethylaminosulfur trifluoride in an organic solvent such as dichloromethane in the temperature range of 0° C. to ambient temperature.

When $R^1$ or $R^{20}$ is chloro, the compound of the formula (I) or (II) may be formed by reacting the hydroxy compound with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature.

The (1–4C)alkanesulfonyloxy compound may be prepared by reacting the hydroxy compound with (1–4C) alkanesulfonyl chloride in the presence of a mild base such as triethylamine or pyridine.

The (1–4C)alkylaminocarbonyloxy compound may be prepared by reacting the hydroxy compound with (1–4C) alkyl cyanate in an organic solvent such as THF or acetonitrile, in the presence of triethylamine, in a temperature range of 0° C. to 50° C.

A compound of the formula (II) wherein $R^{20}$ is of the formula —N(CO$_2$R$^{26}$)CO(1–4C)alkyl is conveniently prepared by reacting a compound of the formula (I) and (II) wherein $R^1$ or $R^{20}$ is hydroxy with an amide of the formula HN(CO$_2$R$^{26}$)CO(1–4C)alkyl under Mitsunobu conditions. For example, in the presence of tri-n-butylphosphine and 1,1'-(azodicarbonyl)dipiperidine in an organic solvent such as THF, and in the temperature range 0° C.–60° C., but preferably at ambient temperature. Details of analogous Mitsunobu reactions are contained in Tsunoda et al, Tet. Letts., 34, 1639, (1993). Amides of the formula HN(CO$_2$R$^{26}$)CO(1–4C)alkyl may be prepared by standard procedures of organic chemistry which are within the ordinary skill of an organic chemist.

Compounds of the formulae (V) and (VI) are conveniently reacted together (to give the hydroxy compound) in the presence of a strong base such as butyl lithium, lithium hexamethyldisilazide, sodium hydride, or lithium diisopropylamide. The reaction is conveniently carried out in an inert solvent such as tetrahydrofuran (THF), dimethylformamide (DMF), N,N$^1$-dimethylpropyleneurea (DMPU) or N-methylpyrrolidone in a temperature range of −78° C. to −50° C. for the deprotonation and cyclisation. Suitable values for $R^{21}$ include ethyl, butyl and benzyl and suitable values for $R^{22}$ include ethyl and n-propyl, preferably n-propyl.

A compound of the formula (V) is conveniently prepared by reacting a chloroformate of the formula (ClCOOR$^{21}$) with a compound of the formula (VA):

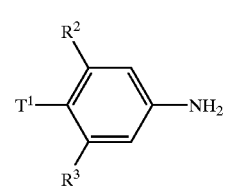

(VA)

The reaction is conveniently carried out in the presence of an inorganic or organic base such as sodium bicarbonate or an amine base such as dimethylaniline, the former in a solvent such as acetone/water and the latter in an organic solvent such as THF, toluene, DMF or acetonitrile.

A compound of the formula (VA), may be prepared by reacting a compound of the formula (VIIA) or (VIIB) with a compound of the formula (VB).

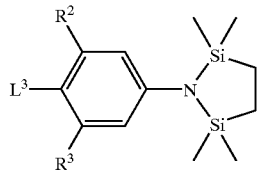

(VB)

The reaction between compounds of the formulae (VIIA) or (VIIB) and (VB) wherein L¹ is bromo or iodo may be is carried out by treating (VB) with an organolithium species such as 1-butyl methyl in an inert solvent such as THF at a low temperature, such as −78° C., followed by the addition of an anhydrous zinc halide such as zinc chloride, in a temperature range of 0° C. to ambient temperature, to generate the organozinc chloride (VB), wherein L³ is ZnCl. Treatment of the organozinc chloride in situ with a compound of the formula (VIIA) or (VIIB) followed by a suitable palladium [0] catalyst such as Pd (PPh₃)₄, in the temperature range of 0° C. to ambient temperature, results in the cross-coupled product (VA) after brief treatment with dilute acid to hydrolyse the 'stabase' protected amine.

A compound of the formula (VB) may be prepared by treatment of p-iodo or p-bromoaniline with the 'stabase' reagent (1,2-bis(chlorodimethylsilyl)ethane) in the presence of an organic base such as triethylamine.

(e) The following details concerning process (e) describe the reaction when Y in compound (VII) is a trialkyltin residue or a boronate acid or ester residue and L¹ in compounds (VIIA) and (VIIB) is an iodo or triflate leaving group. Process (e) also describes the converse reaction in which Y in compound (VII) is an iodo or triflate leaving group and L¹ in compounds (VIIA) and (VIIB) is a trialkyltin residue or a boronate acid or ester residue. Similar details concerning reaction conditions and preparation of starting materials apply (unless otherwise stated) in this converse reaction as apply to the following details.

The reaction between compounds of the formulae (VII) and (VIIA) or (VIIB), wherein Y is trialkyltin and L¹ is iodo or triflate is conveniently carried out in the presence of a palladium (0) catalyst such as Pd(PPh₃)₄ or Pd(dba)₃ in a temperature range of 0–115° C. Preferably the trialkyltin group is trimethyltin.

When Y is a boronate acid or ester, the reaction may be carried out under conditions known for the Suzuki reaction, i.e. in the presence of a palladium (0) catalyst such as Pd(PPh₃)₄ or Pd(dba)₃, in a water-miscible organic solvent such as dimethylformamide or 1,2-dimethoxyethane and in the presence of a mild base such as sodium acetate or sodium bicarbonate which is added in water. The reaction is then heated to 80° C. Alternatively, silver oxide may be used in place of the base, in which case the reaction may be carried out at a lower temperature. When Y is a boronate ester, preferably L¹ is iodo. Suitable boronate esters include lower alkyl and cyclic boronate esters, and may be prepared according to techniques known in the art.

A compound of the formula (VII) wherein Y is trimethylstannyl may be prepared by methods known in the art (for example by using methods similar to those described in patent application Ser. No. WO 9413649 from a compound of the formula (VII) wherein Y is iodo or bromo). Alternatively compounds of the formula (VII) wherein Y is a cyclic boronate ester as in (VIIC):

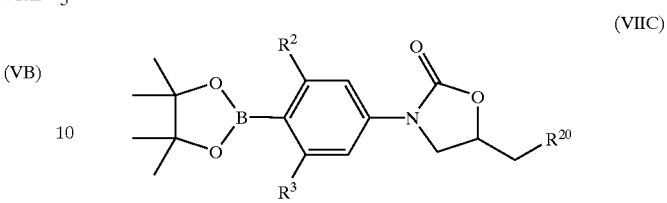

(VIIC)

may be prepared from a compound of the formula (VII) wherein Y is iodo or bromo, by sequential treatment with a suitable Pd catalyst such as PdCl₂(dppf), potassium acetate and the pinacol ester of diboron in a polar solvent such as DMSO (for example see J.Org.Chem., 1995, 60, 7508–7510). When L¹ in compounds (VIIA) and (VIIB) is a boronate ester residue, a non-cyclic (lower alkyl) boronate ester is preferred.

A compound of the formula (VII), wherein Y is iodo may be prepared by reacting a compound of the formula (VIID) with iodine monochloride in the presence of trifluoroacetic acid or with iodine and silver triflate:

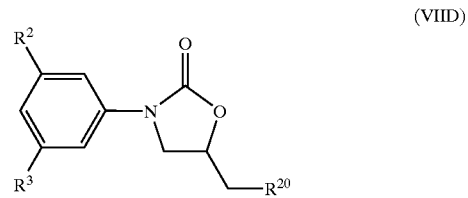

(VIID)

When Y is bromo, a compound of the formula (VII) may be prepared by brominating a compound of the formula (VIID) using standard bromination methods. For example, by reacting a compound of the formula (VIID) with N-bromosuccinimide or bromine.

A compound of the formula (VIID) may be prepared by forming the oxazolidinone ring from the amino group of a compound of the formula (VIIE) using a similar method to that described for the preparation of a compound of the formula (I) or (II) from a compound of the formula (VA)— see process (d):

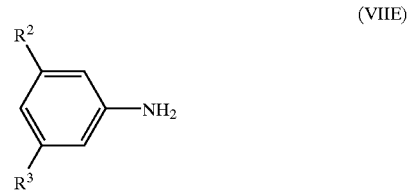

(VIIE)

The resulting compound of the formula (VIID) in which R²⁰ is hydroxy may be converted to other compounds of the formula (VIID) using similar methods to those described for the formation of a compound of the formula (I) or (II) from a compound of the formula (I) or (II) wherein R¹ or R²⁰ is hydroxy, via a compound of the formula (III)—see process (c).

A compound of the formula (VIIA) or (VIIB) wherein R⁵ is protected R⁵ and L¹ is triflate may be prepared by treating a compound of the formula (VIIF) or (VIIG) with lithium diisopropylamide in an inert solvent such as THF, at a low temperature, for example −78° C., followed by N-phenyl triflamide (for example, see methods described in Synthesis, 993–95 (1991)). A compound of the formula (VII) in which Y is triflate may not be prepared using this approach.

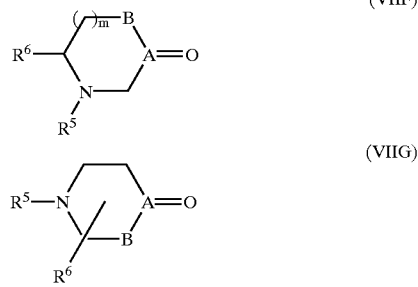

wherein $R^5$ is protected $R^5$ and —A—B— in (VIIF) and (VIIG) is —C—$CH_2$— or —C—CH($R^{4a}$)—.

Alternatively, a compound of the formula (VIIA) or (VIIB) wherein $L^1$ is iodo may be prepared by treating a hydrazone of a compound of formula (VIIF) or (VIIG) with iodine in the presence of triethylamine (for example see methods detailed in Tet. Letts. 24, 1605–1608 (1983)). A compound of the formula (VII) in which Y is iodo may not be prepared using this approach.

Compounds of the formula (VIIA) or (VIIB) wherein $R^5$ is $R^{14}CH(R^{13})(CH_2)_m$— or AR can be prepared by formation of the ring from the appropriate amine, arylamine or heteroarylamine, by reaction with ethyl acrylate to give the corresponding diethylarylimino-beta-beta-dipropionate, which can then be cyclised under Dickmann conditions to the give corresponding beta-ketoester, followed by decarboxylation with heating in acid (see methods described in J.Chem.Soc. 5110–5118 (1962)).

Alternatively, a compound of the formula (VIIA) or (VIIB) wherein $R^5$ is $R^{14}CH(R^{13})(CH_2)_m$— or AR may be prepared by reacting an appropriately substituted $R^{14}CH(R^{13})(CH_2)_m$— or AR compound containing a leaving group such as chloro, bromo or iodo with the appropriate compound of the formula (VIIA), (VIIB), (VIIF) or (VIIG) at an elevated temperature, in an inert solvent and optionally with an acid trapping agent.

(f) Suitable catalysts for the catalytic hydrogenation of a compound of the formula (I) or (II) wherein >A—B— is >C=CH— or >C=C($R^{4a}$)— include Raney nickel, platinum metal or its oxide, rhodium, zinc oxide, palladium-on-charcoal and Wilkinson's catalyst (RhCl(Ph$_3$P)$_3$. Catalyic hydrogenation is conveniently carried out in the temperature range 0° C. to 150° C., but preferably at ambient temperature and pressure, unless Wilkinson's catalytic is used in which case a temperature of approximately 50° C. and pressure of approximately 50 atmospheres are preferable.

(g) A compound in which >A—B— is of the formula >C(OH)—$CH_2$—, >C(OCO$R^{23}$)—$CH_2$—, >C(OSO$_2R^{24}$)—$CH_2$—, >C(OH)—CH($R^{4a}$)—, >C(OCO$R^{23}$)—CH($R^{4a}$)— or >C(OSO$_2R^{24}$)—CH($R^{4a}$)— may be prepared by reacting an intermediate of the formula (VB) with magnesium to form a Grignard reagent, or alternatively with n-butyl lithium to form a lithiated species, and then reacting the Grignard reagent or lithiated species with a compound of formula (VIIF) or (VIIG). The product (VA), wherein >A—B— is of the formula >C(OH)$CH_2$— or >C(OH)CH($R^{4a}$)— may then be elaborated as previously detailed for the compound of the formula (V), but with optional protection of the hydroxyl group.

The dehydration of a compound in which >A—B— is of the formula >C(OH)—$CH_2$—, >C(OCO$R^{23}$)—$CH_2$—, >C(OSO$_2R^{24}$)—$CH_2$—, >C(OH)—CH($R^{4a}$)—, >C(OCO$R^{23}$)—CH($R^{4a}$)— >C(OSO$_2R^{24}$)—CH($R^{4a}$)— to give a compound of formula (I) or (II) wherein >A—B— is of the formula >C=CH— or >C=C($R^{4a}$)— may be carried out using agents such as polyphosphoric acid, trifluoroacetic acid, trifluoroacetic anhydride, p-toluenesulfonic acid, sulfuric acid, thionyl chloride etc., in an inert solvent such as toluene, and at elevated temperatures. Suitable protection of the group $R^{20}$ may be necessary as appropriate.

A compound of the formula (I) or (II) wherein >A—B— is of the formula >CHCH($R^{4a}$)— may be prepared from a compound of the formula (I) or (II) wherein >A—B— is >C=C($R^{4a}$)— by catalytic hydrogenation, using a suitable catalyst such as palladium-on-carbon in an appropiate inert or acidic solvent such as acetic acid. Where an optically active form of compounds of the formula (VI) is used in previous steps reduction of the >A—B— double bond will produce diastereoisomers which may be separated. Where a particular diastercoisomer is of choice, a chiral asymmetry-inducing catalyst for the reduction can be used.

(h) The reaction between a compound containing T or $T^1$ of the formula (IA) or (IB) wherein >$NR^5$ is >NH (i.e. $R^5$=H) and $R^{10}COL^2$, $R^{10}SO_2L^2$ or $R^{10}CSL^2$ is conveniently carried out under similar conditions to those described for the acetylation or sulionylation of a compound of the formula (III)—see process (c).

(i) A compound of the formula (I) or (II) wherein $R^1$ or $R^{20}$ is azido may be prepared, for example, by reacting a compound of the formula (VIII) with sodium azide in an inert solvent such as DMF in a temperature range of ambient to 100° C. normally in the region of 75° C.–85° C. A compound of the formula (VIII) may be prepared by converting the hydroxy group in a compound of the formula (I) or (II) wherein $R^1$ or $R^{20}$ is hydroxy into a tosyloxy or mesyloxy group by standard methods known in the art. For example, by reacting the compound of the formula (I) or (II) with tosyl chloride or mesyl chloride in the presence of a mild base such as triethylamine, or pyridine.

(j) A compound of the formula (I) or (II) wherein $R^1$ or $R^{20}$ is chloro may be prepared from a compound of the formula (VIII), by reacting the latter compound with lithium chloride and crown ether, in a suitable organic solvent such as THF, in a temperature range of ambient temperature to reflux. A compound of the formula (I) or (II) wherein $R^1$ or $R^{20}$ is (1–4C)alkylthio or (1–4C)alkoxy may be prepared by reacting the compound of the formula (VIII) with sodium thio(1–4C)alkoxide or sodium (1–4C)alkoxide respectively, in an alcohol or THF, in a temperature range of 0° C. to reflux.

(k) The reaction of a compound of the formula (IX) with a nitrone of the formula benzyl-N(O)=CH—$R^6$ in the presence of a Cu(I) salt (preferably CuCl), to give a compound of the formula (X) is performed in the presence of an amine complexing agent, such as triethylamine or pyridine, in a solvent such as pyridine or DMF, and at a temperature in the range 0° C. to 80° C. (preferably at or near ambient temperature). The subsequent reduction of the compound of the formula (X) may be performed using a mixture of LiAlH$_4$ and aluminium chloride in an inert solvent such as THF, at a temperature in the range 0° C. to 100° C. (preferably at or near the reflux temperature of the solvent). Other reducing agents may also be used.

The compound of the formula (IX) may be prepared, for example, by introduction of the acetylenic group into a compound of the formula (IX) with a para-iodo group. See the specific Examples and J.Med.Chem. 1990, 33, 2574 for further details.

The nitrone of the formula benzyl-N(O)=CH—$R^6$ may be prepared in-situ or separately from benzyl-NHOH and $R^6$—CHO using chemistry well known in the art. Details concerning the processes (l), (m) and (n) are well known in the art. For process (l) an inert solvent (such as THF) and a temperature in the range 0° C. to 100° C. is preferred. For process (m) a low temperature is preferred. For process (n) a suitable halogenating reagent is $PBr_3$ or $PCl_3$, the reaction being performed preferably in an inert solvent such as chloroform or carbon tetrachloride and at a temperature in the range 0° C. to 50° C. (preferably at or near ambient temperature).

(o) When the $R^5$ and $R^6$ groups are linked to give a bicyclic ring structure for T or $T^1$ (either before, or after, the coupling reaction between compounds of the formula (VII) and (VIIA) or (VIIB)), this may be achieved by, for example, dehydration (lactonisation) using, for example, a carbodiimide reagent in an inert solvent at a temperature in the range 0° C. to 100° C. (see for example, Example 10). A bicyclic ring system containing a urea functionality may be obtained, for example, from an amino-ester by reaction with a phenylisocyanate in the presence of a base (for example an alkoxide) in an inert solvent at a temperature in the range 0° C. to 100° C. (see for example. Examples 11 and 13). A bicyclic ring system containing an oxazolidinone ring may be obtained, for example, by carbonylation of an amino-alcohol using phosgene or carbonyl diimidazole (see, for example, Example 17).

When an optically active form of a compound of the formula (I) is required, it may be obtained by carrying out one of the above procedures using an optically active starting material, or by resolution of a racemic form of the compound or intermediate using a standard procedure.

Similarly, when a pure regioisomer of a compound of the formula (I) is required, it may be obtained by carrying out one of the above procedures using a pure regioisomer as an intermediate, or by resolution of a mixture of the regioisomers or intermediates using a standard procedure.

According to a further feature of the invention there is provided a compound of the formula (I), or a pharmaceutically-acceptable salt thereof, for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

The invention also provides a compound of the formula (I), or a pharmaceutically-acceptable salt thereof, for use as a medicament; and the use of a compound of the formula (I) of the present invention, or a pharmaceutically-acceptable salt thereof, in the manufacture of a novel medicament for use in the production of an antibacterial effect in a warm blooded animal, such as man.

In order to use a compound of the formula (I) or a pharmaceutically-acceptable salt thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically-acceptable salt thereof and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

In addition to the compounds of the present invention the pharmaceutical composition of this invention may also contain or be co-administered with one or more known drugs selected from other clinically useful antibacterial agents (for example β-lactams or aminoglycosides). These may include penicillins, for example oxacillin or flucloxacillin and carbapenems, for example meropenem or imipenem, to broaden the therapeutic effectiveness against methicillin-resistant staphylococci. Compounds of this invention may also contain or be co-administered with bactericidal/permeability-increasing protein product (BPI) or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, a daily intravenous, subcutaneous or intramuscular dose of 5 mgkg$^{-1}$ to 20 mgkg$^{-1}$ of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

Antibacterial Activity

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of *S. aureus* and coagulase negative staphylococci. The antibacterial spectrum and potency of a particular compound may be determined in a standard test system.

The antibacterial properties of the compounds of the invention may also be demonstrated in-vivo in conventional tests.

The following results were obtained on a standard in-vitro test system. The activity is described in terms of the minimum inhibitory concentration (MIC) determined by the agar-dilution technique with an inoculum size of $10^4$ CFU/spot.

Staphylococci were tested on agar, using an inoculum of $10^4$ CFU/spot and an incubation temperature of 37° C. for 24 hours-standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours-blood is required for the growth of some of the test organisms. Typically, compounds are active in the range 0.01 to 256 μg/ml.

When tested, the compounds of the invention have MICs in the range 0.001 to 256 μμg/ml The following data were obtained for Example 44:

| ORGANISM | TYPE | MIC (μg/ml) |
|---|---|---|
| Staphylococcus aureus | Oxford | 0.25 |
| Staphylococcus aureus | Novb. Res. | 0.50 |
| Staphylococcus aureus | MRQR | 2.00 |
| Coagulase Negative Staphylococci | MS | 0.13 |
| Coagulase Negative Staphylococci | MR | 0.50 |
| Streptococcus pyogenes | C203 | 0.13 |
| Enterococcus faecalis | — | 0.50 |
| Bacillus subtilis | — | 0.50 |

Novb. Res. = Novobiocin resistant
MRQR = methicillin resistant quinolone resistant
MR = methicillin resistant
MS = methicillin sensitive.

The invention is now illustrated but not limited by the following Examples. Certain Examples are provided as a further feature of the invention as useful intermediates and/or compounds with useful anti-bacterial activity in their own right. Unless otherwise stated:

i) evaporations were carried out by rotary evaporation in vacuo and work-up procedures were carried out after removal of residual solids by filtration;

(ii) operations were carried out at ambient temperature, that is typically in the range 18–26° C. and in air unless otherwise stated, or unless the skilled person would otherwise work under an inert atmosphere;

(iii) column chromatography (by the flash procedure) was performed on Merck Kieselgel silica (Art. 9385) unless otherwise stated;

(iv) yields are given for illustration only and are not necessarily the maximum attainable;

(v) the end-products of the formula I generally have satisfactory microanalyses and their structures were confirmed by NMR and mass spectral techniques [proton magnetic resonance spectra were determined in DMSO-D6 unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets; t, triplet; q, quartet; m, multiplet; (fast-atom bombardment (FAB)) mass spectral data were obtained using a Platform spectrometer (supplied by Micromass) run in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis; and (vii) in which the following abbreviations may be used:

| MPLC | is medium pressure chromatography |
|---|---|
| TLC | is thin layer chromatography |
| DMSO | is dimethylsulfoxide |
| $CDCl_3$ | is deuterated chloroform |
| MS | is mass spectroscopy |
| ESP or ES | is electrospray |
| CI | is chemical ionization |
| DMF | is N,N-dimethylformamide |
| THF | is tetrahydrofuran |
| LDA | is lithium diisopropylamide |
| TFA | is trifluoroacetic acid |
| NMP | is N-methylpyrrolidone |
| dba | is dibenzylideneacetone |
| EtOAc | is ethyl acetate |
| aq. | is aqueous |
| sat. | is saturated |
| anh. | is anhydrous |
| mM | is mmol |
| p-TSA | is p-toluenesulfonic acid |

REFERENCE EXAMPLE 1

1-tert-Butoxycarbonyl-2RS-methoxycarbonyl-4-trifluoromethylsulphonyl-1,2,3,6-tetrahydropyridine A 1.0M solution of L-Selectride in THF (28 ml, 28 mM) was added slowly to a stirred solution of 1-tert-butoxycarbonyl-2RS-methoxycarbonyl-4-oxo-1,2,3,4-tetrahydro-pyridine (Org.Syn.,71, 200 (1992), 6.57 g, 26 mM) in THF (100 m)) at −70° C. under argon. After stirring at −70° C. for 40 minutes, a solution of phenyl triflimide (10.71 g, 30 mM) in THF (40 ml) was added and the reaction mixture was allowed to warm to ambient temperature overnight. The reaction mixture was evaporated and the title compounds isolated by MPLC (using 5% EtOAc/hexane as eluant on neutral alumina). The title mixture of products crystallised on standing. Yield=6.86 g, 68%.

NMR (300 MHz, DMSO-D6): δ 1.42 (s, 9H), 2.70 (d, 1H), 2.95 (d, 1H), 3.65 (s, 3H), 3.80 (d, 1H), 4.22 (d, 1H), 5.10 (d, 1H), 6.02 (s, 1H). MS: ES+ (M+H)=390.

EXAMPLE 1

N-((5S)-3-(4-(1-tert-Butoxycarbonyl-2RS-methoxycarbonyl-1,2,3,6-tetrahydropyrid-4-yl)phenyl)-2-oxooxazolidin-5-ylmethyl)acetamide $Pd_2(dba)_3$ (732 mg, 0.8 mM), triphenylarsine (979 mg, 3.2 mM) and lithium chloride (2.04 g, 48 mM) were added to a stirred solution of Reference Example 1 (6.85 g, 17.6 mM) in deoxygenated DMF (60 ml), and the vessel was purged well with argon. After stirring for 5 minutes at ambient temperature, a solution of N-((5S)-3-(4-trimethyltinphenyl)-2-oxooxazolidin-5-ylmethyl)acetamide (WO Patent 94/13649 A1 (23.06.94), 6.35 g, 16 mM) in DMF (15 ml) was added. The reaction mixture was stirred at ambient temperature for 18 hours. A 2.0M aq. KF solution (20 ml) was added and the reaction mixture was stirred at ambient temperature for 30 minutes. Solvent was evaporated under high vacuum and the residue was partitioned between sat. NaCl and EtOAc. The organic phase was dried over anh. $Na_2SO_4$ and evaporated to a gum. The title mixture of compounds was isolated by MPLC (using 25% acetonitrile/EtOAc as eluant on Merck 9385 silica) and triturated with hexane to give an amorphous solid. Yield=6.1 g, 81%.

NMR (300 MHz, DMSO-D6): δ 1.44 (d, 9H), 1.82 (s, 3H), 2.85 (m, 2H), 3.40 (t, 2H), 3.60 (s, 3H), 3.78 (m, 2H), 4.12 (m, 2H), 4.70 (m, 1H), 4.97 & 5.06 (2d, 1H), 6.10 (d, 1H), 7.41 (d, 2H), 7.50 (d, 2H), 8.20 (t, 1H), MS: ES+ (M+H)=474.

EXAMPLE 2

N-((5S)-3-(4-(2RS-Methoxycarbonyl-1,2,3,6-tetrahydropyrid-4-yl)phenyl)-2-oxooxazolidin-5-ylmethyl)acetamide Sat. HCl/EtOAc (10 ml) was added to a solution of Example 1 (3.5 g, 7.4 mM) in EtOAc (15 ml) and the mixture was heated to reflux briefly. A gum separated which crystallised on trituration. The solid was filtered off, washed with EtOAc and ether and dried under vacuum at 45° C. giving the title mixture of compounds as a powder. Yield= 3.4 g, 92%.

NMR (300 MHz, DMSO-D6): δ 1.82 (s, 3H), 2.88 (m, 2H), 3.40 (t, 2H), 3.80 (m, 5H), 4.11 (t, 2H), 4.48 (broard s, 1H), 4.71 (m, 1H), 6.29 (s, 1H), 7.52 (q, 4H), 8.25 (t, 1H), MS: ES+ (M+H)=374.

EXAMPLE 3

N-((5S)-3-(4-(1-Cyano-2RS-methoxycarbonyl-1,2,3,6-tetrahydropyrid-4-yl)phenyl)-2-oxooxazolidin-5-ylmethyl)acetamide Triethylamine (182 mg, 1.8 mM) was added to a stirred suspension of Example 2 (246 mg, 0.6 mM) in dry $CH_2Cl_2$ (10 ml) at ambient temperature, 4-dimethyl-aminopyridine (0.7 mg, 0.06 mM) was added, followed immediately by a solution of cyanogen bromide (382 mg, 3.6 mM) in $CH_2Cl_2$ (2 ml). After 2 hours additional triethylamine and cyanogen bromide (as above) were added and the mixture was stirred for a further 18 hours at ambient temperature. The reaction mixture was diluted with $CH_2Cl_2$, washed with 2N HCl, water, sat.$NaHCO_3$ and sat.NaCl. The organic phase was dried over anh.$Na_2SO_4$ and evaporated to a gum which was chromatographed by MPLC (using as eluant a gradient increasing in polarity from 3% to 10% MeOH in $CH_2Cl_2$ on Merck 9385 silica). The title mixture of compounds was obtained as an amorphous solid on trituration with ether. Yield=67 mg. 28%.

NMR (300 MHz, DMSO-D6): δ 1.80 (s, 3H), 2.88 (s, 2H), 3.40 (m, 2H), 3.70 (m, 4H), 4.01 (s, 2H), 4.10 (t, 1H), 4.73 (s, 2H), 6.08 (s, 1H), 7.42 (d, 2H), 7.52 (d, 2H), 8.20 (broard s, 1H), MS: ES+ (M+H)=399.

EXAMPLE 4

N-((5S)-3-(4-(1-Formyl-2RS-methoxycarhonyl-1,2,3,6-tetrahydronyrid-4-yl)phenyl)-2-oxooxazolidin-5-ylmethyl)acetamide Triethylamine (606 mg, 6.0 mM) was added to a stirred suspension of Example 2 (746 mg, 1.5 mM) in ethyl formate (20 ml) and the mixture heated under reflux for 4 days. The reaction mixture was filtered and the filtrate was evaporated to a gum. This was purified by MPLC (using 3% MeOH/ $CH_2Cl_2$ as eluant on Merck 9385 silica) and the title mixture of compounds was obtained as an amorphous foam. Yield= 506 mg, 84%.

NMR (300 MHz, DMSO-D6): δ 1.81 (s, 3H), 2.91 (m, 2H), 3.40 (t, 2H), 3.68 (m, 5H), 4.10 (t, 1H), 4.35 (m, 1H), 4.70 (m, 1H) 5.05 & 5.35 (2d, 1H), 6.12 (m, 1H), 7.42 (d, 2H), 7.50 (d, 2H), 8.18 & 8.28 (2s, 1H), 8.20 (t, 1H), MS: ES+ (M+H)=402.

EXAMPLE 5

N-((5S)-3-(4-(1-Formyl-2RS-hydroxymethyl-1,2,3,6-tetrahydrolpyrid-4-yl)phenyl)-2-oxooxazolidin-5-ylmethyl)acetamidc 2.0M Lithium borohydride in THF (3.75 ml, 7.5 mM) was added slowly to a stirred solution of Example 4 (300 mg, 0.75 mM) in THF (10 ml) at ambient temperature under argon. There was an effervescence and a precipitate separated. The mixture was stirred for 2 hours. Sat. aq. $NH_4Cl$ (5 ml) was added carefully and the reaction mixture was evaporated. The residue was dissolved in water and acidified with excess 5N aq. HCl immediately before MPLC (using as eluant a mixture increasing in gradient from 0% to 25% acetonitrile in water on Mitsubishi HP20SS polystyrene resin). The title mixture of compounds was obtained by freeze drying after partial evaporation of the acetonitrile. Yield=132 mg, 47%.

NMR (250 MHz, DMSO-D6): δ 1.82 (s, 3H), 2.55 (m, 2H), 3.39 (m, 4H), 3.53 (d, 1H), 3.72 (d of d, 1H), 3.94 (q, 1H), 4.10 (t, 1H), 4.90 & 4.62 (2m, 1H), 4.70 (m, 1H), 4.87 & 4.95 (2t, 1H), 6.10 & 6.15 (2s, 1H), 7.47 (q, 4H), 8.07 & 8.19 (2s, 1H), 8.25 (t, 1H), MS: ES+ (M+H)=374.

EXAMPLE 6

N-((5S)-3-(4-(1-Acetoxyacetyl-2RS-methoxycarbonyl-1,2,3,6-tetrahydropyrid-4-yl) phenyl)-2-oxooxazolidin-5-ylmethyl)acetamide Triethylamine (363 mg, 3.6 mM) was added to a stirred suspension of Example 2 (597 mg, 1.2 mM) in dry $CH_2Cl_2$ (15 ml) at ambient temperature. Acetoxyacetyl chloride (204 mg, 1.5 mM) was added dropwise from a μl syringe and the reaction mixture was stirred for 10 minutes. The reaction mixture was diluted with $CH_2Cl_2$, washed with 2N HCl, sat. NaCl, sat.$NaHCO_3$ and sat. NaCl. The organic phase was dried over anh.$Na_2SO_4$ and evaporated to a gum which was chromatographed by MPLC (using as eluant a mixture increasing in polarity from 0% to 3% MeOH in $CH_2Cl_2$ on Merck 9385 silica). The title mixture of compounds was obtained as an amorphous solid on trituration with ether and drying under vacuum. Yield=430 mg, 76%.

NMR (300 MHz, DMSO-D6): δ 1.80 (s, 3H), 2.10 (s, 3H), 2.9 (m, 2H), 3.40 (t, 2H), 3.60 (d, 3H), 3.74 (m, 1H), 4.0–4.45 (m, 3H), 4.75 (m, 2H), 4.95 (d, 1H), 5.02 & 5.41 (2d, 1H), 6.10 (s, 1H), 4.42 (m, 2H), 7.52 (d, 2H), 8.21 (t, 1H), MS: ES+(M+H)=474.

EXAMPLE 7

N-((5S)-3-(4-(1-Hydroxyacetyl-2RS-hydroxymethyl-1,2,3,6-tetrahydropyrid-4-yl) phenyl)-2-oxooxazolidin-5-ylmethyl)acetamide The title mixture of compounds was prepared, with only non-critical variations, by the method used for Example 5 on a 0.3 mM scale, using as starting material Example 6. Yield=22 mg. 22%.

NMR (250 MHz, DMSO-D6): δ 1.83 (s, 3H), 2.56 (m, 2H), 3.3–3.9 (m, 3H), 3.40 (t, 2H), 3.75 (d of d, 1H), 3.9–4.4 (m, 4H), 4.43 (t, 1H), 4.5–5.0 (complex, 3H), 6.11 (broard, 1H), 7.45 (q, 4H), 8.20 (t, 1H), MS: ES+ (M+H)=404.

EXAMPLE 8

N-((5S)-3-(4-(1-Hydroxyacetyl-2RS-methoxycarbonyl-1,2,3,6-tetrahydropyrid-4-yl) phenyl)-2-oxooxazolidin-5-ylmethyl)acetamide 0.25M $NaOCH_3$ in methanol (0.1 ml, 0.025 mM) was added to a stirred solution of Example 6 (118 mg, 0.25 mM) in dry methanol (2 ml) and the solution stirred for 30 minutes. Acetic acid (1 drop) was added and the mixture was evaporated. The title mixture of compounds was isolated by MPLC (using as eluant a mixture increasing in polarity from 3% to 5% MeOH in $CH_2Cl_2$ on Merck 9385 silica) and was obtained as a crisp foam on evaporation. Yield=55 mg, 51%.

NMR (300 MHz, DMSO-D6): δ 1.90 (s, 3H), 2.8–3.15 (complex 2H), 3.47 (t, 2H), 3.69 (d, 3H), 3.81 (d of d, 1H), 4.0–4.6 (complex, 5H), 4.80 & 4.90 (2m, 2H), 5.13 & 5.55 (2d, 1H), 6.19 (broad, 1H), 7.50 (d, 2H), 7.60 (d, 2H), 8.29 (t, 1H). MS: ES+ (M+H)=432.

EXAMPLE 9

N-((5S)-3-(4-(1-Hydroxyacetyl-2RS-carboxy-1,2,3, 6-tetrahydropyrid-4-yl)phenyl)-2-oxooxazolidin-5-ylmethyl)acetamide Anh.$K_2CO_3$ was added to a stirred solution of Example 6 (100 mg, 0.21 mM) in methanol (10 ml) and the suspension stirred for 1.5 hours at ambient temperature. The reaction mixture was diluted with water (10 ml), adjusted to pH 7 with 2N HCl and evaporated. The residue was dissolved in water, acidified with 2N HCl and chromatographed by MPLC (using as eluant a mixture increasing in gradient from 0% to 20% acetonitrile in water on Mitsubishi HP20SS polystyrene resin). The title compound was obtained by freeze drying after partial evaporation of the acetonitrile. Yield=60 mg, 69%

NMR (300 MHz, DMSO-D6): δ 1.78 (s, 3H), 2.70 (m, 1H), 2.98 (d, 1H), 3.38 (m, 2.5H), 3.71 (m, 1.5H), 3.9–4.9 (complex, 4H), 4.68 (m, 2H), 4.88 & 5.38 (2d, 1H), 6.11 (d, 1H), 7.42 (d, 2H), 7.53 (d, 2H), 8.21 (t, 1H), MS: ES+ (M+H)=417.

EXAMPLE 10

N-((5S)-3-(4-(1,4-Dioxo-1,3,4,6,9,9a-hexahydro-pyrido[2,1c][1,4]oxazin-8-yl)phenyl)-2-oxooxazolidin-5-ylmethyl)acetamide Dimethoxypyridine (1.2 mg, 0.012 mM) followed by dimethylaminopropyl-ethylcarbodiimide (23 mg, 0.15 mM) were added to a stirred solution of Example 9 (50 mg, 0.12 mM) in DMF (2 ml) at ambient temperature. The solution was stirred for 2.5 hours. The DMF was evaporated and the residue was taken into $CH_2Cl_2$. It was washed with 2N HCl, sat.$NaHCO_3$ and sat.NaCl and dried over anh. $Na_2SO_4$. The title mixture of compounds was obtained as a crisp foam on evaporation. Yield=23 mg, 48%.

NMR (250 MHz, DMSO-D6): δ 1.82 (s, 3H), 2.89 (d, 2H), 3.40 (t, 2H), 3.73 (m, 2H), 4.11 (t, 1H), 4.5–4.8 (complex, 3H), 4.86 (q, 2H), 6.20 (s, 1H), 7.49 (q, 4H), 8.22 (t, 1H), MS: EI+M+=399.

EXAMPLE 11

N-((5S)-3-(4-(1,3-Dioxo-2-phenyl-1,2,3,5,8,8a-hexahydroimidazo[1,5a]pyridin-7-yl)phenyl)-2-oxooxazolidin-5-ylmethyl)acetamide Triethylamine (40 mg, 0.4 mM) was added to a stirred suspension of Example 2 (100 mg, 0.2 mM) in acetonitrile (2 ml) at ambient temperature. The starting material dissolved and a faint precipitate separated. Phenyl isocyanate (60 mg, 0.5 mM) was added and the mixture was stirred overnight at ambient temperature. The reaction mixture was diluted with $CH_2Cl_2$ washed with 2N HCl and sat. NaCl. The organic phase was dried over anh.$Na_2SO_4$ and evaporated to a gum which was chromatographed by MPLC (using as eluant 4% MeOH/$CH_2Cl_2$ on Merck 9385 silica). The title mixture of compounds was obtained as a crisp foam on evaporation. Yield=65 mg, 71%.

NMR (300 MHz, DMSO-D6): δ 1.80 (s, 3H), 2.78 (d of d, 1H), 2.92 (d of d, 1H), 3.40 (t, 2H), 3.75 (d of d, 1H), 3.91 (d of d, 1H), 4.42 (m, 2H), 4.70 (m, 1H), 6.23 (d, 1H), 7.44 (m, 9H), 8.21 (t, 1H), MS: ES+ (M+H)=461.

EXAMPLE 12

N-((5S)-3-(4-(1-Ethylaminocarbonyl-2RS-methoxycarbonyl-1,2,3,6-tetrahydropyrid-4-yl) phenyl)-2-oxooxazolidin-5-ylmethyl)acetamide The title mixture of compounds was prepared, with only non-critical variations, by the method used for Example 11 on a 0.3 mM scale, using as starting materials Example 2 and ethyl isocyanate. Yield=85 mg, 64%.

NMR (300 MHz, DMSO-D6): δ 1.10 (t, 3H), 1.89 (s, 3H), 2.81 (m, 1H), 3.00 (d, 1H), 3.17 (m, 2H), 3.48 (t, 2H), 3.63 (s, 3H), 3.81 (t, 1H), 3.90 (d, 1H), 4.20 (m, 2H), 4.79 (m, 1H), 5.28 (d, 1H), 6.20 (d, 1H), 6.68 (t, 1H), 7.55 (d of d, 4H), 8.30 (t, 1H), MS: ES+ (M+H)=445.

EXAMPLE 13

N-((5S)-3-(4-(1,3-Dioxo-2-ethyl-1,2,3,5,8,8a-hexahydroimidazo[1,5a]pyridin-7-yl)phenyl)-2-oxooxazolidin-5-ylmethyl)acetamide Triethlyamine (60 mg, 0.6 mM) was added to a stirred suspension of Example 2 (150 mg, 0.3 mM) in acetonitrile (4 ml) at ambient temperature. The starting material dissolved and a faint precipitate separated. Ethyl isocyanate (53 mg, 0.75 mM) was added and the mixture was stirred for 15 minutes at ambient temperature then heated under reflux for 48 hours. The reaction mixture was diluted with $CH_2Cl_2$, washed with 2N HCl and sat. NaCl. The organic phase was dried over anh.$Na_2SO_4$ and evaporated to a gum which was chromatographed by MPLC (using as eluant 3.5% MeOH/$CH_2Cl_2$ on Merck 9385 silica). The title mixture of compounds was obtained as a crisp foam on evaporation. Yield= 91 mg, 57%.

NMR (300 MHz, DMSO-D6): δ 1.10 (t, 3H), 1.83 (s, 3H), 2.50 (partially obscured by DMSO), 2.85 (d of d, 1H), 3.41 (m, 4H), 3.80 (m, 2H), 4.10 (t, 1H), 4.22 (d of d, 1H), 4.35 (d, 1H), 4.70 (m, 1H), 6.18 (s, 1H), 7.50 (q, 4H), 8.20 (t, 1H), MS: ES+ (M+H)=413.

EXAMPLE 14

N-((5S)-3-(4-(1-tert-Butoxycarbonyl-2RS-hydroxymethyl-1,2,3,6-tetrahydropyrid-4-yl) phenyl)-2-oxooxazolidin-5-ylmethyl)acetamide 2.0M Lithium borohydride in THF (10.4 ml, 20.8 mM) was added slowly to a stirred solution of Example 1 (1.23 g, 2.6 mM) in THF (25 ml) at ambient temperature under argon. There was an effervescence during the addition and the mixture was stirred for 18 hours at ambient temperature. The reaction mixture was quenched by careful addition of sat. aq. $NH_4Cl$ (15 ml). It was acidified briefly with 2N HCl and then partitioned between water and EtOAc. The organic phase was washed with sat. $NaHCO_3$, sat. NaCl, dried over anh.$NaSO_4$ and evaporated to a gum which was chromatographed by MPLC (using as eluant a mixture increasing in polarity from 5% to 10% MeOH in $CH_2Cl_2$ on Merck 9385 silica). The title mixture of compounds was obtained as a crisp foam on evaporation. Yield=755 mg, 65%.

NMR (300 MHz, DMSO-D6): δ 1.42 (s, 9H), 1.82 (s, 3H), 2.57 (obscured by DSMO), 3.30 (m, 2H), 3.40 (t, 2H) 3.61 (broard, 1H), 3.73 (d of d, 1H), 4.10 (to 1H), 4.20 (d, 1H), 4.35 (broard s, 1H), 4.68 (m, 1H), 4.76 (t, 1H), 6.09 (s, 1H), 7.46 (q, 4H), 8.20 (t, 1H), MS: ES+ (M+H)=446.

EXAMPLE 15

N-((5S)-3-(4-(2RS-Hydroxymethyl-1,2,3,6-tetrahydropyrid-4-yl)phenyl)-2-oxooxazolidin-5-ylmethyl)acetamide Example 14 (350 mg, 0.79 mM) was warmed briefly with TFA (1 ml). It effervesced and the resulting solution was diluted with EtOAc (5 ml), and sat. HCl/EtOAc (5 ml) slowly added giving a fine precipitate. This was filtered off, washed with EtOAc and ether and dried under argon giving the title mixture of compounds as a hygroscopic HCl salt. Yield=265 mg, 87%.

NMR (300 MHz DMSO-D6, D4-acetic acid): δ 1.80 (s, 3H), 2.62 (m, 2H), 3.40 (m, 3H), 3.58 (q, 1H), 3.74 (m, 4H), 4.08 (t, 1H), 4.70 (m, 1H), 6.13 (s, 1H), 7.49 (q, 4H), MS: ES+ (M+H)=346.

EXAMPLE 16

N-((5S)-3-(4-(1-(Pyrimidin-2-yl)-2RS-hydroxymethyl-1,2,3,6-tetrahydropyrid-4-yl)phenyl)-2-oxooxazolidin-5-ylmethyl)acetamide NaHCO$_3$ (185 mg, 2.2 mM) and 2-chloropyrimidine (100 mg, 0.88 mM) were added to a stirred mixture of Example 15 (76 mg, 0.22 mM) and ethanol (5 ml). The mixture was heated under reflux for 5 days. A 1:1 mixture of MeOH/CH$_2$Cl$_2$ (10 ml) was added and the mixture filtered and evaporated to a gum. This was chromatographed by MPLC (using as eluant 4% MeOH/CH$_2$Cl$_2$ on Merck 9385 silica). The title mixture of compounds was obtained as a crisp foam on evaporation. Yield=37 mg, 40%.

NMR (300 MHz, DMSO-D6): δ 1.80 (s, 3H), 2.63 (m, 2H), 3.37 (m, 4H), 3.73 (m, 2H), 4.10 (m, 1H), 4.71 (m, 3H), 5.15 (m, 1H), 6.14 (s, 1H), 6.62 (t, 1H), 7.50 (broard s, 4H), 8.23 (broard s, 1H), 8.37 (d, 2H), MS: ES+ (M+H)=424.

EXAMPLE 17

N-((5S)-3-(4-(3-oxo-1,5,8,8a-Tetrahydrooxazolo[3,4a]pyridin-7-yl)phenyl)-2-oxooxazolidin-5-ylmethyl)acetamide Triethlyamine (101 mg, 1.0 mM) was added to a stirred suspension of Example 15 (125 mg, 0.33 mM) in CH$_2$Cl$_2$ (5 ml). Carbonyl diimidazole (81 mg, 0.5 mM) was added and the reaction mixture was stirred at ambient temperature for 5 minutes. The reaction mixture was diluted with CH$_2$Cl$_2$ washed with 2N HCl and sat.NaCl. The organic phase was dried over anh.Na$_2$SO$_4$ and evaporated to a gum which was chromatographed by MPLC (using as eluant a mixture increasing in polarity from 50% to 100% acetonitrile in EtOAc on Merck 9385 silica) The title mixture of compounds was obtained as a crisp foam on evaporation. Yield= 75 mg, 62%.

NMR (300 MHz, DMSO-D6): δ 1.80 (s, 3H), 2.28 (d, 2H), 3.40 (s, 2H), 3.76 (m, 2H), 3.94 (s, 1H), 4.10 (m, 3H), 4.50 (t, 1H), 4.70 (m, 1H), 6.15 (s, 1H), 7.48 (q, 4H), 8.22 (broard s, 1H), MS: ES+ (M+H)=372.

EXAMPLE 18

N-((5S)-3-(4-(3-oxo-1,5,6,7,8,8a-Hexahydrooxazolo[3,4a]pyridin-7-yl)phenyl)-2-oxooxazolidin-5-ylmethyl)acetamide A solution of the Example 17 (56 mg, 0.15 mM) in ethanol (10 ml) was hydrogenated over 10% palladium on charcoal (10 mg) at atmospheric pressure for 3 hours. The catalyst was removed by Millipore filtration and the solvent was evaporated giving the title mixture of compounds as a crisp foam. Yield=49 mg, 88%.

NMR (300 MHz, DMSO-D6): δ 1.45 (m, 2H), 1.80 (m, 5H), 2.74 (m, 1H), 2.98 (m 1H), 3.37 (m, 2H), 3.70 (m, 2H), 3.86 (m, 2H), 4.10 (m, 1H), 4.37 (m, 1H), 4.70 (broard s, 1H), 7.24 (d, 2H), 7.44 (m, 2H), 8.20 (broard s, 1H), MS: ES+ (M+H)=374.

REFERENCE EXAMPLE 2

(2S,4R)-2-Benzyloxycarbonyl-4-hydroxy-pyrrolidine

Trans-4-Hydroxy-L-proline (33.75 g, 0.25 mol), p-TSA (48.5 g, 0.255 mol), benzyl alcohol (100 ml) and toluene (50 ml) were refluxed together in a Dean and Stark apparatus for 18 hours. The mixture was cooled and reduced in volume to induce crystallisation to afford the benzyl ester (59 g, 62%) as a solid p-TSA salt.

NMR (300 MHz, CDCl$_3$): δ 1.96–1.12 (m, 1H) 2.30 (s, 3H), 2.36–2.50 (m, 1H), 3.50 (d, 1H), 3.75 (d, 1H), 4.49 (br s, 1H), 4.72 (dd, 1H), 5.02 (d, 1H), 5.12 (d, 1H), 7.09 (d, 2H), 7.18–7.37 (m, 5H), and 7.71 (d, 2H).

REFERENCE EXAMPLE 3

(2S,4R)-2-Benzyloxycarhonyl-4-trimethylsilyloxy-1-trityl-pyrrolidine

The benzyl ester p-TSA salt (Reference Example 2, 5.0 g, 13.1 mM) was partitioned between CHCl$_3$ (200 ml) and NH$_4$OH (1 ml) at 0° C. The aqueous laver was further extracted with CHCl$_3$/CH$_2$Cl$_2$ (1:1) (150 ml) and the combined organics were washed with water (5 ml), dried and evaporated to the crude amine (2.91 g). The amine was dissolved in CH$_2$Cl$_2$ and treated with chlorotrimethylsilane (1.4 g, 1.7 ml, 13.1 mM), refluxed for 0.5 hours and cooled. Triethylamine (1.32 g, 1.82 ml, 13.1 mM) was added to the cooled (0° C.) solution, followed by trityl chloride (3.64 g, 13.1 mM) and the solution stirred for 2 hours. The solution was then diluted with CH$_2$Cl$_2$ (50 ml), washed with saturated aqueous NaHCO$_3$, water, dried and evaporated to a residue. The residue was purified by silica-gel MPLC (using 10% EtOAc/isohexane as eluant) to afford the title product (2.89 g, 42%).

NMR (300 MHz, D6-DMSO): δ 0.00 (s, 9H), 0.80–0.95 (m, 1H), 1.70–1.80 (m, 1H), 2.39 (dd, 1H), 3.50 (dd, 1H), 3.84 (d, 1H), 4.41–4.55 (m, 1H), 5.15 (s, 2H) and 7.21–7.58 (m, 20H), MS: (ESP+) 294 (MH+ —Ph$_3$C, 28%).

REFERENCE EXAMPLE 4

(2S,4R)-2-Benzyloxycarbonyl-4-hydroxy-1-trityl-pyrrolidine

The silyl ether (Reference Example 3, 2.89 g, 5.42 mM) in THF (35 ml) was cooled to 0° C. and treated with tetra-n-butylammoniumfluoride (1.0 M in THF, 5.42 ml, 5.42 mM) and stirred for 15 minutes. The solution was evaporated, the residue dissolved in CH$_2$Cl$_2$ (75 ml) and washed with water (15 ml), dried and evaporated to crude product. This was purified by MPLC (using as eluant 25% EtOAc/isohexane on silica) to give the title alcohol (2.08 g, 83%).

NMR (300 MHz, D6-DMSO): δ 0.69–0.81 (m, 1H), 1.62 (dd, 1H), 2.23 (t, 1H), 3.36 (t 1H), 3.71 (d, 1H), 4.22–4.37

(br s, 1H), 4.71 (d, 1H), 5.03 (s, 2H) and 7.10–7.47 (m, 20H), MS: (ESP+) 222 (MH+–Ph$_3$C, 10%).

REFERENCE EXAMPLE 5

2S-Benzyloxycarbonyl-4-oxo-1-trityl-pyrrolidine

A solution of dimethylsulfoxide (0.98 g, 0.89 ml, 12.57 mM) in CH$_2$Cl$_2$ (45 ml) was added dropwise to a stirred solution of oxalyl chloride (0.80 g, 0.55 ml, 6.29 mM) in CH$_2$Cl$_2$ (70 ml) at –78° C. The solution was stirred for 5 minutes and then the alcohol (Reference Example 4, 2.64 g, 5.70 mM) in CH$_2$Cl$_2$ (40 ml) was added dropwise and stirring continued for 15 minutes. Triethylamine (2.88 g, 3.96 ml. 28.5 mM) was added and stirring continued at –78° C. for 2 hours. The solution was diluted with CH$_2$Cl$_2$ (200 ml). washed with sat. aq. NaHCO$_3$, water, dried and evaporated to the crude ketone. This was purified by silica-gel MPLC (using as eluant 10% EtOAc/isohexane) to give the title ketone (2.43 g, 92%).

NMR (300 MHz, D6-DMSO): δ 1.04 (dd, 1H), 1.92 (d, 1H), 3.31 (d, 1H), 3.68 (d, 1H), 4.18 (d, 1H), 5.10 (d, 1H), 5.24 (d, 1H) and 7.15–7.50 (m, 20H). MS: (ESP+) 220 (MH+–Ph$_3$C, 5%).

REFERENCE EXAMPLE 6

2S-Benzyloxycarbonyl-4-trifluoromethylsulphonyl-1-trityl-2,5-dihydropyrrole

The ketone (Reference Example 5, 8.50 g, 18.4 mM) in dry THF (200 ml) at –78° C. was treated with potassium bis(trimethylsilyl)amide (0.5 M in toluene, 43 ml, 21.4 mM) and stirred for 0.5 hours. N-Phenyl-bis (trifluoromethanesulfonamide) (7.63 g, 21.4 mM) was added and stirring continued for 64 hours. The mixture was evaporated and the residue purified by silica-gel MPLC (using as eluant 5% EtOAc/isohexane) to give the title triflate (9.80 g, 90%).

NMR (300 MHz, D6-DMSO): δ 3.63 (d, 1H), 4.28 (dt, 1H), 4.50–4.58 (m, 1H), 5.15 (d, 1H), 5.20 (d, 1H), 5.65 (s, 1H) and 7.10–7.48 (m, 20H).

EXAMPLE 19

N-((5S)-3-(4-(2S-Benzyloxycarbonyl-1-trityl-2,5-dihydropyrrol-4-yl)phenyl)-2-oxooxazolidin-5-ylmethyl)acetamide The triflate (Reference Example 6, 0.854 g, 1.44 mM), palladium(0) bis(dibenzylideneacetone) (0.073 g, 0.08 mM), triphenylarsine (0.095 g, 0.31 mM) and lithium chloride (0.327 g, 7.78 mM) were dissolved in degassed DMF (15 ml). The oxazolidinone stannane as used in Example 1 (WO Patent 94/13649 A1 (Jun. 23, 1994), 0.619 g, 1.56 mM) was added after 5 minutes and the solution stirred at 40° C. for 18 hours. The mixture was dissolved in EtOAc (50 ml) and water (20 ml), treated with aq. potassium fluoride (2M, 3.9 ml, 7.8 mM), stirred for 20 minutes and then filtered through Celite. The organic layer was washed with water (250 ml), dried and evaporated to the crude product which was purified by firstly silica-gel MPLC (using as eluant 3% MeOH/CH$_2$Cl$_2$) and then silica-gel MPLC (using as eluant 40% MeCN/EtOAc) to afford the title product (0.255g, 26%).

NMR (300 MHz, D6-DMSO): δ 1.80 (s, 3H), 3.38 (t, 2H), 3.67 (dd, 1H), 3.95 (d, 1H), 4.04 (t, 1H), 4.39 (d, 1H), 4.60–4.71 (m, 2H), 5.10 (d, 1H), 5.19 (d, 1H), 5.78 (s, 1H), 7.08–7.25 (m, 12H), 7.30–7.40 (m, 6H), 7.43–7.52 (m, 6H) and 8.19 (t, 1H).

EXAMPLE 20

N-((5S)-3-(4-(2S-Benzyloxycarbonyl-2,5-dihydropyrrol-4-yl)phenyl)-2-oxooxazolidin-5-ylmethyl)acetamide The N-trityl compound (Example 19, 1.07 g, 1.58 mM) was dissolved in formic acid (10 ml) and water (1 ml) at 0° C. and allowed to warm to ambient temperature over 2 hours with stirring. The mixture was then diluted with EtOAc (100 ml). cooled to 4° C. and taken to pil 10 with NH$_4$OH solution. The aqueous layer was extracted with EtOAc and the combined organics washed with water, dried and evaporated to a residue which was purified by silica-gel MPLC (using as eluant a mixture increasing in polarity from 4% to 7% MeOH in CH$_2$Cl$_2$) to afford the title amine (0.55 g, 80%).

NMR (300 MHz, D6-DMSO): δ 1.80 (3H, s), 3.10 (1H, br s), 3.40 (2H, t), 3.68–3.78 (1H, m), 3.99 (1H, br d), 4.03–4.17 (2H, m), 4.69 (2H, br s), 5.12 (2H, s), 6.25 (1H, s), 7.26–7.40 (5H, m), 7.41–7.55 (4H, m) and 8.20 (1H, t). MS: (ESP+) 436 (MH+, 100%).

EXAMPLE 21

N-((5S)-3-(4-(1-Benzyloxymethylcarbonyl-2S-benzyloxycarbonyl-2,5-dihydropyrrol-4-yl)phenyl)-2-oxooxazolidin-5-ylmethyl)acetamide The amine (Example 20, 0.257 g, 0.59 mM) in acetone-:water (2:1) (14 ml) at 0° C. was treated with benzyloxy-acetyl chloride (0.214 g, 0.183 ml, 1.16 mM) and NaHCO$_3$ (0.198 g, 2.36 mM) and the mixture stirred for 4 hours. The solution was diluted with EtOAc (40 ml) and water (10 ml), and the organics dried and evaporated to a solid. This was purified by silica-gel MPLC (using as eluant 3% MeOH/CH$_2$Cl$_2$) to give an impure solid which was dissolved in EtOAc and washed with 10% HCl (2×), dried and evaporated to afford the title product (0.129 g, 38%).

NMR (300 MHz, D6-DMSO): δ 1.80 (3H, s), 3.24 (2H, s), 3.40 (2H, t), 4.10 (1H, t), 4.30 (1H, s), 4.55 (2H, s), 4.70 (3H, br s) 5.17 (2H, s), 5.29 (1H, s), 6.40 (1H, s), 7.23–7.39 (10H, m), 7.46–7.60 (4H, m) and 8.20 (1H, t). MS: (ESP+) 584 (MH+, 100%).

EXAMPLE 22

N-((5S)-3-(4-(1-Acetoxyacetyl-2S-benzyloxycarbonyl-2,5-dihydropyrrol-4-yl)phenyl)-2-oxooxazolidin-5-ylmethyl)acetamide The amine (Example 20, 0.262 g, 0.6 mM) was transformed using the procedure given for Example 21 but with non-critical variations and using acetoxyacetyl chloride in place of benzyloxyacetyl chloride into the title product (0.268 g, 83%).

NMR (300 MHz, D6-DMSO): δ 1.80 (3H, s), 2.10 (3H, s), 3.40 (2H, t), 3.75 (1H, dd), 4.11 (1H, t), 4.63–4.80 (3H, m), 4.81 (1H, d), 4.91 (1H, d), 5.13 (2H, s), 5.20–5.28 (1H, m), 6.40 (1H, s), 7.24–7.40 and 7.50–7.59 (together 9H, in) and 8.20 (1H, t). MS: (ESP+) 536 (MH+, 100%).

EXAMPLE 23

N-((5S)-3-(4-(1-Methylsulphonyl-2S-benzyloxycarbonyl-2,5-dihydropyrrol-4-yl)phenyl)-2-oxooxazolidin-5-ylmethyl)acetamide The amine (Example 20, 0.155 g, 0.36 mM) in CH$_2$Cl$_2$ (4 ml) at 0° C. was treated with triethylamine (0.072 g, 0.099 ml, 0.713 mM) followed by methanesulfonyl chloride (0.82 g, 0.55 ml, 7.13 mM) and stirred for 2 hours. The solution was diluted with $CH_2Cl_2$, washed with $NaHCO_3$, water, dried and evaporated to a residue. This was purified by silica-gel MPLC (using as eluant 3% MeOH/$CH_2Cl_2$) to give an oil which on trituration with diethyl ether gave the title product (0.141 g, 76%) as a solid.

NMR (300 MHz, D6-DMSO): δ 1.80 (3H, s), 3.03 (3H, s), 3.40 (2H, t), 3.70–3.80 (1H, m), 4.10 (1H, t), 4.55 (1H, dd), 4.62–4.77 (2H, m), 5.16 (1H, d), 5.21 (1H, d), 5.37–5.41 (1H, m), 6.30 (1H, s), 7.28–7.40 (5H, m), 7.55 (4H, s) and 8.20 (1H, t). MS: (ESP+) 514 (MH+, 85%).

EXAMPLE 24

N-((5S)-3-(4-(1-Cyano-2S-benzyloxycarbonyl-2,5-dihydropyrrol-4-yl)phenyl)-2-oxooxazolidin-5-ylmethyl)acetamide The amine (Example 20, 0.150 g, 0.34 mM) in $CH_2Cl_2$ (4 ml) was treated with triethylamine (0.103 g, 0.142 ml, 1.02 mM), 4-dimethylaminopyridine (0.004 g, 0.034 mM) followed by a suspension of cyanogen bromide (0.182 g, 1.72 mM) in $CH_2Cl_2$ and stirred for 1 hour. The solution was diluted with $CH_2Cl_2$ (5 ml), washed with $NaHCO_3$ (4 ml), water (4 ml), dried and evaporated to an oil. This was purified by silica-gel MPLC (using as eluant 4% MeOH/$CH_2Cl_2$) to give an oil which on trituration with diethyl ether gave the title N-cyano compound (0.097 g, 62%) as a solid.

NMR (300 MHz, D6-DMSO): δ 1.80 (3H, s), 3.40 (2H, t), 3.75 (1H, dd), 4.09 (1H, t), 4.63–4.75 (3H, m), 5.21 (2H, s), 5.43–5.50 (1H, m), 6.34 (1H, s), 7.28–7.55 (9H, m) and 8.20 (1H, t), MS: (ESP+) 478 (M+$NH_4$, 15%).

EXAMPLE 25

N-((5S)-3-(4-(1-Formyl-2S-benzyloxycarbonyl-2,5-dihydropyrrol-4-yl)phenyl)-2-oxooxazolidin-5-ylmethyl)acetamide The amine (Example 20, 0.161 g, 0.37 mM) was refluxed in base-(NaOH)-washed ethyl formate (8 ml) for 3 days. The solution was then evaporated and the residue purified by silica-gel MPLC (using as eluant 3% MeOH/$CH_2Cl_2$) to give a solid which on trituration with diethyl ether gave the title N-formyl compound (0.117 g, 68%) as a solid.

NMR (300 MHz, D6-DMSO): δ 1.80 (3H, s), 3.40 (2H, t), 3.75 (1H, dd), 4.10 (1H, t), 4.35–4.89 (3H, m), 5.17 (1H, s), 5.19 (1H, s), 5.23 (0.5H, br s), 5.60 (0.5H, br s), 6.40 (1H, d), 7.25–7.40 (5H, m), 7.50–7.60 (4H, m), 8.20 (1H, t), 8.24 (0.5H, s) and 8.29 (0.5H, s). MS: (ESP+) 464 (MH+, 100%).

EXAMPLE 26

N-((5S)-3-(4-(1-Hydroxyacetyl-2S-benzyloxycarbonyl-2,5-dihydropyrrol-4-yl)phenyl)-2-oxooxazolidin-5-ylmethyl)acetamide Example 22 (0.108 g, 0.200 mM) was stirred in methanolic ammonia for 20 hours. The mixture was evaporated and the residue triturated with acetonitrile to afford the title alcohol (0.080 g, 99%).

NMR (300 MHz, D6-DMSO): δ 1.80 (s, 3H), 3.40 (t, 2H), 3.72–3.80 (m, 1H), 4.05–4.20 (m, 3H), 4.55–4.80 (m, 4H), 5.00 (br s, 1H), 6.29 (s, 1H), 7.04 (s, 1H), 7.43 (s, 1H), 7.54 (s, 4H) and 8.19–8.27 (m, 1H), MS: (ESP+) 403 (MH+, 50%).

EXAMPLES 27 AND 28

N-((5S)-3-(4-(1-(Pyrimidin-2-yl)-2S-ethoxycarbonyl-2,5-dihydropyrrol-4-yl)phenyl)-2-oxooxazolidin-5-ylmethyl)acetamide and N-((5S)-3-(4-(2S-Ethoxycarbonyl-2,5-dihydropyrrol-4-yl)phenyl)-2-oxooxazolidin-5-ylmethyl)acetamide The amine (Example 20, 0.140 g, 0.32 mM) in ethanol (5 ml) containing $NaHCO_3$ (0108 g, 1.28 mM) and 2-chloropyrimidine (0.055 g, 0.48 mM) was refluxed for 4.25 hours. The mixture was cooled, diluted with EtOAc (30 ml), washed with $NH_4OH$, brine, dried and evaporated to a residue which was purified by Isolute chromatography (using as eluant a mixture increasing in polarity from 2% to 10% MeOH in $CH_2Cl_2$). The first-eluted material was triturated with diethyl ether to give the N-pyrimidine title compound Example 27 (0.010 g, 7%).

NMR (300 MHz, D6-DMSO): δ 1.27 (t, 3H), 1.84 (s, 3H), 3.43 (t, 2H), 3.78 (dd, 1H), 4.05–4.19 (m, 3H), 4.73 (br s, 3H), 5.30–5.37 (m, 1H), 6.44 (d, 1H), 6.75 (t, 1H), 7.57 (d, 2H), 7.64 (d, 2H), 8.21 (t, 1H) and 8.33–8.52 (m, 2H). MS: (ESP+) 452 (MH+, 100%).

The second-eluted material was triturated with diethyl ether to give the title ethyl ester Example 28 (0.014 g, 12%).

NMR (300 MHz, D6-DMSO): δ 1.28 (t, 3H), 1.83 (s, 3H), 3.42 (t, 2H), 3.73–3.83 (m, 1H), 4.14 (t, 1H), 4.25 (q, 2H), 4.33 (d, 1H), 4.44 (d, 1H), 4.66–4.80 (m, 1H), 5.25 (d, 1H), 6.43 (d, 1H), 7.58 (d, 2H), 7.63 (d, 2H), 8.23 (t, 1H) and 9.51 (br s, 1H), MS: (ESP+) 374 (MH+, 100%).

EXAMPLE 29

N-((5S)-3-(4-(2S-Hydroxymethyl-1-trityl-2,5-dihydropyrrol4-yl)phenyl)-2-oxooxazolidin-5-ylmethyl)acetamide The benzyl ester (Example 19, 1.30 g, 1.92 mM) in dry THF (35 ml) at −78° C. under argon was treated with lithium borohydride (2.0M in THF, 5.76 ml, 11.52 mM) and the cooling bath was immediately removed. The mixture was stirred for 24 hours whereupon more lithium borohydride (5.76 ml) was added and stirring continued. After another 24 hours more lithium borohydride (8.00 ml) was again added. After a total reaction time of 53 hours, water (30 ml) was added followed by 2M HCl (15 ml). After $H_2$ evolution had ceased, the solution was extracted with EtOAc (2×50 ml) and the organic extracts were washed with brine, dried and evaporated to a foam. This was purified by silica-gel MPLC (using as eluant 25% MeCN/EtOAc) to give the title alcohol (0.758 g, 69%).

NMR (300 MHz, D6-DMSO): δ 1.80 (s, 3H), 3.37 (t, 2H), 3.40–3.49 (m, 1H), 3.61–3.71 (m, 2H), 3.79 (d, 1H), 3.92–4.03 (m, 2H), 4.20 (d, 1H), 4.50 (t, 1H), 4.60–4.71 (m, 1H), 5.78 (s, 1H), 6.97–7.37 (m, 14H), 7.50 (d, 5H) and 8.18 (t, 1H).

EXAMPLE 30

N-((5S)-3-(4-(2S-(Pyrimidin-2-yl)thiomethyl-1-trityl-2,5-dihydropyrrol-4-yl)phenyl)-2-oxooxazolidin-5-ylmethyl)acetamide The alcohol (Example 29, 0.251 g, 0.44 mM) and 2-mercaptopyrimidine (0.098 g, 0.88 mM) and N,N-dimethylformamide dineopentyl acetal (0.304 g, 0.366 ml, 1.31 mM) in dry acetonitrile (10 ml) were refluxed for 4 hours. The solution was cooled, evaporated and the residue purified by silica-gel MPLC (using as eluant 3% MeOH/$CH_2Cl_2$) to give an oil. This was triturated with diethyl ether to give over two crops the title product (0.172 g, 59%) as a powder.

NMR (300 MHz, D6-DMSO): δ 1.80 (s, 3H), 3.30–3.42 (m, 3.33H), 3.53–3.72 (m, 2H), 3.81 (d, 0.66H), 4.00 (t, 0.66H), 4.05 (t, 0.33H), 4.29 (d, 0.66H), 4.46–4.55 (m, 0.66H), 4.60–4.70 (m, 1.33H), 4.80 (br s, 0.33H), 5.75 (s, 0.66H), 6.20 (d, 0.33H), 6.95–7.03, 7.10–7.30 and 7.43–7.55 (each m, together 20H), 8.12–8.23 (m, 1H), 8.50 (d, 1.33H) and 8.60 (d, 0.66H).

REFERENCE EXAMPLE 7

N-((5S)-3-(4-(2S-(Pyrimidin-2-yl)thiomethyl-2,5-dihydropyrrol-4-yl)phenyl)-2-oxooxazolidin-5-ylmethyl)acetamide The N-trityl compound (Example 30, 0.528 g, 0.79 mM) in acetone (8 ml) at 0° C. was treated with freshly prepared HCl/acetone (4 ml) and stirred. The mixture was periodically treated with 10% HCl in water until TLC indicated consumption of starting material. The reaction mixture was then diluted with EtOAc (30 ml) and taken to pH 11 with NH$_4$OH solution. The aqueous layer was extracted with EtOAc and the combined organics dried (MgSO$_4$) and evaporated to a residue which was triturated with diethyl ether to give the title amine (0.309 g, 92%) which was used without further purification.

NMR (300 MHz, D6-DMSO): δ 1.80 (s, 3H), 3.31–3.50 (m, 4H), 3.67–3.78 (m, 2H), 4.10 (t, 1H), 4.16 (br s, 1H), 4.60–4.76 (m, 2H), 6.25–6.41 (m, 1H), 7.14–7.31 (m, 2H), 7.46 (d, 2H), 7.54 (d, 2H), 8.21 (t, 1H) and 8.64 (t, 2H). MS: (ESP+) 426 (MH+, 100%).

EXAMPLE 31

N-((5S)-3-(4-(1-Formyl-2S-(pyrimidin-2-yl)thiomethyl-2,5-dihydropyrrol-4-yl)phenyl)-2-oxooxazolidin-5-ylmethyl)acetamide The amine (Reference Example 7, 0.048 g, 0.11 mM) was refluxed in ethyl formate (3 ml). After 2 hours, chloroform (1 ml) and dichloromethane (1 ml) was added to solublise the precipitate. After 70 hours the solution was evaporated and the residue dissolved in acetonitrile/EtOAc (1:1) and the precipitate removed by filtration. The mother liquor was purified by Isolute chromatography (using as eluant a mixture increasing in polarity from 50% to 70% MeCN in EtOAc) to give after trituration with diethyl ether the title product (0.010 g, 20%).

NMR (300 MHz, D6-DMSO): δ 1.82 (s, 3H), 3.40 (t, 2H), 3.55–4.35 (m, 5H), 4.59–4.80 (m, 2.5H), 5.13–5.23 (m, 0.5H), 6.20–6.40 (m, 1H), 7.23 (t, 0.33H), 7.39 (t, 0.66H), 7.45–7.60 (m, 4H), 8.12 (s, 0.33H), 8.20 (t, 1H), 8.36 (d, 0.66H), 8.62 (dd, 0.66H) and 8.69 (dd, 1.33H). MS: (ESP+) 454 (MH+, 100%).

EXAMPLE 32

N-((5S)-3-(4-(1-Cyano-2S-(pyrimidin-2-yl)thiomethyl-2,5-dihydropyrrol-4-yl)phenyl)-2-oxooxazolidin-5-ylmethyl)acetamide The amine (Reference Example 7, 0.103 g, 0.24 mM) in CH$_2$Cl$_2$ (4 ml) was treated with triethylamine (0.073 g, 0.100 ml, 0.72 mM) and 4-dimethylaminopyridine (4-DMAP) (0.003 g, 0.024 mM), followed by a suspension of cyanogen bromide (0.129 g, 1.21 mM) in CH$_2$Cl$_2$ (3 ml). The solution was stirred for 1 hour. The mixture was then diluted with CH$_2$Cl$_2$ (7 ml), washed with sat. aq. NaHCO$_3$ (3 ml), water (3 ml), dried and evaporated to an oil which was purified by Isolute chromatography (using as eluant 6% MeOH/CH$_2$Cl$_2$). The resultant oil was triturated with diethyl ether to give the title product (0.071 g, 66%).

NMR (300 MHz, D6-DMSO): δ 1.80 (s, 3H), 3.39 (t, 2H), 3.45–3.85 (m, 3.33H), 4.06–4.15 (m, 1H), 4.24 (d, 0.33H), 4.35 (d, 0.33H), 4.61 (s, 1H), 4.65–4.75 (m, 1.33H), 5.01 (br s, 0.66H), 6.23 (d, 0.66H), 6.34 (d, 0.33H), 7.19–7.30 (m, 1H), 7.35–7.56 (m, 4H), 8.20 (t, 1H), 8.63 (d, 1.33H) and 8.68 (d, 0.66H). MS: (ESP+) 451 (MH+, 32%).

EXAMPLE 33

N-((5S)-3-(4-(1-Acetoxyacetyl-2S-(pyrimidin-2-yl)thiomethyl-2,5-dihydropyrrol-4-yl)phenyl)-2-oxooxazolidin-5-ylmethyl)acetamide The amine (Reference Example 7, 0.112 g, 0.26 mM) in CH$_2$Cl$_2$ (5 ml) containing 4-DMAP (0.003 g, 0.06 mM) was treated with acetoxyacetyl chloride (0.071 g, 0.056 ml, 0.52 mM) and stirred for 3.5 hours. More acetoxyacetyl chloride (0.056 ml) was added and stirring continued for 10 minutes. The solution was then diluted with CH$_2$Cl$_2$ (10 ml), washed with sat. aq. NaHCO$_3$ (5 ml), brine (5 ml), dried (MgSO$_4$) and evaporated to a residue which was purified by silica-gel MPLC (using as eluant 4% MeOH/CH$_2$Cl$_2$) to give a foam (0.081 g). This was triturated with diethyl ether to give the title product (0.075 g, 55%) as crystals.

NMR (300 MHz, D6-DMSO): δ 1.80 (s, 3H), 2.05 (s, 1.5H), 2.10 (s, 1.51), 3.36–3.91 (m, 6H), 4.05–5.28 (m, 6H), 6.20 (s, 0.5H), 6.38 (br t, 0.5H), 7.15–7.60 (m, 5H), 8.20 (br s, 1H), 8.57 (d, 1H) and 8.68 (t, 1H). MS: (ESP+) 526 (MH+, 100%).

REFERENCE EXAMPLE 8

(2S,4R)-2-Allyloxycarbonyl-4-hydroxy-pyrrolidine

Trans-4-Hydroxy-L-proline (30 g, 229 mM), p-TSA (44.7 g, 235 mM), allyl alcohol (100 ml) and toluene (50 ml) were refluxed together in a Dean and Stark apparatus for 18 hours. The mixture was cooled to ambient temperature and evaporated to afford the title allyl ester (75 g, 91%).

NMR (300 MHz, D6-DMSO): δ 2.00–2.25 (m, 2H), 2.30 (s, 3H), 3.10 (d, 1H), 3.32–3.49 (m, 1H), 4.35–4.46 (m, 2H), 4.55 (dd, 1H), 4.60–4.75 (m, 2H), 5.25 (dd, 1H), 5.37 (dd, 1H), 5.94 (m, 1H), 7.10 (d, 2H), 7.50 (d, 2H) and 9.40 (br s 1H).

REFERENCE EXAMPLE 9

(2S,4R)-2-Allyloxycarbonyl-1-tert-butoxycarbonyl-4-hydroxy-pyrrolidine

The allyl ester (Reference Example 8, 55.4 g, 153 mM) in dioxan:water (2:1) (200 ml) was treated with NaOH (6.12 g, 153 mM) and di-tert-butyl dicarbonate (35 g, 160 mM) and stirred for 17 hours. The solution was then diluted with EtOAc (800 ml), washed with water (2×100 ml), dried (MgSO$_4$) and evaporated to give the title product (38.4 g, 93%).

NMR (300 MHz, D6-DMSO) δ 1.32 (s, 6H), 1.37 (s, 3H), 1.84–1.97 (m, 1H), 2.05–2.20 (m, 1H), 3.21–3.32 (m, 1H), 3.33–3.47 (m, 1H), 4.19–4.30 (m, 2H), 4.59 (d, 2H) 5.05 (d, 1H), 5.20 (dd, 1H), 5.30 (dd, 1H) and 5.82 (m, 1H). MS: (ESP+) 272 (MH+, 100%).

REFERENCE EXAMPLE 10

(2S,4R)-2-Hydroxymethyl-1-tert-butoxycarbonyl-4-hydroxy-pyrrolidine

Reference Example 9 (16.8 g, 62 mM) in dry THF (350 ml) in flame-dried glassware at −5° C. was treated with lithium aluminium hydride (1.0 M in THF, 62 ml, 62 mM) over 1.25 hours whilst maintaining the temperature below −1° C. The solution was then stirred at 0° C. for 1.75 hours. Water (2.4 ml) was added, then after 5 minutes 15% aq. NaOH (2.4 ml) was added and then after a further 5 minutes water (7.2 ml) was added. After 5 minutes the mixture was filtered and evaporated to a residue which was purified by silica-gel MPLC (using as eluant a mixture increasing in polarity from 4% to 8% MeOH in $CH_2Cl_2$) to give the title diol (8.52 g, 63%).

NMR (300 MHz, D6-DMSO): δ 1.40 (s, 9H), 1.70–2.03 (m, 2H), 3.11–3.28 (m, 2H), 3.34–3.50 (m, 2H), 3.75 (br s, 1H), 4.15–4.23 (m, 1H), 4.58 (d, 1H) and 4.77 (s, 1H).

REFERENCE EXAMPLE 11

(2S,4R)-2-tert-Butyldimethylsilyloxymethyl-1-tert-butoxycarbonyl-4-hydroxy-pyrrolidine The diol (Reference Example 10, 3.81 g, 17.56 mM) in $CH_2Cl_2$ (100 ml) was treated with tert-butyldimethyl silyl chloride (2.92 g, 19.35 mM), 4-DMAP (0.086 g, 0.71 mM) and triethylamine (1.95 g, 2.69 ml, 19.35 mM) and was stirred for 18 hours. The solution was washed with 2M HCl (15 ml), brine (15 ml), dried ($MgSO_4$) and evaporated to give an oil which was purified by silica-gel MPLC (using as eluant 4% MeOH/$CH_2Cl_2$) to give the title silyl ether (5.47 g, 94%).

NMR (300 MHz, D6-DMSO): δ 0.25 (s, 6H), 0.89 (s, 9H), 1.40 (s, 9H), 1.80–1.95 (m, 1H), 1.96–2.05 (m, 1H), 3.20–3.30 (m, 2H), 3.55–3.70 (m, 1.5H), 3.78–3.88 (m, 1.5H), 4.22–4.30 (m, 1H) and 4.85 (d, 1H). MS: (ESP+) 332 (MH+, 16%).

REFERENCE EXAMPLE 12

(2S)-2-tert-Butyldimethylsilyloxymethyl-1-tert-butoxycarbonyl-4-oxo-pyrrolidine

A solution of dimethylsulfoxide (5.2 g, 4.7 ml, 66 mM) in dichloromethane (120 ml) was added to oxalyl chloride (4.2 g, 2.9 ml, 33 mM) in dichloromethane (120 ml) under argon at −78° C. After 10 minutes the silyl ether (Reference Example 11, 9.9 g, 30 mM) in dichloromethane (120 ml) was added dropwise and stirring continued for 15 minutes. Triethylamine (15.2 g, 20.9 ml, 150 mM) was added and stirring continued at −78° C. for 3 hours. The solution was washed with 2N HCl, brine, dried ($MgSO_4$) and evaporated to an oil which was purified by silica-gel MPLC (using as eluant 5% MeOH/$CH_2Cl_2$) to give the title ketone (8.36 g, 85%).

NMR (300 MHz, D6-DMSO): δ 0.02 (s, 6H), 0.85 (s, 9H), 1.46 (s, 9H), 2.30 (d, 1H), 2.81–2.97 (m, 1H), 3.41–3.75 (m, 2H), 3.80 (d, 1H) 3.83–3.98 (m, 1H) and 4.27 (t, 1H).

REFERENCE EXAMPLE 13

(2S)-2-tert-Butyldimethylsilyloxymethyl-1-tert-butoxycarbonyl-4-trifluoromethylsulphonyl-2,5-dihydropyrrole The ketone (Reference Example 12, 5.48 g, 16.65 mM) in dry THF (160 ml) at −78° C. was treated with potassium bis(trimethylsilyl)amide (0.5 M in toluene, 38.8 ml, 19.39 mM) and was stirred for 0.5 hours. N-Phenyl-bis(trifluoromethanesulfonamide) (6.92g, 19.39 mM) was added and stirring continued for 4 hours. The mixture was evaporated and the residue purified by silica-gel MPLC (using as eluant a mixture increasing in polarity from 0% to 5% EtOAc in isohexane) to give the title triflate (5.90 g, 77%).

NMR (300 MHz, D6-DMSO): δ 0.01 (s, 6H), 0.82 (s, 9H), 1.40 (s, 9H), 3.62–4.05 (m, 3H), 4.25 (d, 1H), 4.53 (br s, 1H) and 5.96 (d, 1H). MS: (ESP+) 462 (MH+, 43%) and 406 (MH+-isobutylene, 100%).

EXAMPLE 34

N-((5S)-3-(4-(1-tert-Butoxycarbonyl-2S-tert-butyldimethylsilyloxymethyl-2,5-dihydropyrrol-4-yl)phenyl)-2-oxooxazolidin-5-ylmethyl)acetamide The triflate (Reference Example 13, 0.187 g, 0.41 mM), palladium(0) bis(dibenzylideneacetone) (0.020 g, 0.022 mM), triphenylarsine (0.027 g, 0.088 mM) and lithium chloride (0.055 g, 1.32 mM) were dissolved in degassed DMF (5 ml). The oxazolidinone stannane as used in Example 1 (WO Patent 94/13649 A1 (Jun. 23, 1994), 0.175 g, 0.44 mM) was added after 5 minutes and the solution stirred at 40° C. for 18 hours. The mixture was treated with aq. potassium fluoride (2M, 1.0 ml, 2.05 mM) and stirred for 20 minutes. The solution was evaporated to an oil which was dissolved in EtOAc (30 ml) and water (8 ml) and then filtered through Celite. The organic layer was dried ($MgSO_4$) and evaporated to the crude product which was purified by silica-gel MPLC (using as eluant 25% MeCN/EtOAc) to afford the title product (0.163g, 73%) contaminated with small amounts of the methyloxazolidinone.

NMR (300 MHz, D6-DMSO): δ 0.00 (s, 6H), 0.80 (s, 9H), 1.45 (s, 9H), 1.82 (s, 3H), 3.42 (t, 2H), 3.70–3.90 (m, 3H), 4.14 (t, 1H), 4.20–4.35 (m, 1H), 4.45 (d, 1H), 4.57 (br s, 1H), 4.65–4.78 (m, 1H), 6.23 (s, 1H), 7.40–7.55 (m, 4H) and 8.22 (t, 1H), MS: (ESP+) 546 (MH+, 26%) and 490 (MH+-isobutylene, 100%).

EXAMPLE 35

N-((5S)-3-(3-Fluoro-4-(1-tert-Butoxycarbonyl-2S-tert-butyldimethylsilyloxymethyl-2,5-dihydropyrrol-4-yl)phenyl)-2-oxooxazolidin-5-ylmethyl)acetamide The triflate (Reference Example 13, 1.07 g, 2.32 mM), palladium(0) bis(dibenzylideneacetone) (0.110 g, 0.12 mM), triphenylarsine (0.153 g, 0.50 mM) and lithium chloride (0.312 g, 7.44 mM) were dissolved in degassed DMF (30 ml). N-((5S)-3-(3-fluoro-4-trimethyltinphenyl)-2-oxooxazolidin-5-ylmethyl)acetamide (WO Patent 94/13649 A1 (Jun. 23, 1994), 1.03 g, 2.48 mM) was added after 5 minutes and the solution stirred at 40° C. for 4 days. The reaction temperature was then raised to 60° C. for a further 18 hours. The mixture was then treated with aq. potassium fluoride (2M, 6.2 ml, 12.4 mM), stirred for 25 minutes and then filtered through Celite. The solution was evaporated to an oil which was dissolved in EtOAc (30 ml) and water (8 ml). The organic layer was dried ($MgSO_4$) and evaporated to the crude product which was purified by silica-gel MPLC (using as eluant a mixture increasing in polarity from 4% to 10% MeOH in $CH_2Cl_2$, then using as eluant a mixture increasing in polarity from 0% to 10% MeCN in EtOAc) to afford the title product (0.21 g, 17%).

NMR (300 MHz, D6-DMSO): δ 0.00 (s, 6H), 0.80 (s, 9H), 1.45 (s, 9H), 1.84 (s, 3H), 3.40 (t, 2H), 3.70–3.90 (m, 2H), 4.15 (t, 1.5H), 4.23–4.38 (m, 1H), 4.50 (d, 1H), 4.59 (br s, 1H), 4.75 (br t, 1.5H), 6.25 (s, 1H), 7.28–7.61 (m, 3H) and 8.22 (t, 1H). MS: (ESP+) 564 (MH+, 67%).

EXAMPLE 36

N-((5S)-3-(4-(1-tert-Butoxycarbonyl-2S-hydroxymethyl-2,5-dihydropyrrol-4-yl)phenyl)-2-oxooxazolidin-5-ylmethyl)acetamide EXAMPLE34 (0.64 g, 1.17 mM) in dry THF (20 ml) at 0° C. was treated with tetra-n-butylammonium fluoride (1.0M in THF, 5.9 ml, 5.87 mM) and stirred for 3 hours with warming to ambient temperature. The solution was evaporated and the residue purified by silica-gel MPLC (using as eluant 2% MeOH/CH$_2$Cl$_2$) to give the title alcohol (0.444 g, 88%).

NMR (300 MHz, D6-DMSO): δ 1.41 (s, 9H), 1.80 (s, 3H), 3.40 (t, 2H), 3.42–3.50 (m, 1H), 3.64–3.78 (m, 2H), 4.10 (t, 1H), 4.20–4.38 (m, 1H), 4.43 (d, 1H), 4.45–4.58 (m, 1H), 4.70 (t, 2H), 6.29 (s, 1H), 7.45 (d, 2H), 7.52 (d, 2H) and 8.20 (t, 1H). MS: (ESP+) 394 (MH+-isobutylene, 100%) and 450 (MH+, 13%).

EXAMPLE 37

N-((5S)-3-(4-(1-tert-Butoxycarbonyl-2S-tert-butyldiphenylsilyloxymethyl-2,5-dihydropyrrol-4-yl)phenyl)-2-oxooxazolidin-5-ylmethyl)acetamide The alcohol (Example 36, 0.080 g, 0.186 mM) in DMF (2 ml) was treated with tert-butyldiphenylsilyl chloride (0.056 g, 0.053 ml, 0.205 mM) and imidazole (0.025 g, 0.372 mM) and was stirred for 70 hours at ambient temperature. More tert-butyldiphenylsilyl chloride (0.100 ml) and imidazole (0.050 g) was added and stirring continued for another 3 hours. The solution was then diluted with EtOAc (8 ml), washed with 2M HCl, water (2×15 ml), dried (MgSO$_4$) and evaporated to an oil which was purified by silica-gel MPLC (using as eluant 6% MeOH/CH$_2$Cl$_2$) to give the title product (0.080 g, 64%).

NMR (300 MHz, D6-DMSO): δ 0.90 (d, 9H), 1.30 (s, 4.5H), 1.45 (s, 4.5H), 1.80 (s, 3H), 3.40 (t, 2H), 3.70–3.95 (m, 3H), 4.08–4.18 (m, 1H), 4.28–4.40 (m, 1H), 4.50 (d, 1H), 4.58–4.77 (m, 2H), 6.26 (s, 1H), 7.29–7.60 (m, 14H) and 8.20 (t, 1H). MS: (ESP+) 670 (MH+, 100%).

EXAMPLE 38

N-((5S)-3-(4-(1-tert-Butoxycarbonyl-2S-benzoyloxymethyl-2,5-dihydropyrrol-4-yl)phenyl)-2-oxooxazolidin-5-ylmethyl)acetamide The alcohol (Example 36. 0.60 g, 1.41 mM) in dichloromethane (30 ml) at 0° C. was treated with pyridine (0.56 g, 0.57 ml, 7.05 mM) and benzoyl chloride (0.99 g, 0.82 ml, 7.05 mM). The ice-bath was removed immediately and stirring continued for 4.25 hours. The solution was washed with 2M HCl, water, dried (MgSO$_4$) and evaporated to an oil which was purified by silica-gel MPLC (using as eluant 5% MeOH/CH$_2$Cl$_2$) to give after trituration with diethyl ether the title benzoate ester (0.62 g, 83%) as a granular solid.

NMR (300 MHz, D6-DMSO): δ 1.41 (s, 9H), 1.80 (s, 3H), 3.38 (t, 2H), 3.77 (dd, 1H), 4.10 (t, 1H), 4.28–4.43 (m, 1H), 4.48–4.57 (m, 3H), 4.65–4.77 (m, 1H), 4.84–4.95 (m, 1H), 6.30 (s, 1H), 7.40–7.64 (m, 7H), 7.89 (d, 2H) and 8.20 (t, 1H). MS: (ESP+) 480 (MH+-isobutylene, 9%) and 436 (MH+-BOC, 7%).

EXAMPLE 39

N-((5S)-3-(4-(2S-Benzoyloxymethyl-2,5-dihydropyrrol-4-yl)phenyl)-2-oxooxazolidin-5-ylmethyl)acetamide The benzoate ester (Example 38, 0.56 g, 1.05 mM) was dissolved in TFA (4 ml) for 5 minutes before being evaporated at 60° C. The resulting oil was triturated with diethyl ether to give the title amine (0.556 g, 97%).

NMR (300 MHz, D6-DMSO): δ 1.80 (s, 3H), 3.39 (t, 2H), 3.75 (t, 1H), 4.11 (t, 1H), 4.39–4.51 (m, 3H), 4.60–4.78 (m, 2H), 4.99 (br s, 1H), 6.38 (s, 1H), 7.45–7.70 (m, 7H), 7.98 (d, 2H), 8.20 (t, 1H) and 9.62 (br s, 1H), MS: (ESP+) 436 (MH+, 100%).

EXAMPLE 40

N-((5S)-3-(4-(2S-Benzoyloxymethyl-1-cyano-2,5-dihydropyrrol-4-yl)phenyl)-2-oxooxazolidin-5-ylmethyl)acetamide The amine (Example 39, 0.199 g, 0.36 mM) as a suspension in dichloromethane (4 ml) was treated with triethylamine (0.145 g, 0.200 ml, 1.44 mM), 4-dimethylaminopyridine (0.004 g, 0.036 mM) and a suspension of cyanogen bromide (0.192 g, 1.81 mM) in dichloromethane (3 ml). After stirring for 1.25 hours the solution was washed with sat. aq. sodium hydrogen carbonate (3 ml), brine (3 ml), dried and evaporated to a solid which was purified by silica-gel MPLC (using as eluant 3% MeOH/CH$_2$Cl$_2$) to give the title product (0.143 g, 86%).

NMR (300 MHz, D6-DMSO): δ 1.80 (s, 3H), 3.40 (t, 2H), 3.75 (dd, 1H), 4.09 (t, 1H), 4.31 (dd, 1H), 4.58 (dd, 1H), 4.70 (s, 3H), 5.05 (br s, 1H), 6.28 (s, 1H), 7.45–7.69 (m, 7H), 7.98 (d, 2H) and 8.24 (t, 1H). MS: (ESP+) 461 (MH+, 100%).

EXAMPLE 41

N-((5S)-3-(4-(2S-Benzoyloxymethyl-1-formyl-2,5-dihydropyrrol-4-yl)phenyl)-2-oxooxazolidin-5-ylmethyl)acetamide The amine (Example 39, 0.205 g, 0.37 mM) was refluxed in ethyl formate (5 ml) containing triethylamine (0.151 g, 0.208 ml, 1.49 mM) for 6 days. The solution was evaporated and the residue was purified by silica-gel MPLC (using as eluant 4% MeOH/CH$_2$Cl$_2$) to give the title product (0.107 g, 63%) after trituration with diethyl ether.

NMR (250 MHz, D6-DMSO): δ 1.80 (s, 3H), 3.40 (t, 2H), 3.75 (dt, 1H), 4.13 (dt, 1H), 4.30–4.45 (m, 1H), 4.52–4.88 (m, 4H), 5.10–5.25 (m, 1H), 6.30–6.40 (m, 1H), 7.40–7.68 (m, 7H), 7.85–7.97 (m, 2H), 8.20 (t, 1H), 8.37 (s, 0.33H) and 8.43 (s, 0.66H). MS: (ESP+) 464 (MH+, 100%).

EXAMPLE 42

N-((5S)-3-(4-(2S-Hydroxymethyl-2,5-dihydropyrrol-4-yl)phenyl)-2-oxooxazolidin-5-ylmethyl)acetamide Example 34 0.66 g, 1.21 mM) was treated with TFA (2 ml) and warmed to 60° C. for 3 minutes before being evaporated and dissolved in ammonium hydroxide (3 ml) solution. The aqueous solution was washed with diethyl ether and then reduced in volume to remove all traces of organic solvent. The aqueous solution was purified by Mitsubishi HP20 polystyrene resin MPLC (using as eluant a mixture increasing in gradient from 0% to 20% acetonitrile in water) to give the title amine (0.300 g, 75%) after freeze-drying.

NMR (300 MHz, D6-DMSO): δ 1.80 (s, 3H), 3.40 (t, 2H), 3.60 (dd, 2H), 3.70–3.80 (m, 2H), 4.10 (t, 1H), 4.34 (br s, 2H), 4.55 (br s, 1H), 4.65–4.77 (m, 1H), 6.25 (s, 1H), 7.50–7.60 (m, 4H), 8.23 (t, 1H) and 9.15 (br s, 1H). MS: (ESP+) 332 (MH+, 100%).

EXAMPLE 43

N-((5S)-3-(4-(1-Formyl-2S-hydroxymethyl-2,5-dihydropyrrol-4-yl)phenyl)-2-oxooxazolidin-5-ylmethyl)acetamide The amine (Example 42, 0.156 g, 0.47 mM) was refluxed in ethyl formate (5 ml) containing triethylamine (0.192 g, 0.264 ml, 1.90 mM) for 2 days. The precipitate was removed by filtration to give the title product (0.075 g, 44%).

NMR (300 MHz, D6-DMSO): δ 1.80 (s, 3H), 3.40 (t, 2H), 3.55–3.66 (m, 1H), 3.75 (dd, 1H), 4.10 (t, 1H), 4.31 (dd, 1H), 4.53 (d, 1H), 4.65–4.80 (m, 3H), 5.05 (t, 1H), 6.29 (s, 1H), 7.45–7.58 (m, 4H), 8.20 (t, 1H) and 8.30 (s, 1H). MS: (ESP+) 360 (MH+, 100%).

EXAMPLE 44

N-((5S)-3-(4-((7aS)[3H,5H]-3-oxo-1,7a-Dihydropyrrolol[1,2c]oxazol-6-yl)phenyl)-2-oxooxazolidin-5-ylmethyl)acetamide Example 34 (0.120 g, 0.22 mM) was treated with TFA (1 ml) and warmed to 60° C. for 2 minutes before being evaporated to a gum which was triturated with diethyl ether to give the TFA salt of the amine Example 42 (0.059 g). This was suspended in dichloromethane (2 ml) and treated with triethylamine (0.040 g, 0.056 ml, 0.400 mM) followed by 1,1'-carbonyl diimidazole (0.032 g, 0.200 mM). The solution was stirred for 2.5 hours and then more triethylamine (0.050 ml) and 1,1'-carbonyl diimidazole (0.020 g) was added. After stirring for a further 18 hours the solution was diluted with dichloromethane and washed with 2M HCl. The organic layer was dried (MgSO$_4$), evaporated to a solid and purified by silica-gel Isolute chromatography (using as eluant 4% MeOH/CH$_2$Cl$_2$) to give the title product (0.016 g, 34%).

NMR (300 MHz, D6-DMSO): δ 1.82 (s, 3H), 3.43 (t, 2H), 3.76 (dd, 1H), 4.07–4.20 (m, 2H), 4.32 (dd, 1H), 4.55 (br d, 1H), 4.62 (t, 1H), 4.67–4.79 (m, 1H), 4.85–4.95 (m, 1H), 6.43 (d, 1H), 7.55 (s, 4H) and 8.20 (t, 1H). MS: (ESP+) 358 (MH+, 100%).

REFERENCE EXAMPLE 14

N-((5S)-3-(3-Fluoro-4-(1-tert-butoxycarbonyl-2S-hydroxymethyl-2,5-dihydropyrrol-4-yl)phenyl)-2-oxooxazolidin-5-ylmethyl)acetamide Example 35 (0.159 g, 0.28 mM) in dry THF (5 ml) at 0° C. was treated with tetra-n-butylammonium fluoride (1.0M in THF, 1.41 ml, 1.41 mM) and stirred for 2 days with warming to ambient temperature. The solution was treated with water (0.5 ml), evaporated and the residue purified by silica-gel MPLC (using as eluant 3% MeOH/CH$_2$Cl$_2$) to give the title alcohol (0.090 g, 72%).

NMR (300 MHz, D6-DMSO): δ 1.44 (s, 9H), 1.84 (s, 3H), 3.43 (t, 2H), 3.45–3.57 (m, 1H), 3.64–3.80 (m, 2H), 4.13 (t, 1H), 4.26–4.62 (m, 3H), 4.67–4.80 (m, 2H), 6.33 (s, 1H), 7.30 (dd, 1H), 7.38–7.60 (m, 2H) and 8.23 (t, 1H). MS: (ESP) 450 (MH+, 13%) and 394 (MH+-isobutylene, 100%).

EXAMPLE 45

N-((5S)-3-(3-Fluoro-4-((7aS)[3H,5H]-3-oxo-1,7a-dihydropyrrolo[1,2c]oxazol-6-yl)phenyl)-2-oxooxazolidin-5-ylmethyl)acetamide The alcohol (Reference Example 14, 0.088 g, 0.20 mM) was treated with TFA (1 ml) and warmed to 60° C. for 2 minutes before being evaporated to a gum which was triturated with diethyl ether. The ether was decanted off and the hygroscopic salt dried in a stream of argon to give the TFA salt of the amine (0.120 g). The salt (0.120 g, 0.26 mM) was suspended in dichloromethane (2 ml) and treated with triethylamine (0.130 g, 0.180 ml, 1.30 mM) followed by 1,1'-carbonyl diimidazole (0.211 g, 1.30 mM). The solution was stirred for 18 hours at ambient temperature and then diluted with dichloromethane and washed with 2M HCl. The organic layer was dried (MgSO$_4$), evaporated to a solid and triturated with diethyl ether to give the title product (0.016 g, 21%).

NMR (300 MHz, D6-DMSO): δ 1.82 (s, 3H), 3.42 (t, 2H), 3.75 (dd, 1H), 4.08–4.21 (m, 2H), 4.37 (m, 1H), 4.53–4.66 (m, 2H), 4.67–4.80 (m, 1H), 4.84–4.94 (m, 1H), 6.48 (s, 1H), 7.34 (dd, 1H), 7.46–7.61 (m, 2H) and 8.23 (t, 1H). MS: (ESP+) (ESP+) 376 (MH+, 100%).

REFERENCE EXAMPLE 15

4-Nitrophenyl-(trimethylsilyl)-acetylene
(*J.Med. Chem.* 1990, 33, 2574).

A 3-necked flask was charged with triethylamine (100 ml) and anhydrous DMF (100 ml) and flushed with argon for 30 minutes. To the solution was added p-iodo-nitrobenzene (10.0 g; 40 mM), trimethylsilyl-acetylene (7 ml; 4.87 g; 50 mM), CuI (100 mg; 0.5 mM) and Pd(PPh$_3$)$_2$Cl$_2$ (700 mg; 1 mM). The mixture was heated at 45° C. with stirring under an argon atmosphere and was found to have gone to completion after 3 hours. The reaction mixture was concentrated by rotary evaporation under high vacuum to an oil which was then redissolved in EtOAc/i-hexane and heated with decolourising charcoal for 20 minutes before filtering while still hot. The filtrate was then concentrated by rotary evaporation under reduced pressure to afford a crystalline, but impure and oily solid, p-nitrophenyl-(trimethylsilyl)-acetylene, (12.5 g; 142%).

NMR (300 MHz, DMSO-D6): δ 0.00 (s, 9H), 7.46 (d, 2H), 7.94 (d, 2H).

REFERENCE EXAMPLE 16

4-Nitrophenylacetylene
(*J.Med. Chem.* 1990, 33, 2574).

A solution of Reference Example 15 (12.5 g, crude) in methanol (200 ml) was treated with aq. KOH (1N, 25 ml) and stirred at ambient temperature for 1 hour. The methanol was then removed by rotary evaporation under reduced pressure and the resulting aqueous suspension treated with 1N HCl and extracted with dichloromethane. The two phase mixture was then filtered through Celite and the organic extracts from the filtrate dried over MgSO$_4$, filtered and concentrated down by rotary evaporation to a solid. Purification of the solid by MPLC on silica, using as eluant a mixture increasing in polarity from 10% to 20% EtOAc in i-hexane gave 5.16 g (87% over two stages) of solid p-(nitrophenyl)-acetylene.

NMR (300 MHz, DMSO-D6): δ 4.68 (s, 1H), 7.72 (d, 2H), 8.12 (d, 2H).

REFERENCE EXAMPLE 17

1-Benzyl-4RS-benzyloxymethyl-3RS-(4-nitrophenyl)-azetidin-2-one
(*Method of J. Org. Chem.* 1995, 60, 4999–5004)

A 3-necked flask was charged with ethanol (200 ml) and flushed with argon for 15 minutes before adding anhydrous pyridine (8 ml; 7.8 g; 99 mM), benzyloxyacetaldehyde (5.1 ml; 5.45 g; 36 mM) and N-benzylhydroxylamine hydrochloride (6.4 g; 40 mM). The solution was stirred under argon at ambient temperature for 1 hour then treated with K$_2$CO$_3$ (4.16 g; 30 mM), CuI (640 mg; 3.4 mM) and a solution of Reference Example 16 (4.0 g; 27 mM) in anh. DMF (40 ml) and anh. pyridine (40 ml). The resulting cloudy solution was stirred under argon at ambient temperature for 22 hours. The reaction mixture was then concentrated down by rotary evaporation to an oil which was treated with 1N HCl and extracted with EtOAc. The organic phase was washed with saturated brine. dried over $MgSO_4$, filtered and concentrated down by rotary evaporation to give a viscous oil. The oil was purified by MPLC on silica (using a gradient elution from i-hexane to 60% EtOAc in i-hexane) to yield a mixture (6.5 g, 59%) of the beta-lactam cis/trans isomers as an oil.

NMR (300 MHz, DMSO-D6): δ 3.69 (m, 2H), 3.79 (m, 1H), 4.26 (d, 1H), 4.42 (s, 3H), 4.57 (d, 1H), 7.22 (m, 10H), 7.51 (d, 2H), 8.18 (d, 2H), MS: ESP+ (M+H)=403.5, IR ($cm^{-1}$): u (C=O stretch): 1749.7.

REFERENCE EXAMPLE 18

1-Benzyl-2RS-benzyloxymethyl-3RS-(4-nitrophenyl)-azetidine

Anhydrous AlCl, (6.7 g; 50 mM) and $LiAlH_4$ (1.9 g; 50 mM) were suspended in anh. diethyl ether (250 ml) and heated at reflux temperature for 30 minutes. The solution was then treated with a solution of Reference Example 17 (6.7 g; 16.7 mM) in anh. diethyl ether (180 ml) over 5 minutes. The resulting suspension was stirred and heated at reflux temperature for 1.5 hours. After allowing to cool to ambient temperature the reaction mixture was treated carefully with water and extracted with dichloromethane. The organic extracts were washed with water and sat. brine, dried over $MgSO_4$, filtered and evaporated down to an oil. The oil was purified by MPLC on silica (using a gradient of i-hexane through to EtOAc as eluant) to obtain three products eluting in the following order:

18A:—360 mg (6%) of an oil, the cis-nitrophenyl azetidine; 18B:—2.0 g (31%) of an oil, the trans-nitrophenyl azetidine; and 18C:—1.25 g (21%) of an oil, the anilino azetidine.

18A: NMR (300 MHz, DMSO-D6): δ 2.66 (dd, 1H), 2.93 (d, 1H), 3.02 (dd, 1H), 3.36 (m, 1H), 3.56 (d, 1H), 3.78 (m, 2H), 3.82 (d, 1H), 4.01 (d, 1H), 4.18 (d, 1H), 7.28 (m, 10H), 7.65 (d, 2H), 8.18 (d, 2H), MS: ESP+ (M+H)=389.5.

18B: NMR (300 MHz, DMSO-D6): δ 2.66 (dd, 1H), 2.93 (d, 1H), 3.02 (dd, 1H), 3.36 (m, 1H), 3.56 (d, 1H), 3.78 (m, 2H), 3.82 (d, 1H), 4.01 (d, 1H), 4.18 (d, 1H), 7.28 (m, 10H), 7.65 (d, 2H), 8.18 (d, 2H), MS: ESP+ (M+H)=389.5.

18C: MS: ESP+ (M+H)=359.6.

REFERENCE EXAMPLE 19

(trans)-1-Benzyl-2RS-benzyloxymethyl-3RS-(4-aminophenyl)-azetidine

The trans-nitrophenyl azetidine (18B of Reference Example 18, 1.84 g; 4.7 mM) and stannous chloride dihydrate (5.8 g; 25.7 mM) were suspended in ethanol (50 ml) and heated at 70° C. under argon for 2 hours. The reaction mixture was allowed to cool to ambient temperature and basified with conc.aq. $NH_4OH$ to form a slurry. The slurry was treated with EtOAc and the two phase mixture filtered through Celite. The organic phase of the filtrate was then washed with sat. brine, dried over $MgSO_4$, filtered, and rotary evaporated down to give the title mixture of trans isomers as an oil (1.46 g, 86%). MS: ESP+ (M+H)=359.5.

REFERENCE EXAMPLE 20

(trans)-1-Benzyl-2RS-benzyloxymethyl-3RS-(4-benzyloxycarbonylamino-phenyl)-azetidine A solution was prepared containing $NaH_2PO_4$. $2H_2O$ (3.48 g; 22.3 mM) in water (30 ml) and acetone (30 ml) and was treated simultaneously with two solutions at equivalent rates—the one, Reference Example 19 (2.56 g; 7.1 mM) and conc. HCl (0.6 ml; 7.2 mM) in acetone (170 ml) and the other, benzyl chlororformate (1.25 ml; 1.49 g; 8.7 mM) in acetone (170 ml) over 30 minutes in an ice bath. The reaction mixture was stirred and allowed to reach ambient temperature over 18 hours. The reaction mixture was then concentrated to an aqueous suspension by rotary evaporation, which was basified with conc. aq. $NH_4OH$ and extracted with dichloromethane. The organic phase was washed with sat. brine, dried over $MgSO_4$, filtered and concentrated down by rotary evaporation under reduced pressure to an oil. The oil was purified by MPLC on silica, (using as eluant a mixture increasing in polarity from 0% to 12% MeOH in $CH_2Cl_2$) to obtain the title mixture of trans isomers as a viscous oil (3.41 g, 93%).

NMR (300 MHz DMSO-D6): δ 2.85 (t, 1H), 3.17 (d, 1H), 3.46 (m, 5H), 3.83 (d, 1H), 4.44 (dd, 2H), 5.16 (s, 2H), 7.29 (m, 19H), 9.64 (s, 1H), MS: ESP+ (M+H)=493.5.

REFERENCE EXAMPLE 21

5R-Hydroxymethyl-3-(4-(1-Benzyl-2RS-benzyloxymethyl)azetidin-3RS-yl)phenyloxazolidin-2-one A solution of Reference Example 20 (3.35 g; 6.8 mM) in anh. THF (100 ml) was flushed with argon then enclosed in an argon atmosphere and stirred in a $CO_2$-acetone cooling bath. With the internal temperature (int. T.) at −74° C. the solution was treated, slowly, with 1.43M nBuLi in hexanes (4.75 ml; 6.8 mM) maintaining the int. T. at <−68° C. throughout the addition. The solution of the anion was stirred at an int. T. of ~−72° C. for 20 minutes then treated, dropwise, with a solution of (R)-glycidyl butyrate (0.95 ml; 980 mg; 6.80 mM) in anh. THF (40 ml). After the addition the reaction mixture was allowed to warm to ambient temperature without removing the cooling bath and thus stirred for the following 48 hours. The reaction mixture was then treated with methanol (10 ml) and stirred at ambient temperature for a further 20 minutes before concentrating down to an oil by rotary evaporation under reduced pressure. The oil was treated with 2N aq. $NH_4Cl$ and extracted with EtOAc and thereafter the organic phase was washed with sat. brine, dried over $MgSO_4$, filtered and evaporated down to an oil. The oil was purified by MPLC on silica (using as eluant 10% MeOM in $CH_2Cl_2$) to give as an oil, the title hydroxymethyloxazolidinone as a mixture of trans azetidine isomers, 2.54 g (81%).

NMR: (300 MHz, DMSO-D6): δ 2.90 (t, 1H), 3.16 (d, 1H), 3.22 (partly obscured by $H_2O$ from dmso), (m, 1H), 3.38 (t, 2H), 3.43 (s, 2H), 3.58 (m, 2H), 3.62 (m, 1H), 3.80 (dd, 1H), 4.04 (t, 1H), 4.41 (dd, 2H), 4.64 (m, 1H), 5.18 (t, 1H), 7.23 (m, 12H), 7.45 (d, 2H). MS: ESP+ (M+H)=459.5.

REFERENCE EXAMPLE 22

N-tert-Butoxycarbonyl-N-((5R)-3-(4-(1-Benzyl-2RS-benzyloxymethyl-azetidin-3RS-yl)phenyl-2-oxooxazolidin-5-ylmethyl)acetamide A solution of Reference Example 21 (2.53 g; 5.53 mM) in anh. THF (60 ml) was flushed with argon then stirred at ambient temperature under argon and treated with N-Boc-acetamide (Chem.Pharm.Bull.Jap.,36, 3125(1988), 1.32 g; 8.3 mM). The solution was then cooled to an internal temperature of 0° C. (ice-NaCl bath). Whilst at this temperature the solution was treated with "$Bu_3P$ (2.1 ml; 1.72 g;

8.5 mM) and 1,1'-(azodicarbonyl)-dipiperidine (2.1 g; 8,3 mM). After approximately 5 minutes of stirring the mixture at 0° C., a precipitate formed. Stirring was continued for a further 40 minutes at 0–2° C. before removing the cooling bath and allowing stirring to continue at ambient temperature for the next 20 hours. After this time the reaction mixture was filtered to remove the precipitate and the filtrate evaporated down to a semi-solid. The impure semi-solid was purified by MPLC on silica (using as eluant 10% MeOH in $CH_2Cl_2$) to give as an oil the title N-BOC-acetamido oxazolidinone (900 mg, 27%) as a mixture of trans azetidine isomers. MS: ESP+ (M+H)=600.5.

EXAMPLE 46

N-((5S)-3-(4-(1-Benzyl-2RS-benzyloxymethyl-azetidin-3-yl)phenyl-2-oxooxazolidin-5-ylmethyl)acetamide A solution of Reference Example 22 (900 mg, 1.5 mM) in $CH_2Cl_2$ (5 ml) was treated at ambient temperature with TFA (2.3 ml; 30 mM) and the solution stirred for 20 minutes. The reaction mixture was basified with conc. aq. $NH_4OH$ and extracted with dichloromethane. The organic extracts were washed with water and sat. brine, dried over $MgSO_4$, filtered and evaporated down to a viscous oil. The oil was purified by MPLC on silica (using as eluant 8% MeOH in $CH_2Cl_2$) to give a gum. Trituration of the gum failed to yield a solid so it was redissolved in EtOAc and acidified with 4.35M HCl/EtOAc to form a precipitate which was triturated with diethyl ether. Decanting off the liquor and drying the solid by rotary evaporation, then heating in an evacuated drying pistol yielded 150 mg (20%) of the title product as the hydrochloride salt of a mixture of trans azetidine isomers.

NMR (300 MHz, DMSO-D6): δ 1.81 (s, 3H), 3.40 (t, 2H) (partly obscured by $H_2O$ from DMSO), 3.49 (dd, 1H), 3.78 (m, 2H), 3.82 (q, 1H), 4.12 (m, 3H), 4.47 (s, 4H), 4.70 (m, 2H), 7.40 (m, 14H), 8.21 (t, 1H). MS: ESP+ (M+H)=500.5.

Elemental Analysis: As HCl salt, $C_{30}H_{34}ClN_3O_4$ requires C, 67.22; H, 6.39; N, 7.84%. Found: C, 64.6; H, 6.6; N, 7.1%. HCl salt with 1.20 equivalents of $H_2O$ requires C: 64.6; H: 6.58; N: 7.53%.

REFERENCE EXAMPLE 23

3,5-Difluoro-N-benzyloxycarbonylaniline 3,5-Difluoroaniline (4.89 g, 37 91 mM) in acetone (130 ml) and water (70 ml) at 0° C. was treated with sodium hydrogen carbonate (6.55 g, 78.0 mM) and then benzyl chloroformate (6.67 g, 5.6 ml, 39.23 mM) over 10 min. The mixture was stirred for 16 h and then poured into ice. The resultant precipitate was collected and washed with water to give the title carbamate (9.35 g, 94%);

NMR (250 MHz, D6-DMSO): δ 5.09 (s, 2H), 6.74 (tt, 1H), 7.02–7.13 (m, 2H) and 7.20–7.37 (m, 5H), MS: (ESP+) 264 (MH+, 46%).

REFERENCE EXAMPLE 24

5R-Hydroxymethyl-3-(3,5-difluorophenyl)oxazolidin-2-one

A solution of the carbamate (Reference Example 23) (4.22 g, 16 mM) in dry THF (50 ml) at −78° C. was treated with n-butyl lithium (1.38M in hexanes, 11.7 ml, 16.1 mM) and stirred for 25 min. (R)-Glycidyl butyrate (2.33 g, 2.29 ml, 16.2 mM) was added dropwise and stirring continued for 5 days. Methanol (20 ml) was added and stirring continued for 25 min. Ammonium chloride (100 ml) was added and the mixture extracted with ethyl acetate (3×120 ml). The organics were dried ($MgSO_4$) and evaporated to the crude product which was purified by silica-gel MPLC [using 4% MeOH/$CH_2Cl_2$ as eluant] to give the title alcohol (3.00 g, 82%);

NMR (300 MHz, D6-DMSO): δ 3.55 (dt, 1H), 3.67 (ddd, 1H), 3.82 (dd, 1H), 4.05 (t, 1H), 4.66–4.78 (m, 1H), 5.20 (t, 1H), 6.96 (t, 1H) and 7.30 (d, 2H). MS: (ESP+) 230 (MH+, 100%).

REFERENCE EXAMPLE 25

5R-Methanesulfonyloxymethyl-3-(3,5-difluorophenyl)oxazolidin-2-one

The alcohol (Reference Example 24) (2.95 g, 12.9 mM) in dichloromethane (70 ml) at 0° C. was treated with triethylamine (2.6 g, 3.6 ml, 25.9 mM) followed by mesyl chloride (2.10 g, 1.42 ml, 18.3 mM) and then stirred for 2 h. The cloudy solution was diluted with dichloromethane and washed successively with 2N HCl, aqueous sodium hydrogen carbonate and water. The organics were dried ($MgSO_4$) and evaporated to give the title mesylate (3.89 g, 98%);

NMR (300 MHz, D6-DMSO): δ 3.25 (s, 3H), 3.83 (dd, 1H), 4.18 (t, 1H), 4.41–4.55 (m, 2H), 4.97–5.09 (m, 1H), 6.94–7.08 (m, 1H) and 7.30 (d, 2H). MS: (ESP+) 308 (MH+, 100%).

REFERENCE EXAMPLE 26

5R-Azidomethyl-3-(3,5-difluorotphenyl)oxazolidin-2-one

The mesylate (Reference Example 25) (3.85 g, 12.5 mM) in dimethylsulfoxide (15 ml) containing sodium azide (1.22 g, 18.8 mM) was heated at 80° C. for 2 h. The cloudy solution was cooled, diluted with water (70 ml) and extracted with dichloromethane (2×40 ml). The organic extracts were washed with water, dried ($MgSO_4$) and evaporated to give the title azide (2.92 g, 92%);

NMR (300 MHz, D6-DMSO): δ 3.64–3.85 (m, 3H), 4.12 (t, 1H), 4.85–4.96 (m, 1H), 6.93–7.05 (m, 1H) and 7.30 (d, 2H). MS: (ESP+) 255 (MH+, 100%).

REFERENCE EXAMPLE 27

N-((5S)-3-(3,5-Difluorophenyl)-2-oxooxazolidin-5-ylmethyl)acetamide

To a stirred solution of the azide (Reference Example 26, 2.85 g, 11.2 mM) in dimethoxyethane (22 ml) at 50° C. under argon was slowly added trimethyl phosphite (1.66 g, 1.58 ml, 13.4 mM) and the mixture was refluxed for 2.25 h. 6N HCl (2.4 ml, 14.3 mM) was added and reflux continued overnight. The solution was then cooled and evaporated to give the crude amine. The amine (11.2 mM) in THF (20 ml) and water (5 ml) was adjusted to pH 8 with aqueous sodium hydroxide. With cooling to ambient temperature, acetic anhydride (2.07 g, 1.91 ml, 20 mM) was added and the mixture stirred for 2 h. The mixture was then diluted with ethyl acetate (50 ml), washed with 2N hydrochloric acid, aqueous sodium hydrogen carbonate and water. The organic layer was dried ($MgSO_4$) and evaporated to a residue which was purified by silica-gel MPLC [using 4% MeOH/$CH_2Cl_2$ as eluant] to give the title product (1.79 g) after trituration with diethyl ether;

NMR (300 MHz, D6-DMSO): δ 1.81 (s, 3H), 3.40 (t, 2H), 3.72 (dd, 1H), 4.10 (t, 1H), 4.68–4.80 (m, 1H), 6.97 (t, 1H), 7.29 (d, 2H) and 8.20 (t, 1H). MS: (ESP+) 271 (MH+, 100%).

REFERENCE EXAMPLE 28

N-((5S)-3-(3,5-Difluoro-4-iodophenyl)-2-oxooxazolidin-5-ylmethyl)acetamide

The difluoro oxazolidinone (Reference Example 27, 1.21 g, 4.48 mM) in acetonitrile (8 ml) and chloroform (8 ml) under argon was treated with silver trifluoroacetate (1.78 g, 8.07 mM) and then iodine (1.71 g, 6.72 mM) portionwise. The mixture was stirred for 4 days. The solution was partitioned between ethyl acetate and water, filtered and the organic layer evaporated to dryness. The resultant solid was purified by silica-gel MPLC [using 2% MeOH/$CH_2Cl_2$ as eluant] to give the title iodide (1.19 g, 67%) after trituration with diethyl ether;

NMR (300 MHz, D6-DMSO) δ 1.80 (s, 3H), 3.40 (t, 2H), 3.70 (dd, 1H), 4.10 (t, 1H), 4.68–4.79 (m, 1H), 7.37 (d, 2H) and 8.19 (t, 1H). MS: (ESP+) 397 (MH+, 100%).

REFERENCE EXAMPLE 29

(2S,4R)-2-Tert-butyldimethylsilyloxymethyl-1-tert-butoxycarbonyl-4-trimethylstannyl-2,5-dihydropyrrole To a suspension of lithium carbonate (0.21 g, 2.84 mM) and lithium chloride (0.846 g, 20.14 mM) in THF (50 ml) under argon was added a solution of the vinyl triflate (Reference Example 13, 1.31 g, 2.84 mM) in THF (20 ml). The mixture was heated to gentle reflux and after 30 min, a solution of hexamethylditin (0.930 g, 0.59 ml, 2.84 mM) in dry THF (20 ml) added, followed by palladium tetrakistriphenylphosphine (0.329 g, 0.284 mM). The mixture was heated at 70° C. for 24 h. The solution was then evaporated and purified by silica-gel MPLC [using 4% EtOAc/isohexane as eluant] to give the title vinyl stannane (0.79 g, 58%);

NMR (300 MHz, D6-DMSO): δ 0.00 (s, 6H), 0.20 (t, 9H), 0.89 (s, 9H), 1.45 (s, 9H), 3.65–3.90 (m, 2H), 3.91–4.09 (m, 1H), 4.20 (d, 1H) 4.43 (br s, 1H) and 5.87 (s, 1H).

REFERENCE EXAMPLE 30

N-((5S)-3-(3,5-Difluoro-4-(1-tert-Butoxycarbonyl-2S-tert-butyldimethylsilyloxymethyl-2,5-dihydropyrrol-4-yl)phenyl)-2-oxooxazolidin-5-ylmethyl)acetamide The iodide (Reference Example 28, 0.701 g, 1.77 mM), palladium(0) bis(dibenzylideneacetone) (0.152 g, 0.166 mM), triphenylarsine (0.102 g, 0.332 mM) and lithium chloride (0.209 g, 4.98 mM) were dissolved in degassed N,N-dimethylformamide (20 ml). The stannane (Reference Example 29) (0.79 g, 1.66 mM) in degassed N,N-dimethylformamide (10 ml) was added after 5 minutes and the solution stirred at 55° C. for 4 days. The solution was evaporated to an oil which was dissolved in ethyl acetate (30 ml) and water (8 ml), treated with aqueous potassium fluoride (2M) (16.6 ml, 8.30 mM), stirred for 30 minutes and then filtered through Celite. The organic layer was washed with water (2×10 ml), dried ($MgSO_4$) and evaporated to the crude product which was purified by silica-gel MPLC [using as eluant a mixture increasing in polarity from 60% to 100% EtOAc in isohexane] to afford the title product (0.682 g, 71%);

NMR (300 MHz, $CDCl_3$): δ 0.08 (s, 6H), 0.87 (s, 9H), 1.50 (s, 9H), 2.05 (s, 3H), 3.60–4.08 (m, 7H), 3.35–4.86 (m, 4H), 6.30 (br s, 1H), 6.65–6.80 (m, 1H) and 7.15 (d, 1H).

REFERENCE EXAMPLE 31

N-((5S)-3-(3,5-Difluoro-4-(1-tert-Butoxycarbonyl-2S-hydroxymethyl-2,5-dihydropyrrol-4-yl)phenyl)-2-oxooxazolidin-5-ylmethyl)acetamide The silyl ether (Reference Example 30, 0.719 g, 1.24 mM) in dry THF (20 ml) at 0° C. was treated with tetrabutylammonium fluoride (1.0M in THF) (6.21 ml, 6.21 mM) and stirred for 2.5 h with warming to ambient temperature. Water (1 ml) was added, the solution was evaporated and the residue purified by silica-gel MPLC [using as eluant a mixture increasing in polarity from 2% to 5% MeOH in $CH_2Cl_2$] to give the title alcohol (0.38 g, 66%);

NMR (300 MHz, D6-DMSO): δ 1.41 (s, 9H), 1.80 (s, 3H), 3.39 (t, 2H), 3.45–3.56 (m, 1H), 3.65–3.77 (m, 2H), 4.10 (t, 1H), 4.25–4.58 (m, 3H), 4.73 (br s, 2H), 6.30 (s, 1H), 7.36 (d, 2H) and 8.18 (t, 1H). MS: (ESP+) 468 (MH+, 12%) and 412 (MH+-isobutylene, 100%).

REFERENCE EXAMPLE 32

N-((5S)-3-(3,5-Difluoro-4-(2S-hydroxymethyl-2,5-dihydropyrrol-4-yl)phenyl)-2-oxooxazolidin-5-ylmethyl)acetamide The alcohol (Reference Example 31, 0.359 g, 0.77 mM) was dissolved in TFA (3 ml) and refluxed for 2 min, before being evaporated at 60° C. The resulting oil was triturated with diethyl ether, the ether decanted off and the resulting powder dried in a stream of argon and then in vacuo to give the title amine salt (0.469 g, >100%);

NMR (300 MHz, D6-DMSO): δ 1.83 (s, 3H), 3.40 (t, 2H), 3.62 (dd, 1H), 3.73 (dd, 1H), 3.80 (dd, 1H), 4.10 (t, 1H), 4.30 (br s, 2H), 4.55 (br s, 1H), 4.70–4.82 (m, 1H), 6.29 (s, 1H), 7.40 (d, 2H), 8.20 (t, 1H), 9.05–9.18 (m, 1H) and 9.62–9.75 (m, 1H). MS: (ESP+) 368 (MH+, 100%).

EXAMPLE 47

N-((5S)-3-(3,5-Difluoro-4-((7aS)[3H,5H]-3-oxo-1,7a-dihydropyrrolo[1,2c]oxazol-6-yl)phenyl)-2-oxooxazolidin-5-ylmethyl)acetamide The salt (Reference Example 32, 0.469 g, 0.98 mM) was suspended in dichloromethane (12 ml) and treated with triethylamine (0.59 g, 0.81 ml, 5.90 mM) at 0° C. The mixture was sonicated for 5 min until the amine had dissolved. 1,1'-Carbonyl diimidazole (0.79 g, 4.90 mM) was added and the solution stirred for 18 h. The solution was diluted with dichloromethane and washed with 2M HCl. The organic layer was dried ($MgSO_4$), evaporated to a solid and purified by silica-gel MPLC[using as eluant a mixture increasing in polarity from 2% to 5% MeOH in $CH_2Cl_2$] to give the title product (0.065 g, 17%), NMR (300 MHz, D6-DMSO): δ 1.81 (s, 3H), 3.40 (t, 2H), 3.72 (dd, 1H), 4.10 (t, 1H), 4.12–4.20 (m, 1H), 4.37 (dd, 1H), 4.52 (d, 1H), 4.60 (t, 1H), 4.70–4.80 (m, 1H), 4.81–4.90 (m, 1H), 6.49 (s, 1H), 7.38 (d, 2H) and 8.20 (t, 1H). MS: (ESP+) 394 (MH+, 100%).

REFERENCE EXAMPLE 33

N-((5S)-3-(4-(1-Tertbutoxycarbonyl-2S-phthalimidomethyl-2,5-dihydropyrrol-4-yl)phenyl)-2-oxooxazolidin-5-ylmethyl)acetamide The alcohol (Reference Example 31, 0.215 g, 0.5 mM), phthalimide (0.076 g, 0.52 mM) and triphenylphosphine (0.136 g, 0.53 mM) in dry THF (4 ml) at 0° C. under argon was treated dropwise with diisopropyl azodicarboxylate (0.135 g, 0.132 ml, 0.67 mM) dropwise. The mixture was allowed to warm to ambient temperature with the ice-bath in place and the solution stirred for 48 h The solution was then evaporated and the residue purified by silica-gel MPLC [using 4% MeOH/$CH_2Cl_2$ as eluant]. The first-eluted material was identified as the amide (0.100 g, 36%) and the second-eluted material was recovered starting material (0.148 g, 69%). This was treated with phthalimide (0.114 g, 0.78 mM) and triphenylphosphine (0.204 g, 0.795 mM) in dry THF (3 ml) at 0° C. under argon was treated dropwise with dilsopropyl azodicarboxylate (0.203 g, 0.198 ml, 1.01 mM) dropwise. The mixture was allowed to warm to ambient temperature with the ice-bath in place and the solution stirred for 60 h. The solution was then evaporated and the residue purified by silica-gel MPLC [using 4% MeOH/CH$_2$Cl$_2$ as eluant]. The combined products gave the title amide (0.256 g, 92%);

NMR (300 MHz, CDCl$_3$): δ 1.48 (s, 4.5H), 1.56 (s, 4.5H), 2.01 (s, 3H), 3.54–3.63 (m, 2H), 3.77 (t, 1H), 3.83–3.99 (m, 1H), 4.05 (t, 1H), 4.10–4.29 (m, 2H), 4.45 (d, 0.5H), 4.57 (d, 0.5H), 4.71–4.82 (m, 1H), 4.94 (br s, 0.5H), 5.09 (br s, 0.5H), 6.02 (d, 1H), 6.45 (br s, 1H), 7.30 (d, 2H), 7.45 (d, 2H), 7.62–7.73 (m, 2H) and 7.78–7.84 (m, 2H), MS: (ESP+) 561 (MH+, 8%) and 505 (MH+-isobutylene, 20%).

REFERENCE EXAMPLE 34

N-((5S)-3-(4-(1-Tertbutoxycarbonyl-2S-aminomethyl-2,5-dihydropyrrol-4-yl)phenyl)-2-oxooxazolidin-5-ylmethyl)acetamide The phthalimide (Reference Example 33, 0.238 g, 0.426 mM) in 40% aqueous methylamine (13 ml) and ethanol (26 ml) was refluxed for 1.5 h. The solution was then evaporated to an oil which was purified by silica-gel MPLC [using 89%CH$_2$Cl$_2$/10% MeOH/1% NH$_4$OH as eluant] to afford the title amine (0.134 g, 73%);

NMR (300 MHz, CDCl$_3$): δ 1.51 (s, 9H), 2.02 (s, 3H), 2.84–2.97 (m, 1H), 3.05–3.20 (m, 1H), 3.57–3.75 (m, 2H), 3.83 (dd, 1H), 4.07 (t, 1H), 4.38–4.84 (m, 4H), 6.05 (d, 1H), 6.57 (t, 1H), 7.40 (d, 2H) and 7.51 (d, 2H). MS: (ESP+) 375 (MH+-isobutylene, 100%) and 431 (MH+, 20%).

REFERENCE EXAMPLE 35

N-((5S)-3-(4-(2S-Aminomethyl-2,5-dihydronyrrol-4-yl)phenyl)-2-oxooxazolidin-5-ylmethyl)acetamide The amine (Reference Example 34, 0.134 g, 0.31 mM) was dissolved in trifluoroacetic acid (2 ml) and refluxed for 2 min. before being evaporated at 60° C. The resulting oil was triturated with diethyl ether, the ether decanted off and the resulting powder dried in a stream of argon and then in vacuo to give the title amine as a salt (0.190 g, >100%);

NMR (300 MHz, D6-DMSO): δ 1.80 (s, 3H), 3.20 (dd, 1H), 3.30 (dd, 1H), 3.40 (t, 2H), 3.76 (dd, 1H), 4.11 (t, 1H), 4.38 (d, 1H), 4.48 (d, 1H), 4.66–4.80 (m, 2H), 6.30 (s, 1H), 7.53 (d, 2H), 7.60 (d, 2H), 8.02–8.35 (br s, 2H) and 8.21 (t, 1H). MS: (ESP+) 331 (MH+, 100%).

EXAMPLE 48

N-((5S)-3-(4-((7aS)[5H]-3-oxo-1,2,3,7a-Tetrahydropyrrolo[1,2c]imidazol-6-yl)phenyl)-2-oxooxazolidin-5-ylmethyl)acetamide The salt (Reference Example 35, 0.186 g, 0.333 mM) was suspended in dichloromethane (4 ml) and treated with triethylamine (0.404 g, 0.56 ml, 4.00 mM) at 0° C. 1,1'-Carbonyl diimidazole (0.270 g, 1.67 mM) was added portionwise over 2 h and the solution stirred for 4 h. The solution evaporated to a solid and purified by silica-gel MPLC[using as eluant a mixture increasing in polarity from 2% to 5% MeOH in CH$_2$Cl$_2$] to give the title product (0.079 g, 67%);

NMR (300 MHz, D6-DMSO): δ 1.83 (s, 3H), 3.42 (t, 2H), 3.47 (s, 2H), 3.76 (dd, 1H), 4.13 (t, 1H), 4.58 (d, 1H), 4.65–4.77 (m, 1H), 4.83–4.96 (m, 1H), 5.12 (s, 1H), 6.20 (s, 1H), 7.20–7.29 (m, 1H), 7.47–7.58 (m, 4H) and 8.20 (t, 1H). MS: (ESP+) 357 (MH+, 14%).

REFERENCE EXAMPLE 36

N-((5S)-3-(4-(1-tert-Butoxycarbonyl-2R-tert-butyldimethylsilyloxymethyl-2,5-dihydropyrrol-4-yl)phenyl)-2-oxooxazolidin-5-ylmethyl)acetamide The triflate (2R,4R)-2-tert-butyldimethylsilyloxymethyl-1-tert-butoxycarbonyl-4-trifluoromethylsulphonyl-2,5-dihydropyrrole (prepared in the same manner as its 2S epimer Reference Example 13, but via a sequence starting from trans-4-hydroxy-D-proline) (1.34 g, 2.91 mM), palladium(0) bis(dibenzylideneacetone) (0.142 g, 0.156 mM), triphenylarsine (0.190 g, 0.622 mM) and lithium chloride (0.392 g, 9.334 mM) were dissolved in degassed N,N-dimethylformamide (34 ml). The stannane (as used in Examples 1 and 34, 1.24 g, 3.11 mM) was added after 5 minutes and the solution stirred at 40° C. for 24 h. The mixture was treated with aqueous potassium fluoride (2M) (7.8 ml, 15.6 mM), stirred for 30 minutes, filtered through Celite and evaporated. The residue was dissolved in ethyl acetate (40 ml), washed with water (2×15 ml), dried and evaporated to the crude product which was purified by silica-gel MPLC [using 25% MeCN/EtOAc as eluant] to afford the title product (1.02g, 60%);

NMR (300 MHz, D6-DMSO): δ 0.00 (s, 6H), 0.80 (s, 9H), 1.45 (s, 9H), 1.85 (s, 3H), 3.43 (t, 2H), 3.71–3.90 (m, 2H), 4.13 (t, 2H), 4.22–4.35 (m, 1H), 4.48 (d, 1H), 4.57 (br s, 1H), 4.67–4.79 (m, 1H), 6.23 (s, 1H), 7.44–7.57 (m, 4H) and 8.23 (t, 1H). MS: (ESP+) 490 (MH+-isobutylene, 12%) and 546 (MH+, 11%).

REFERENCE EXAMPLE 37

N-((5S)-3-(4-(1-tert-Butoxycarbonyl-2R-hydroxymethyl-2,5-dihydropyrrol-4-yl)phenyl)-2-oxooxazolidin-5-ylmethyl)acetamide The silyl ether (Reference Example 36) (1.02 g, 1.87 mM) in dry THF (30 ml) at 0° C. was treated with tetrabutylammonium fluoride (1.0M in THF) (9.4 ml, 9.37 mM) and stirred for 4.5 h with warming to ambient temperature. Water (1 ml) was added, the solution was evaporated and the residue purified by silica-gel MPLC [using as eluant a mixture increasing in polarity from 2% to 5% MeOH in CH$_2$Cl$_2$] to give the title alcohol (0.59 g, 73%);

NMR (300 MHz, D6-DMSO): δ 1.45 (s, 9H), 1.82 (s, 3H), 3.40 (t, 2H), 3.44–3.53 (m, 1H), 3.64–3.77 (m, 2H), 4.10 (t, 1H), 4.23–4.38 (m, 1H), 4.45 (d, 1H), 4.48 (m, 1H), 4.65–4.77 (m, 2H), 6.29 (s, 1H), 7.43–7.57 (m, 4H) and 8.20 (t, 1H). MS: (ESP+) 432 (MH+, 6%) and 376 (MH+-isobutylene, 43%).

REFERENCE EXAMPLE 38

N-((5S)-3-(4-(2R-Hydroxymethyl-2,5-dihydropyrrol-4-yl)phenyl)-2-oxooxazolidin-5-ylmethyl)acetamide The alcohol (Reference Example 37, 0.548 g, 1.27 mM) was dissolved in trifluoroacetic acid (4 ml) and refluxed for 2 min. before being evaporated at 60° C. The resulting oil was triturated with diethyl ether, the ether decanted off and the resulting powder dried in a stream of argon and then in vacuo to give the title amine as a salt (0.606 g, >100%);

NMR (300 MHz, D6-DMSO): δ 1.80 (s, 3H), 3.40 (t, 2H), 3.60 (dd, 1H), 3.70–3.80 (m, 2H), 4.10 (t, 1H), 4.30 (br s, 2H), 4.50–4.60 (m, 1H), 4.66–4.78 (m, 1H), 6.25 (s, 1H), 7.52 (d, 2H), 7.58 (d, 2H), 8.20 (t, 1H), 9.10 (br s, 1H) and 9.70 (br s, 1H). MS: (ESP+) 332 (MH+, 43%).

EXAMPLE 49

N-((5S)-3-(4-((7aR)[3H,5H]-3-oxo-1,7a-Dihydropyrrolo[1,2c]oxazol-6-yl)phenyl)-2-oxooxazolidin-5-ylmethyl)acetamide The salt (Reference Example 38, 0.600 g, 1.35 mM) was suspended in dichloromethane (10 ml) and treated with triethylamine (0.82 g, 1.13 ml, 8.14 mM) at 0° C. 1,1'-Carbonyl diimidazole (1.09 g, 6.75 mM) was added and the solution stirred for 18 h. The solution washed with 2N HCl, water, dried (MgSO$_4$) and evaporated to a solid and purified by silica-gel MPLC [using as eluant a mixture increasing in polarity from 2% to 5% MeOH in CH$_2$Cl$_2$] to give the title product (0.052 g, 11%);

NMR (300 MHz, D6-DMSO): δ 1.81 (s, 3H), 3.40 (t, 2H), 3.75 (dd, 1H), 4.08–4.15 (m, 2H), 4.30 (dd, 1H), 4.55 (d, 1H), 4.60 (t, 1H), 4.64–4.77 (m, 1H), 4.85–4.94 (m, 1H), 6.42 (s, 1H), 7.55 (s, 4H) and 8.20 (t, 1H). MS: (ESP+) 358 (MH+, 100%).

EXAMPLE 50

The following illustrate representative pharmaceutical dosage forms containing the compound of formula (I), or a pharmaceutically-acceptable salt thereof (hereafter compound X), for therapeutic or prophylactic use in humans:

(a)

| Tablet I | mg/tablet |
|---|---|
| Compound X. | 100 |
| Lactose Ph.Eur. | 179 |
| Croscarmellose sodium | 12.0 |
| Polyvinylpyrrolidone | 6 |
| Magnesium stearate | 3.0 |

(b)

| Tablet II | mg/tablet |
|---|---|
| Compound X | 50 |
| Lactose Ph.Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph.Eur. | 389 |
| Croscarmellose sodium | 100 |
| Magnesium stearate | 1. |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β cyclodextrin may be used to aid formulation.

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of the formula (I),

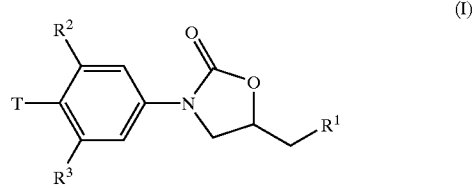

(I)

or a pharmaceutically-acceptable salt thereof, wherein:

R$^1$ is chloro, fluoro, (1–4C)alkanesulfonyloxy, azido, (1–4C)alkoxy, (1–4C)alkylthio, (1–4C)alkylaminocarbonyloxy, or of the formula —NHC(=O)R$^b$ wherein R$^b$ is hydrogen, (1–4C)alkoxy, amino, chloromethyl, dichloromethyl, cyanomethyl, methoxymethyl, acetylmethyl, methylamino, dimethylamino or (1–4C)alkyl, or of the formula —NHS(O)$_n$(1–4C)alkyl wherein n is 0, 1 or 2;

R$_2$ and R$_3$ are independently hydrogen or fluoro;

T is of the formula (IA) or (IB);

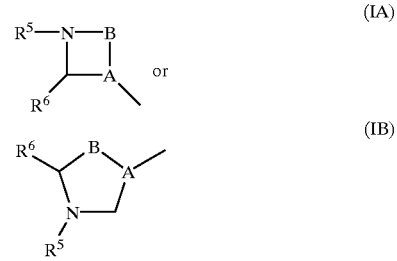

>A—B— is >C=CH—, >C(R$^4$)—CH$_2$—, >CH—CH$_2$—, >C=C(R$^{4a}$)—, >C(R$^4$)—CH(R$^{4a}$)— or >CH—CH(R$^{4a}$), provided that >A—B— is not >C=CH—, >C=C(R$^{4a}$)—, >C(R$^4$)—CH(R$^{4a}$)— or >CH—CH(R$^{4a}$)— when T is of the formula (IA);

R$^4$ is hydrogen, hydroxy, halo, (1–4C)alkyl or (1–4C)alkanoyloxy;

R$^{4a}$ is (1–4C)alkyl;

R$^6$ is (1–4C)alkyl, (1–4C)alkanoylamino-(1–4C)alkyl, hydroxy-(1–4C)alkyl, carboxy, (1–4C)alkoxycarbonyl, AR-oxymethyl, AR-thiomethyl, or R$^5$ (excluding hydrogen);

R⁵ is hydrogen, cyano, 2-((1–4C)alkoxycarbonyl) ethenyl, 2-cyanoethenyl, 2-cyano-2-((1–4C)alkyl) ethenyl, 2-((1–4C)alkylaminocarbonyl)ethenyl, trityl or AR;

or R⁵ is of the formula R¹⁰CO—, R¹⁰SO₂— or R¹⁰CS—
  wherein R¹⁰ is AR, cyclopentyl or cyclohexyl (wherein the last two-mentioned cycloalkyl rings are optionally mono- or disubstituted by substituents independently selected from (1–4C)alkyl (including geminal disubstitution), hydroxy, (1–4C)alkoxy, (1–4C)alkylthio, acetamido, (1–4C)alkanoyl, cyano and trifluoromethyl), benzyloxy, (1–4C)alkoxycarbonyl, hydrogen, amino, trifluoromethyl, (1–4C)alkylamino, di((1–4C)alkyl)amino, 2-(2-furyl)ethenyl, 2-(2-thienyl)ethenyl, 2-phenylethenyl (wherein the phenyl substituent is optionally substituted by up to three substituents independently selected from (1–4C)alkoxy, halo and cyano), benzopyranone or (1–10C)alkyl (wherein (1–10C)alkyl is optionally substituted by hydroxy, benzyloxy, cyano, halo, (1–10C)alkoxy, trifluoromethyl, (1–4C)alkoxy-(1–4C)alkoxy, (1–4C)alkoxy-(1–4C)alkoxy-(1–4C)alkoxy, (1–4C)alkanoyl, (1–4C)alkoxycarbonyl, amino, (1–4C)alkylamino, di((1–4C)alkyl)amino, (1–6C)alkanoylamino, (1–4C)alkoxycarbonylamino, N-(1–4C)alkyl-N-(2–6C)alkanoylamino, (1–4C)alkylS(O)$_p$NH—, (1–4C)alkylS(O)$_p$((1–4C)alkyl)N-, fluoro(1–4C)alkylS(O)$_p$NH—, fluoro(1–4C)alkylS(O)$_p$((1–4C)alkyl)N-, phosphono, (1–4C)alkoxy(hydroxy)phosphoryl, di-(1–4C)alkoxyphosphoryl, (1–4C)alkylS(O)$_q$—, phenylS(O)$_q$— (wherein the phenyl group is optionally substituted by up to three substituents independently selected from (1–4C)alkoxy, halo and cyano), or CY, wherein p is 1 or 2 and q is 0, 1 or 2);
  or R¹⁰ is of the formula R¹¹C(O)O(1–6C)alkyl wherein R¹¹ is an optionally substituted 5- or 6-membered heteroaryl, optionally substituted phenyl, (1–4C)alkylamino, benzyloxy-(1–4C)alkyl or optionally substituted (1–10C)alkyl;
  or R¹⁰ is (1–6C)alkyl-O—;
or R⁵ is of the formula R$^d$OC(R$^e$)=CH(C=O)—, R$^f$C(=O)C(=O)—, R$^g$N=C(R$^h$)C(=O)— or R$^i$NHC(R$^j$)=CHC(=O)— wherein R$^d$ is (1–6C)alkyl, R$^e$ is hydrogen or (1–6C)alkyl, or R$^d$ and R$^e$ together form a (3-4C)alkylene chain, R$^f$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy, R$^g$ is (1–6C)alkyl, hydroxy or (1–6C)alkoxy, R$^h$ is hydrogen or (1–6C)alkyl, R$^i$ is hydrogen, (1–6C)alkyl, optionally substituted phenyl or an optionally substituted 5- or 6-membered heteroaryl and R$^j$ is hydrogen or (1–6C)alkyl;
or R₅ is of the formula R¹⁴CH(R¹³)(CH₂)$_m$— wherein m is 0 or 1, R¹³ is fluoro, cyano, (1–4C)alkoxy, (1–4C)alkylsulfonyl, (1–4C)alkoxycarbonyl or hydroxy, (provided that when m is 0, R¹³ is not fluoro or hydroxy) and R¹⁴ is hydrogen or (1–4C)alkyl;
or R⁵ is ethenyl, 2-(AR)ethenyl, 2-(1–4C)alkylethenyl or of the formula (ID)

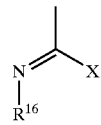

(ID)

wherein X is —OR¹⁵, —SR¹⁵, —NHR¹⁵ and —N(R¹⁵)₂ wherein R¹⁵ is hydrogen (when X is NHR¹⁵ and —N(R¹⁵)₂), (1–4C)alkyl or AR when X is —OR¹⁵, —SR¹⁵ and —NHR¹⁵); and R¹⁶ is cyano, nitro, (1–4C)alkylsulfonyl, (4–10C)cycloalkylsulfonyl, phenylsulfonyl, (1–4C)alkanoyl and (1–4C)alkoxycarbonyl;

or R⁵ and R⁶ are linked to give a group of the formula (IE) to (IK) (in which the N-atom shown is linked to R⁵ in (IA) or (IB), and the adjacent carbon atom shown in (IE) to (IK) is linked to R⁶ in (IA) or (IB)) so that a 5-membered ring is formed which is fused to the ring shown in (IA) or (IB) so as to give a bicyclic ring structure:

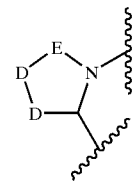

(IE)

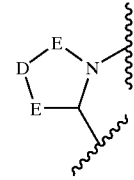

(IF)

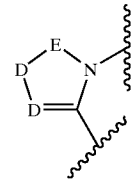

(IG)

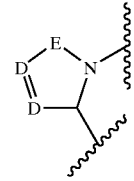

(IH)

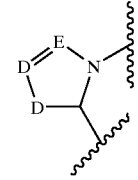

(IJ)

-continued

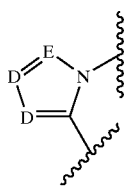
(IK)

wherein
- D is independently selected from >C(R$^7$)(R$^8$) or =C(R$^8$)— when D is connected to a carbon-carbon double bond, S(O)$_p$ (wherein p is 0, 1 or 2) and —O— (when D is not connected to a carbon-carbon double bond) and —NR$^9$ (or N when D is connected to a carbon-carbon double bond);
- E is independently selected from >C(R$^7$)(R$^8$) (or =C(R$^8$)— when E is connected to a carbon-carbon double bond), S(O)$_p$ (wherein p is 0, 1 or 2) and >C=O (when E is not connected to a carbon-carbon double bond);
- R$^7$ and R$^8$ are independently selected from hydrogen, (1–4C)alkyl, (optionally substituted by hydroxy, trifluoromethyl, (1–4C)alkylS(O)$_q$— (wherein q is 0, 1 or 2), (1–4C)alkoxy, carboxy, (1–4C)alkoxycarbonyl, carbamoyl, N-(1–4C)alkylcarbamoyl, di(N-(1–4C)alkyl)carbamoyl, cyano, nitro, amino, N-(1–4C)alkylamino, di(N-(1–4C)alkyl)amino or (1–4C)alkanoylamino), hydroxy (when D and E are not connected to a carbon-carbon double bond), (1–4C)alkoxy, halo, trifluoromethyl, thiol, (1–4C)alkylS(O)$_q$ (wherein q is 0, 1 or 2), carboxy, (1–4C)alkoxycarbonyl, (1–4C)alkanoyl, carbamoyl, N-(1–4C)alkylcarbarmoyl, di(N-(1–4C)alkyl)carbamoyl, (2–4C)alkenyl (optionally substituted by carboxy or (1–4C)alkoxycarbonyl), cyano, (1–4C)alkanoylamino, amino, N-(1–4C)alkylamino, di(N-(1–4C)akyl)amino or nitro;
- R$^9$ is hydrogen, AR, trifluromethyl, hydroxy, cyano, ethenyl, 2-(AR)ethenyl, 2-(1–4C)alkylethenyl, 2-((1–4C)alkoxycarbonyl)ethenyl, 2-cyanoethenyl, 2-cyano-2-((1–4C)alkyl)ethenyl, 2-((1–4C)alkylaminocarbonyl)ethenyl, benzopyranone or (1–10C)alkyl (wherein (1–10C)alkyl is optionally substituted by hydroxy, halo (provided that (1–10C)alkyl is not methyl when substituted by hydroxy or halo), cyano, (1–10C)alkoxy, trifluoromethyl, (1–4C)alkoxy-(1–4C)alkoxy, (1–4C)alkoxy-(1–4C)alkoxy-(1–4C)alkoxy, (1–4C)alkanoyl, (1–4C)alkoxycarbonyl, amino, (1–4C)alkylamino, di((1–4C)alkyl)amino,(1–6C)alkanoylamino, (1–4C)alkoxycarbonylamino, N-(1–4C)alkyl-N-(2–6C)alkanoylamino, (1–4C)alkylS(O)$_p$NH—, (1–4C)alkylS(O)$_p$((1–4C)alkyl)N-, fluoro(1–4C)alkylS(O)$_p$NH—, fluoro(1–4C)alkylS(O)$_p$((1–4C)alkyl)N-, phosphono, (1–4C)alkoxy(hydroxy)phosphoryl, di-(1–4C)alkoxyphosphoryl, (1–4C)alkylS(O)$_q$—, phenylS(O)$_q$— (wherein the phenyl group is optionally substituted by up to three substituents independently selected from (1–4C)alkoxy, halo and cyano), AR or CY (as defined hereinbelow), wherein p is 1 or 2 and q is 0, 1 or 2);
- or R$^9$ is of the formula R$^{11}$C(O)O(1–6C)alkyl wherein R$^{11}$ is an optionally substituted 5- or 6-membered heteroaryl, optionally substituted phenyl, (1–4C)alkylamino, benzyloxy-(1–4C)alkyl or optionally substituted (1–10C)alkyl; or R$^9$ is (1–6C)alkyl-O—;
- AR is optionally substituted phenyl, phenylcarbonyl (when in AR-oxymethyl), optionally substituted phenyl(1–4C)alkyl, optionally substituted 5-membered heteroaryl, or optionally substituted naphthyl wherein the monocyclic heteroaryl ring systems are linked via a ring carbon atom;
- CY is a 4-, 5- or 6-membered cycloalkyl ring, or a 5- or 6-membered cycloalkenyl ring; wherein any of the aforementioned ring systems in CY may be optionally substituted by up to three substituents independently selected from halo, (1–4C)alkyl (including geminal disubstitution when CY is a cycloalkyl or cycloalkenyl ring), acyl, oxo and nitro-(1–4C)alkyl.

2. A compound of claim 1, wherein R$^1$ is acetamido; or a pharmaceutically- acceptable salt thereof.

3. A compound of claim 1 or 2, wherein the compound has a structure of formula (IU):

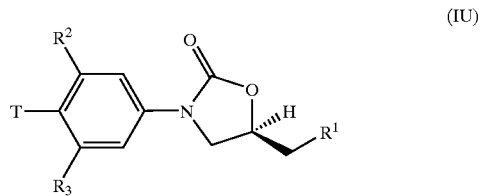
(IU)

wherein R$^1$ is acetamido, R$^2$ and R$^3$ are independently hydrogen or fluoro, and wherein T, as defined in claim 1, is of the formula (IB) (wherein m is 0), >A—B— is of the formula >C=CH—, R$^6$ is benzyloxycarbonyl, (1–4C)alkoxycarbonyl, hydroxy-(1–4C)alkyl, AR-oxymethyl and AR-thiomethyl, R$^5$ is hydrogen, trityl, cyano, acetoxyacetyl, (1–6C)alkoxycarbonyl, AR, R$^{10}$CO— or R$^{10}$SO$_2$—; or a pharmaceutically- acceptable salt thereof.

4. A compound of claim 1 or 2, wherein the compound has a structure of formula (IU):

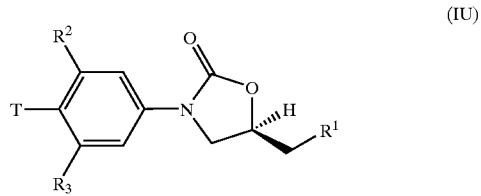
(IU)

wherein R$^1$ is acetamido, R$^2$ and R$^3$ are independently hydrogen or fluoro, and wherein T, as defined in claim 1, is of the formula (IB) (wherein m is 0), >A—B— is of the formula >C=CH—, and R$^5$ and R$^6$ are linked to give a group of the formula (IE) to (IK) so that a 5-membered ring is formed which is fused to the ring shown in (IB) to give a 5/5-bicyclic ring structure; or a pharmaceutically-acceptable salt thereof.

5. A compound of claim 1 or 2, selected from:
- N-((5S)-3-(4-(1-methsulphonyl-2S-benzyloxycarbonyl-2,5-dihydropyrrol-4-yl)phenyl)-2-oxooxazolidin-5-ylmethyl)acetamide;
- N-((5S)-3-(4-(1-cyano-2S-benzyloxycarbonyl-2,5-dihydropyrrol-4-yl)phenyl)-2-oxooxazolidin-5-ylmethyl)acetamide;

N-((5S)-3-(4-(1-formyl-2S-benzyloxycarbonyl-2,5-dihydropyrrol-4-yl)phenyl)-2-oxooxazolidin-5-ylmethyl)acetamide;

N-((5S)-3-(4-(2S-benzoyloxymethyl-1-cyano-2,5-dihydropyrrol-4-yl)phenyl)-2-oxooxazolidin-5-ylmethyl)acetamide;

N-((5S)-3-(4-(2S-benzoyloxymethyl-1-formyl-2,5-dihydropyrrol-4-yl)phenyl)-2-oxooxazolidin-5-ylmethyl)acetamide;

N-((5S)-3-(4-((7aS)(3H,5H)-3-oxo-1,7a-dihydropyrrolo(1,2c)oxazol-6-yl)phenyl)-2-oxooxazolidin-5-ylmethyl)acetamide;

N-((5S)-3-(3-fluoro-4-((7aS)(3H,5H)-3-oxo-1,7a-dihydropyrrolo(1,2c)oxazol-6-yl)phenyl)-2-oxooxazolidin-5-ylmethyl)acetamide;

N-((5S)-3-(3,5-difluoro-4-((7aS)(3H,5H)-3-oxo-1,7a-dihydropyrrolo(1,2c)oxazol-6-yl)phenyl)-2-oxooxazolidin-5-ylmethyl)acetamide;

N-((5S)-3-(4-((7aS)(5H)-3-oxo-1,2,3,7a-tetrahydropyrrolo(1,2c)imidazol-6-yl)phenyl)-2-oxooxazolidin-5-ylmethyl)acetamide;

N-((5S)-3-(4-((7aR)(3H,5H)-3-oxo-1,7a-dihydropyrrolo(1,2c)oxazol-6-yl)phenyl )-2-oxooxazolidin-5-ylmethyl)acetamide; or a pharmaceutically-acceptable salt thereof.

6. A pharmaceutical composition which comprises a compound of claim 1 or 2, or a pharmaceutically acceptable salt thereof, and a pharmaceutically acceptable diluent or carrier.

7. A method of manufacturing a medicament, comprising combining a compound of claim 1 or 2, or a pharmaceutically acceptable salt thereof, and a pharmaceutically acceptable diluent or carrier.

8. A method for producing an antibacterial effect in a warm-blooded animal, comprising administering to said animal an effective amount of a compound of claim 1 or 2, or a pharmaceutically acceptable salt thereof.

9. The method of claim 8, wherein the warm-blooded animal is a human.

10. The pharmaceutical composition of claim 6, wherein the composition is active against Gram-positive pathogens.

11. The method of claim 8, wherein the compound is administered orally or parenterally.

12. The method of claim 8, wherein the compound is administered topically.

13. A compound of claim 3, wherein $R^{10}$ is hydrogen or (1–10C)alkyl (optionally substituted by benzyloxy or hydroxy); or a pharmaceutically acceptable salt thereof.

* * * * *